United States Patent [19]
Kawchuk et al.

[11] Patent Number: 5,998,701
[45] Date of Patent: Dec. 7, 1999

[54] POTATOES HAVING IMPROVED QUALITY CHARACTERISTICS AND METHODS FOR THEIR PRODUCTION

[75] Inventors: Lawrence Michael Kawchuk, Coaldale; John David Armstrong; Dermot Roborg Lynch, both of Lethbridge; Norman Richard Knowles, Edmonton, all of Canada

[73] Assignees: Her Majesty the Queen in right of Canada as represented by the Department of Agriculture; Agri-Food Canada, both of Lethbridge, Canada

[21] Appl. No.: 08/868,786

[22] Filed: Jun. 4, 1997

Related U.S. Application Data

[60] Provisional application No. 60/036,946, Feb. 10, 1997.
[51] Int. Cl.$^6$ .............................. A01H 5/00; C12N 15/29; C12N 15/54; C12N 15/82; C12P 19/04
[52] U.S. Cl. ...................... 800/284; 800/286; 800/317.2; 435/101; 435/194; 435/468
[58] Field of Search ............................ 800/205, DIG. 42, 800/284, 286, 317.2; 435/172.3, 194, 101, 468; 536/23.6, 24.5

[56] References Cited

U.S. PATENT DOCUMENTS

| | | | |
|---|---|---|---|
| 4,407,956 | 10/1983 | Howell | 435/172 |
| 5,387,756 | 2/1995 | Burrell et al. | 800/205 |
| 5,387,757 | 2/1995 | Bridges et al. | 800/205 |
| 5,451,514 | 9/1995 | Boudet et al. | 435/172.3 |
| 5,545,815 | 8/1996 | Fischer et al. | 800/205 |
| 5,585,545 | 12/1996 | Bennett et al. | 800/205 |

FOREIGN PATENT DOCUMENTS

| | | |
|---|---|---|
| 2040793 | 10/1991 | Canada . |
| 0 438 904 A1 | 7/1991 | European Pat. Off. . |
| 0 530 978 A2 | 3/1993 | European Pat. Off. . |
| 0 812 917 A1 | 12/1997 | European Pat. Off. . |
| WO 90/12876 | 11/1990 | WIPO . |
| WO 92/11375 | 7/1992 | WIPO . |
| WO 92/14827 | 9/1992 | WIPO . |
| WO 94/00563 | 1/1994 | WIPO . |
| WO 94/28149 | 12/1994 | WIPO . |

OTHER PUBLICATIONS

Bradford, Marion M. 1976. A Rapid and Sensitive Method for the Quantitation of Microgram Quantities of Protein Utilizing the Principle of Protein–Dye Binding, Anal. Biochem. 72:243–254.
Owen et al. Bio/Technology 10(7):790–794, Jul. 1992.
Steinecke et al. EMBO J 11(4):1525–1530, 1992.
Tauladoraki et al. Nature 366:469–472, Dec. 1993.
Wegener et al. Mol. Gen. Genet. 245:465–470, 1994.
Evans et al. Biochem. Soc. Trans. 20:3445, 1992.
Mazzolini et al. Plant Mol. Biol. 20:715–731, 1992.
Nakano, Kenichi, et al. 1989. Molecular Cloning of cDNA Encoding Potato Amyloplast α–Glucan Phosphorylase and the Structure of Its Transit Peptide. J. Biochem. 106:691–695.
Nakano, Kenichi and Fukui, Toshio. 1986. The Complete Amino Acid Sequence of Potato α–Glucan Phosphorylase. J. Biol. Chem. 26:8230–8256.
Napoli, Carolyn, et al. 1990. Introduction of a Chimeric Chalcone Synthase Gene into Petunia Results in Reversible Co–Suppression of Homologous Genes in trans. Plant Cell 2:279–289.
Odell, Joan T., et al. 1985. Identification of DNA Sequences Required for Activity of the Cauliflower Mosaic Virus 35S Promoter. Nature 313:810–812.
Ohta, Shozo, et al. 1991. High–Level Expression of a Sweet Potato Sporamin Gene Promoter β–glucuroidase (GUS) Fusion Gene in the Stems of Transgenic Tobacco Plants is Conferred by Multiple Cell Type–Specific Reg. Elements. Mol. Gen. Genet. 225:369–378.
Ortiz, R. and Huaman, Z. 1994. Inheritance of Morphological and Tuber Characteristics. In:Potato Genetics. Bradshaw, J.E. and Mackay, G.R. (eds.) 263–283 pp.
Sambrook, J., et al. 1989. Molecular Cloning, A Laboratory Manual. 2nd Ed. Cold Spring Harbor Laboratory Press, N.Y., pp. 1–13, 1. 21–28, 1.53–1.74, 1.85–1.89, 1.105–1.110.
Seymour, G.B., et al. 1993. Down–regulation of Two Non–Homologous Endogenous Tomato Genes with a Single Chimaeric Sense Gene Construct. Plant Mol. Biol. 23:1–9.
Shalar, Tamar et al. 1992. The Tomato 66.3 kD Polyphenoloxidase Gene: Molecular Identification and Development Expression. Plant Cell 4:135–147.
Shallenberger, R. S., et al. 1959. Role of the Sugars in the Browing Reaction in Potato Chips. Agric. And Food Chem. 7:274–277.
Smith, C.J.S., et al. 1988. Antisense RNA Inhibition of Polygalacturonase Gene Expression in Transgenic Tomatoes. Nature 334:724–726.
Smith, C.J.S., et al. 1990. Expression of a Truncated Tomato Polygalacturonase Gene Inhibits Expression of the Endogenous Gene in Transgenic Plants. Mol. Gen. Genet. 244:477–481.

(List continued on next page.)

*Primary Examiner*—David T. Fox
*Attorney, Agent, or Firm*—Greenlee, Winner and Sullivan, PC

[57] ABSTRACT

Potato plants which exhibit reduced levels of α glucan L-type tuber phosphorylase (GLTP) or α glucan H-type tuber phosphorylase (GHTP) enzyme activity within the potato tuber are provided. The conversion of starches to sugars in potato tubers, particularly when stored at temperatures below 7° C., is reduced in tubers exhibiting reduced GLTP or GHTP enzyme activity. Reducing cold-sweetening in potatoes allows for potato storage at cooler temperatures, resulting in prolonged dormancy, reduced incidence of disease, and increased storage life. Methods for producing potato plants which produce tubers exhibiting reduced GLTP or GHTP enzyme activity are also provided. Reduction of GLTP or GHTP activity within the potato tuber may be accomplished by such techniques as suppression of gene expression using homologous antisense RNA, the use of co-suppression, regulatory silencing sequences, chemical and protein inhibitors, or the use of site-directed mutagenesis or the isolation of alternative alleles to obtain GLTP or GHTP variants with reduced starch affinity or activity.

54 Claims, 7 Drawing Sheets

OTHER PUBLICATIONS

Sonnewald, Uwe, et al. 1995. A Second L–type Isozyme of Potato Glucan Phosphorylase: cloning, antisense inhibition and expression analysis. Plant Molecular Biology 27:567–576.

Sowokinos, J. 1990. Stress–Induced Alterations in Carbohydrate Metaloism. In: The Molecular and Cellular Biology of the Potato. M.A. Mayo and W.D. Parks (eds.) Chapter 11,137–157.

Stalker, David M., et al. 1981. Nucleotide Sequence of the Region of the Origin of Replication of the Broad Host Range Plasmid RK2. Mol. Gen. Genet. 181:8–12.

Steup, Martin. 1990. Starch Degrading Enzymes. In: Methods in Plant Biochemistry. P.M. Dey and J.B. Harborne (eds.) Academic Press, London vol. 3, Chptr. 7:103–128.

Stiekema, Willem J., et al. 1988. Molecular Cloning and Analysis of Four Potato Tuber mRNAs. Plant Mol. Biol. 11:255–269.

Stukelji, B., et al. 1990. Nucleotide and deduced amino acid sequence of an aspartic proteinase inhibitor homologue from potato tubers (*Solanum tuberosum* L..). Nucl. Acids Res. 18:4605.

Takaha, Takeshi, et al. 1993. Disproportionating Enzyme (4–α–Glucanotransferase: EC 2.4.1.25) of Potato J. Biol. Chem. 268:1391–1396.

Thuring, R.W.J., et al. 1975. A Freeze–Squeeze Method for Recovering Long DNA from Agarose Gels. Analytical Biochemistry 66:213–220.

Van der Krol, Alexander R., et al. 1988. Antisense Genes in Plants: An Overview. Gene 72:45–50.

Van der Krol, Alexander R., et al. 1990. Flavonoid Genes in Petunia: Addition of a Limited Number of Gene Copies May Lead to a Suppression of Gene Expression. Plant Cell 2:291–299.

Weaver, M.L., et al. 1978. Potato Composition: H. Tissue Selection and its Effects on Total Sugar, Total Reducing Sugar, Glucose, Fructose and Sucrose Contents. Am. Pot. J. 59:83–93.

Weintraub, Harold M. 1990. Antisense RNA and DNA. Scientific American 1:40–46.

Winnacker, Ernst L. 1987. Cloning in Plants. In:From Genes to Clones. VCH Verlagsgesellschaft mbH, Federal Republic of Germany. Chptr 10:397–411.

Yoshida, Nobumasa, et al. 1992. A Nuclear Gene Encoding β–amylase of Sweet Potato. Gene. 10:255–259.

Jorgensen, Richard A. 1995. Cosuppression, Flower Color, Patterns, and Metastable Gene Expression States. Science 268:686–691.

Kawchuk, L.M., et al. 1990. Resistance in Transgenic Potato Expressing the Potato Leafroll Virus Coat Protein Gene. Molecular Plant–Microbe Interactions 3:301–307.

Kawchuk, L.M., et al. 1991. Sense and Antisense RNA–Mediated Resistance to Potato Leafroll Virus in Russet Burbank Potato Plants. Mol. Plant Microbe–Inter. 4:247–253.

Kay, Robert, et al. 1987. Duplication of CaMV 35S Promoter Sequences Creates a Strong Enhancer for Plant Genes. Science 236:1299–1302.

Kruger, Nicholas J. and Hammond, John B. W. 1988. Molecular Comparison of Pyrophosphate– and ATP–Dependent Fructose 6–Phosphate 1–Phosphotransferases from Potato Tuber. Plant Physiol. 86:645–648.

Laemmli, U.K. 1970. Cleavage of Structural Proteins during the Assembly of the Head of Bacteriophage T4. Nature (London) 227:680–685.

Lin, Tsan–Piao, et al. 1988. Isolation and Characterization of a Starchless Mutant of *Arabidopsis thaliana* (L.) Heynh Lacking ADPglucose Pyrophosphorylase Activity. Plant Physiol. 86:1131–1135.

Loiselle, F., et al. 1990. Genetic Components of Chip Color Evaluated After Harvest, Cold Storage and Reconditioning. American Poato Journal 67:633–646.

Lynch, D.R., et al. 1992. Genetic Components of Potato Chip Quality Evaluated in Three Environments and Under Various Storage Regimes. Can. J. Plant. Sci. 72:535–543.

Matzke, Marjori A. and Matzke, Antonius J.M. 1995. How and Why Do Plants Inactivate Homologous (Trans)genes? Plant Physiol. 107:679–685.

Meyer, P. and Saedler, H. 1996. Homology–Dependent Gene Silencing in Plants. Annu. Rev. Plant Physiol. 47:23–48.

Mori, Hiroyuki, et al. 1991. Potato Tuber Type H Phosphorylase Isozyme. J. Biol. Chem. 266:18446–18453.

Muller–Rober, Bernd Thomas, et al. 1990. One of Two Different ADP–glucose Pyrophosphorylase Genes from Poato Response Strongly to Elevated Levels of Sucrose. Mol. Gen. Genet. 224:136–146.

De Block, M. 1988. Genotype–Independent Leaf Disc Transformation of Potato (Solanum tuberosum) using *Agrobacterium tumefaciens*. Theoretical and Applied Genetics 76:767–774.

de Carvalho, Fernanda, et al. 1992. Suppression of β–1, 3–glucanase Transgene Expression in Homozygous Plants. EMBO J. 11:2595–2602.

Depicker, A. et al. 1982. Nopaline Synthase: Transcript Mapping and DNA Sequence. Mol. and Appl. Genet. 1:561–573.

Dixon, Wendy L. et al. 1981. Cold–Lability of Phosphofructokinase from Potato Tubers. Phytochemistry 20:969–972.

Dorlhac de Borne, Francois, et al. 1994. Co–Suppression of Nitrate Reductase Host Genes and Transgenes in Transgenic Tobacco Plants. Mol. Gen. Genetics 243:613–621.

Ecker, Joseph R. and Davis, Ronald W. 1986. Inhibition of Gene Expression in Plant Cells by Expression of Antisense RNA. Proc. Natl. Acad. Sci. 83:5372–5376.

Fling, May E., et al. 1985. Nucleotide Sequence of the Transposon Tn7 Gene Encoding an Aminoglycoside–modifying Enzyme, 3" (9)–O–nucleotidyltransferase. Nucleic Acids Research 13:7095–4807.

Fraley, Robert T., et al. 1983. Expression of Bacterial Genes in Plant Cells. Proc. Natl. Acad. Sci. 80:4803–4807.

Fraley, Robert T., et al. 1985. The SEV System: A New Disarmed TI Plasmid Vector System for Plant Transformation. Bio/Technology 3:629–635.

Fray, Rupert G. and Grierson, Donald. 1983. Identification and Genetic Analysis of Normal and Mutant Phytoene Synthase Genes of Tomato by Sequencing, Complementation and Co–Suppression. Plant. Mol. Biol. 22:589–602.

Gielen, M., et al. 1984. The Complete Nucleotide Sequence of the TL–DNA of the *Agrobacterium tumefaciens* Plasmid pTiAch5. EMBO J. 3:835–846.

Haseloff, Jim and Gerlach, Wayne L. 1988. Simple RNA Enzymes with New and Highly Specific Endoribonuclease Activities. Nature 334:585–591.

Hart, Craig M., et al. 1992. Regulated inactivation of Homologous Gene Expression in Transgenic *Nicotiana sylvestris* Plants Containing a Defense–Related Tobacco Chitinase Gene. Mol. Gen. Genetic 235:179–188.

Alber, Tom and Kawasaki, Glenn 1982. Nucleotide Sequence of the Triose Phosphate Isomerase Gene of *Saccharomyces cerevisiae*. Mol. and Appl. Genet. 1:419–434.

ap Rees, T., et al. 1988. Effects of Low Temperature on the Respiratory Metabolism of Carbohydrates by Plants. Symp. Soc. Exp. Biol. 42:377–393.

Bevan, Michael W., et al. 1983. A Chimaeric Antibiotic Resistance Gene as a Selectable Marker for Plant Cell Transformation. Nature (London) 304:184–187.

Bevan, M., et al. 1986. The Structure and Transcription Start Site of a Major Potato Tuber Protein Gene. Nucleic Acids Res. 14(11): 4625–4638.

Birnboim, H.C. and Doly, J. 1979. A Rapid Alkaline Extraction Procedure for Screening Recombinant Plasmid DNA. Nucleic Acids Res. 7:1513–1523.

Blennow, Andreas and Johansson, Gote. 1991. Isolation of Q–Enzyme with M, 103 000 from Potato Tubers. Phytochemistry 30:437–444.

Brisson, Normand, et al. 1989. Maturation and Subcellular Compartmentation of Potato Starch Phosphorylase. The Plant Cell 1:559–566.

Brusslan, Judy A. and Tobin, Elaine M. 1995. Isolation of New Promoter–Mediated Co–Suppressed Lines in *Arabidopsis thaliana*. Plant Molecular Biology 27:809–813.

Burton, W.G. 1989. Specific Gravity as a Guide to the Content of Dry Matter and of Starch in Potato Tubers. In: The Potato. Longman Scientific and Technical 305–308 pp.

Cannon, Maura, et al. 1990. Organ–Specific Modulation of Gene Expression in Transgenic Plants using Antisense RNA. Plant Molecular Biology 15:39–47.

Classen, Pieternel A.M., et al. 1991. Potential Role of Pyrophosphate: Fructose 6–Phosphate Phosphotransferase in Carbohydrate Metabolism of Cold Stored Tubers of *Solanum tuberosum* cv Bintje. Plant Physiol. 95:1243–1249.

Coffin, R.H., et al. 1987. Effect of Low Temperature Storage on Sugar Concentrations and Chip Color of Certain Processing Potato Cultivars and Selections. J. Food Sci. 52:639–645.

Davies, H.V. and Viola, R. 1992. Regulation of Sugar Accumulation in Stored Potato Tubers. Postharvest News and Information 3:97–100.

```
ELPKAYYA-TAESVRDTLIINWNATYEFYEKMNVKQAYYLSMEFLQGRAL   49
ELPKAFFA-TAQSVRDSLLINWNATYDIYEKLNMKQAYYLSMEFLQGRAL   49
EPLQAYYAATADSVRDRLIKQWNDTYLHYDKVNPKQTYYLSMEYLQGRAL   50
 *  .* .* ** .****  *.  .**.**    *.*.* **.******.******

LNAIGNLGLTGPYADALTKLGYSLEDVARQEPDAALGNGGLGRLASCFLD   99
LNAIGNLELTGDFAEALKNLGHNLENVASQEPDAALGNGGLGRLASCFLD   99
TNAVGNLDIHNAYADALNKLGQQLEEVVEQEKDAALGNGGLGRLASCFLD  100
 **.***.. . .*.**..**   **.*. ** *****************

SMATLNYPAWGYGLRYQYGLFKQLITKDGQEEVAENWLEMGNPWEIVRND  149
SLATLNYPAWGYGLRYKYGLFKQRITKDGQEEVAEDWLEIGSPWEVVRND  149
SMATLNLPAWGYGLRYRYGLFKQLITKAGQEEVPEDWLEKFSPWEIVRHD  150
*.**** ********* .****** ***.*****.*.***   .***.**.*

ISYPVKFYGKVIEGADGRKEWAGGEDITAVAYDVPIPGYKTKTTINLRLW  199
VSYPIKFYGKVSTGSDGKRYWIGGEDIKAVAYDVPIPGYKTRTTISLRLW  199
VVFPIRFFGHVEVLPSGSRKWVGGEVLQALAYDVPIPGYRTKNTNSLRLW  200
 . *...*.*.*    ..*.. * ***  . *.**********.*..* .****

TTKLAAEAFDLYAFNNGDH  218
STQVPSADFDLSAFNAGEH  218
EAKASSEDFNLFLFNDGQY  219
 . .   ....*.*  **.*..
```

FIG.5

```
GAACTTCCCAAGGCATACTATGCA---ACTGCAGAGAGTGTTCGAGATAC    47
GAGCTCCCTAAGGCATTCTTTGCA---ACAGCTCAAAGTGTTCGTGATTC    47
GAGCCACTACAAGCATACTATGCTGCTACTGCTGACAGTGTTCGTGAT-C    49
**.*   *   .****.**.***.    **.**. * ********.*** *

GCTCATTATAA-ATTGGAATGCCACATACGAATTCTATGAAAAGATGAAT    96
GCTCCTTATTA-ATTGGAATGCTACGTATGATATTTATGAAAAGCTGAAC    96
GCTTGATCAAACAATGGAATGACACCTATCTTCATTATGACAAAGTTAAT    99
***   .*  ..* *.*******  ** **   . . . ***** **. *.**

GTAAAGCAGGCATATTACTTGTCTATGGAATTTCTTCAGGGAAGAGCTTT   146
ATGAAGCAAGCGTACTATCTATCCATGGAATTTCTGCAGGGTAGAGCATT   146
CCAAAGCAAACATACTACTTATCAATGGAGTATCTCCAGGGGCGAGCTTT   149
   .*****..*.** **  *.** *****.*.*** *****. ****.**

ACTCAATGCTATTGGTAACTTGGGGCTAAC-CGGACCTTATGCAGATGCT   195
GTTAAATGCAATTGGTAATCTGGAGCTTAC-TGGTGACTTTGCGGAAGCT   195
GACAAATGCAGTTGGAAACTTAGA-CATCCACAATGCATATGCTGATGCT   198
.   ****..****.**   *.*. *..  *   ... *.***.**.***

TTAACTAAGCTCGGATACAGTTTAGAGGATGTAGCCAGGCAGGAACCGGA   245
TTGAAAAACCTTGGCCACAATCTAGAAAATGTGGCTTCTCAGGAACCAGA   245
TTAAACAAACTGGGTCAGCAGCTTGAGGAGGTCGTTGAGCAGGAAAAGA    248
**.*  ** ** ** **  *  .. *.**..*.** *  .******   .**

TGCAGCTTTAGGTAATGGAGGTTTAGGAAGACTTGCTTCTTGCTTTCTGG   295
TGCTGCTCTTGGAAATGGGGGTTTGGGACGGCTTGCTTCCTGTTTCTTGG   295
TGCAGCATTAGGAAATGGTGGTTTAGGAAGGCTCGCTTCATGCTTTCTTG   298
***.**. *.**.***** .*****.*****.*** **** ** **   *.*

ACTCAATGGCGACACTAAACTACCCTGCATGGGGCTATGGACTTAGATAC   345
ACTCTTTGGCAACACTAAACTACCCAGCATGGGGCTATGGACTTAGGTAC   345
ATTCCATGGCCACATTGAACCTTCCAGCATGGGGTTATGGCTTGAGGTAC   348
* **  .**** *** *.*  .*** .  **.********  ***** *.**.***

CAATATGGCCTTTTCAAACAGCTTATTACAAAAGATGGACAGGAGGAAGT   395
AAGTATGGTTTATTTAAGCAACGGATTACAAAAGATGGTCAGGAGGAGGT   395
AGATATGGACTTTTTAAGCAGCTTATCACAAAGGCTGGGCAAGAAGAAGT   398
 ..*****  *.** **.** .*.** *****.* ***.**.**.**.**

TGCTGAAAATTGGCTCGAGATGGGAAATCCATGGGAAATTGTGAGGAATG   445
GGCTGAAGATTGGCTTGAAATTGGCAGTCCATGGGAAGTTGTGAGGAATG   445
TCCTGAAGATTGGTTGGAGAAATTAGTCCCTGGGAAATTGTAAGGCATG    448
 . *****.*****. *  **.*   . .***  ****** .***.*** ***

ATATTTCGTATCCCGTAAAATTCTATGGGAAGGTCATTGAAGGAGCTGAT   495
ATGTTTCATATCCTATCAAATTCTATGGAAAAGTCTCTACAGGATCAGAT   495
ATGTTGTCTTTCCTATCAGGTTTTTTGGTCATGTTGAAGTCCTCCCTTCT   498
**.**.  *.***. * *..** *.***. *.** .    . . *.. *
```

FIG. 6A

```
GGGAGGAAGGAATGGGCTGGCGGAGAAGATATAACTGCTGTTGCCTATGA   545
GGAAAGAGGTATTGGATTGGTGGAGAGGATATAAAGGCAGTTGCGTATGA   545
GGCTCGCGAAAATGGGTTGGTGGAGAGGTCCTACAGGCTCTTGCATATGA   548
** . * ...*.***. *** *****.*.  **  .**. **** *****

TGTCCCAATACCAGGATATAAAACAAAAACAACGATTAACCTTCGATTGT   595
TGTTCCCATACCAGGGTATAAGACCAGAACCACAATCAGCCTTCGACTGT   595
TGTGCCAATTCCAGGATACAGAACTAAAAACACTAATAGTCTTCGTCTCT   598
*** ** **.*****.** *..** *.**   **.*. *. *****. * *

GGACAAC-AAAGCTAGCTGCAGAAGCTTTTGATTTATATGCTTTTAACAA   644
GTCTAC-ACAGGTTCCATCAGCGGATTTTGATTTATCTGCTTTCAATGC    644
GGGAAGCCAAAGCAAGCT-CTGAGGATTTCAACTTGTTTCTGTTTAATGA   647
**. ..* * **  .. *. *.* .* *** .* **.* *  .** **  .

TGGAGACCATGC     656
TGGAGAGCACAC     656
TGGACAGTATGA     659
**** *  *  .
```

FIG.6B

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 3101 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Solanum tuberosum (ix) FEATURE:
      (A) NAME/KEY: CDS
      (B) LOCATION: 44..2944
      (D) OTHER INFORMATION: /product= "potato alpha-glucan
         L-type tuber phosphorylase"

(ix) FEATURE:
      (A) NAME/KEY: mat_peptide
      (B) LOCATION: 194..2941

(ix) FEATURE:
      (A) NAME/KEY: sig_peptide
      (B) LOCATION: 44..193

(xi) SEQUENCE DESCRIPTION: SEQ ID NO:1:

```
ATCACTCTCA TTCGAAAAGC TAGATTTGCA TAGAGAGCAC AAA ATG GCG ACT GCA         55
                                                Met Ala Thr Ala
                                                -50

AAT GGA GCA CAC TTG TTC AAC CAT TAC AGC TCC AAT TCC AGA TTC ATC        103
Asn Gly Ala His Leu Phe Asn His Tyr Ser Ser Asn Ser Arg Phe Ile
    -45                 -40                 -35

CAT TTC ACT TCT AGA AAC ACA AGC TCC AAA TTG TTC CTT ACC AAA ACC        151
His Phe Thr Ser Arg Asn Thr Ser Ser Lys Leu Phe Leu Thr Lys Thr
-30                 -25                 -20                 -15

TCC CAT TTT CGG AGA CCC AAA CGC TGT TTC CAT GTC AAC AAT ACC TTG        199
Ser His Phe Arg Arg Pro Lys Arg Cys Phe His Val Asn Asn Thr Leu
            -10                 -5                   1

AGT GAG AAA ATT CAC CAT CCC ATT ACT GAA CAA GGT GGT GAG AGC GAC        247
Ser Glu Lys Ile His His Pro Ile Thr Glu Gln Gly Gly Glu Ser Asp
```

```
                 5                    10                        15
CTG AGT TCT TTT GCT CCT GAT GCC GCA TCT ATT ACC TCA AGT ATC AAA        295
Leu Ser Ser Phe Ala Pro Asp Ala Ala Ser Ile Thr Ser Ser Ile Lys
         20                  25                  30

TAC CAT GCA GAA TTC ACA CCT GTA TTC TCT CCT GAA AGG TTT GAG CTC        343
Tyr His Ala Glu Phe Thr Pro Val Phe Ser Pro Glu Arg Phe Glu Leu
35                  40                  45                  50

CCT AAG GCA TTC TTT GCA ACA GCT CAA AGT GTT CGT GAT TCG CTC CTT        391
Pro Lys Ala Phe Phe Ala Thr Ala Gln Ser Val Arg Asp Ser Leu Leu
                 55                  60                  65

ATT AAT TGG AAT GCT ACG TAT GAT ATT TAT GAA AAG CTG AAC ATG AAG        439
Ile Asn Trp Asn Ala Thr Tyr Asp Ile Tyr Glu Lys Leu Asn Met Lys
         70                  75                  80

CAA GCG TAC TAT CTA TCC ATG GAA TTT CTG CAG GGT AGA GCA TTG TTA        487
Gln Ala Tyr Tyr Leu Ser Met Glu Phe Leu Gln Gly Arg Ala Leu Leu
                 85                  90                  95

AAT GCA ATT GGT AAT CTG GAG CTT ACT GGT GCA TTT GCG GAA GCT TTG        535
Asn Ala Ile Gly Asn Leu Glu Leu Thr Gly Ala Phe Ala Glu Ala Leu
         100                 105                 110

AAA AAC CTT GGC CAC AAT CTA GAA AAT GTG GCT TCT CAG GAA CCA GAT        583
Lys Asn Leu Gly His Asn Leu Glu Asn Val Ala Ser Gln Glu Pro Asp
115                 120                 125                 130

GCT GCT CTT GGA AAT GGG GGT TTG GGA CGG CTT GCT TCC TGT TTT CTG        631
Ala Ala Leu Gly Asn Gly Gly Leu Gly Arg Leu Ala Ser Cys Phe Leu
                 135                 140                 145

GAC TCT TTG GCA ACA CTA AAC TAC CCA GCA TGG GGC TAT GGA CTT AGG        679
Asp Ser Leu Ala Thr Leu Asn Tyr Pro Ala Trp Gly Tyr Gly Leu Arg
         150                 155                 160

TAC AAG TAT GGT TTA TTT AAG CAA CGG ATT ACA AAA GAT GGT CAG GAG        727
Tyr Lys Tyr Gly Leu Phe Lys Gln Arg Ile Thr Lys Asp Gly Gln Glu
         165                 170                 175

GAG GTG GCT GAA GAT TGG CTT GAA ATT GGC AGT CCA TGG GAA GTT GTG        775
Glu Val Ala Glu Asp Trp Leu Glu Ile Gly Ser Pro Trp Glu Val Val
                 180                 185                 190

AGG AAT GAT GTT TCA TAT CCT ATC AAA TTC TAT GGA AAA GTC TCT ACA        823
Arg Asn Asp Val Ser Tyr Pro Ile Lys Phe Tyr Gly Lys Val Ser Thr
195                 200                 205                 210

GGA TCA GAT GGA AAG AGG TAT TGG ATT GGT GGA GAG GAT ATA AAG GCA        871
Gly Ser Asp Gly Lys Arg Tyr Trp Ile Gly Gly Glu Asp Ile Lys Ala
                 215                 220                 225

GTT GCG TAT GAT GTT CCC ATA CCA GGG TAT AAG ACC AGA ACC ACA ATC        919
Val Ala Tyr Asp Val Pro Ile Pro Gly Tyr Lys Thr Arg Thr Thr Ile
         230                 235                 240

AGC CTT CGA CTG TGG TCT ACA CAG GTT CCA TCA GCG GAT TTT GAT TTA        967
Ser Leu Arg Leu Trp Ser Thr Gln Val Pro Ser Ala Asp Phe Asp Leu
         245                 250                 255

TCT GCT TTC AAT GCT GGA GAG CAC ACC AAA GCA TGT GAA GCC CAA GCA       1015
Ser Ala Phe Asn Ala Gly Glu His Thr Lys Ala Cys Glu Ala Gln Ala
         260                 265                 270

AAC GCT GAG AAG ATA TGT TAC ATA CTC TAC CCT GGG GAT GAA TCA GAG       1063
Asn Ala Glu Lys Ile Cys Tyr Ile Leu Tyr Pro Gly Asp Glu Ser Glu
275                 280                 285                 290

GAG GGA AAG ATC CTT CGG TTG AAG CAA CAA TAT ACC TTA TGC TCG GCT       1111
Glu Gly Lys Ile Leu Arg Leu Lys Gln Gln Tyr Thr Leu Cys Ser Ala
                 295                 300                 305

TCT CTC CAA GAT ATT ATT TCT CGA TTT GAG AGG AGA TCA GGT GAT CGT       1159
Ser Leu Gln Asp Ile Ile Ser Arg Phe Glu Arg Arg Ser Gly Asp Arg
         310                 315                 320

ATT AAG TGG GAA GAG TTT CCT GAA AAA GTT GCT GTG CAG ATG AAT GAC       1207
Ile Lys Trp Glu Glu Phe Pro Glu Lys Val Ala Val Gln Met Asn Asp
```

```
              325                 330                 335
ACT CAC CCT ACA CTT TGT ATC CCT GAG CTG ATG AGA ATA TTG ATA GAT    1255
Thr His Pro Thr Leu Cys Ile Pro Glu Leu Met Arg Ile Leu Ile Asp
    340                 345                 350

CTG AAG GGC TTG AAT TGG AAT GAA GCT TGG AAT ATT ACT CAA AGA ACT    1303
Leu Lys Gly Leu Asn Trp Asn Glu Ala Trp Asn Ile Thr Gln Arg Thr
355                 360                 365                 370

GTG GCC TAC ACA AAC CAT ACT GTT TTG CCT GAG GCA CTG GAG AAA TGG    1351
Val Ala Tyr Thr Asn His Thr Val Leu Pro Glu Ala Leu Glu Lys Trp
                375                 380                 385

AGT TAT GAA TTG ATG CAG AAA CTC CTT CCC AGA CAT GTC GAA ATC ATT    1399
Ser Tyr Glu Leu Met Gln Lys Leu Leu Pro Arg His Val Glu Ile Ile
            390                 395                 400

GAG GCG ATT GAC GAG GAG CTG GTA CAT GAA ATT GTA TTA AAA TAT GGT    1447
Glu Ala Ile Asp Glu Glu Leu Val His Glu Ile Val Leu Lys Tyr Gly
        405                 410                 415

TCA ATG GAT CTG AAC AAA TTG GAG GAA AAG TTG ACT ACA ATG AGA ATC    1495
Ser Met Asp Leu Asn Lys Leu Glu Glu Lys Leu Thr Thr Met Arg Ile
    420                 425                 430

TTA GAA AAT TTT GAT CTT CCC AGT TCT GTT GCT GAA TTA TTT ATT AAG    1543
Leu Glu Asn Phe Asp Leu Pro Ser Ser Val Ala Glu Leu Phe Ile Lys
435                 440                 445                 450

CCT GAA ATC TCA GTT GAT GAT GAT ACT GAA ACA GTA GAA GTC CAT GAC    1591
Pro Glu Ile Ser Val Asp Asp Asp Thr Glu Thr Val Glu Val His Asp
                455                 460                 465

AAA GTT GAA GCT TCC GAT AAA GTT GTG ACT AAT GAT GAA GAT GAC ACT    1639
Lys Val Glu Ala Ser Asp Lys Val Val Thr Asn Asp Glu Asp Asp Thr
            470                 475                 480

GGT AAG AAA ACT AGT GTG AAG ATA GAA GCA GCT GCA GAA AAA GAC ATT    1687
Gly Lys Lys Thr Ser Val Lys Ile Glu Ala Ala Ala Glu Lys Asp Ile
        485                 490                 495

GAC AAG AAA ACT CCC GTG AGT CCG GAA CCA GCT GTT ATA CCA CCT AAG    1735
Asp Lys Lys Thr Pro Val Ser Pro Glu Pro Ala Val Ile Pro Pro Lys
    500                 505                 510

AAG GTA CGC ATG GCC AAC TTG TGT GTT GTG GGC GGC CAT GCT GTT AAT    1783
Lys Val Arg Met Ala Asn Leu Cys Val Val Gly Gly His Ala Val Asn
515                 520                 525                 530

GGA GTT GCT GAG ATC CAT AGT GAA ATT GTG AAG GAG GAG GTT TTC AAT    1831
Gly Val Ala Glu Ile His Ser Glu Ile Val Lys Glu Glu Val Phe Asn
                535                 540                 545

GAC TTC TAT GAG CTC TGG CCG GAA AAG TTC CAA AAC AAA ACA AAT GGA    1879
Asp Phe Tyr Glu Leu Trp Pro Glu Lys Phe Gln Asn Lys Thr Asn Gly
            550                 555                 560

GTG ACT CCA AGA AGA TGG ATT CGT TTC TGC AAT CCT CCT CTT AGT GCC    1927
Val Thr Pro Arg Arg Trp Ile Arg Phe Cys Asn Pro Pro Leu Ser Ala
        565                 570                 575

ATC ATA ACT AAG TGG ACT GGT ACA GAG GAT TGG GTC CTG AAA ACT GAA    1975
Ile Ile Thr Lys Trp Thr Gly Thr Glu Asp Trp Val Leu Lys Thr Glu
    580                 585                 590

AAG TTG GCA GAA TTG CAG AAG TTT GCT GAT AAT GAA GAT CTT CAA AAT    2023
Lys Leu Ala Glu Leu Gln Lys Phe Ala Asp Asn Glu Asp Leu Gln Asn
595                 600                 605                 610

GAG TGG AGG GAA GCA AAA AGG AGC AAC AAG ATT AAA GTT GTC TCC TTT    2071
Glu Trp Arg Glu Ala Lys Arg Ser Asn Lys Ile Lys Val Val Ser Phe
                615                 620                 625

CTC AAA GAA AAG ACA GGG TAT TCT GTT GTC CCA GAT GCA ATG TTT GAT    2119
Leu Lys Glu Lys Thr Gly Tyr Ser Val Val Pro Asp Ala Met Phe Asp
            630                 635                 640

ATT CAG GTA AAA CGC ATT CAT GAG TAC AAG CGA CAA CTG TTA AAT ATC    2167
Ile Gln Val Lys Arg Ile His Glu Tyr Lys Arg Gln Leu Leu Asn Ile
```

```
                    645             650                 655
TTC GGC ATC GTT TAT CGG TAT AAG AAG ATG AAA GAA ATG ACA GCT GCA      2215
Phe Gly Ile Val Tyr Arg Tyr Lys Lys Met Lys Glu Met Thr Ala Ala
    660             665                 670

GAA AGA AAG ACT AAC TTC GTT CCT CGA GTA TGC ATA TTT GGG GGA AAA      2263
Glu Arg Lys Thr Asn Phe Val Pro Arg Val Cys Ile Phe Gly Gly Lys
675                 680                 685                 690

GCT TTT GCC ACA TAT GTG CAA GCC AAG AGG ATT GTA AAA TTT ATC ACA      2311
Ala Phe Ala Thr Tyr Val Gln Ala Lys Arg Ile Val Lys Phe Ile Thr
                695                 700                 705

GAT GTT GGT GCT ACT ATA AAT CAT GAT CCA GAA ATC GGT GAT CTG TTG      2359
Asp Val Gly Ala Thr Ile Asn His Asp Pro Glu Ile Gly Asp Leu Leu
            710                 715                 720

AAG GTA GTC TTT GTG CCA GAT TAC AAT GTC AGT GTT GCT GAA TTG CTA      2407
Lys Val Val Phe Val Pro Asp Tyr Asn Val Ser Val Ala Glu Leu Leu
        725                 730                 735

ATT CCT GCT AGC GAT CTA TCA GAA CAT ATC AGT ACG GCT GGA ATG GAG      2455
Ile Pro Ala Ser Asp Leu Ser Glu His Ile Ser Thr Ala Gly Met Glu
    740                 745                 750

GCC AGT GGA ACC AGT AAT ATG AAG TTT GCA ATG AAT GGT TGT ATC CAA      2503
Ala Ser Gly Thr Ser Asn Met Lys Phe Ala Met Asn Gly Cys Ile Gln
755                 760                 765                 770

ATT GGT ACA TTG GAT GGC GCT AAT GTT GAA ATA AGG GAA GAG GTT GGA      2551
Ile Gly Thr Leu Asp Gly Ala Asn Val Glu Ile Arg Glu Glu Val Gly
                775                 780                 785

GAA GAA AAC TTC TTT CTC TTT GGT GCT CAA GCT CAT GAA ATT GCA GGG      2599
Glu Glu Asn Phe Phe Leu Phe Gly Ala Gln Ala His Glu Ile Ala Gly
            790                 795                 800

CTT AGA AAA GAA AGA GCT GAC GGA AAG TTT GTA CCT GAT GAA CGT TTT      2647
Leu Arg Lys Glu Arg Ala Asp Gly Lys Phe Val Pro Asp Glu Arg Phe
        805                 810                 815

GAA GAG GTG AAG GAA TTT GTT AGA AGC GGT GCT TTT GGC TCT TAT AAC      2695
Glu Glu Val Lys Glu Phe Val Arg Ser Gly Ala Phe Gly Ser Tyr Asn
    820                 825                 830

TAT GAT GAC CTA ATT GGA TCG TTG GAA GGA AAT GAA GGT TTT GGC CGT      2743
Tyr Asp Asp Leu Ile Gly Ser Leu Glu Gly Asn Glu Gly Phe Gly Arg
835                 840                 845                 850

GCT GAC TAT TTC CTT GTG GGC AAG GAC TTC CCC AGT TAC ATA GAA TGC      2791
Ala Asp Tyr Phe Leu Val Gly Lys Asp Phe Pro Ser Tyr Ile Glu Cys
                855                 860                 865

CAA GAG AAA GTT GAT GAG GCA TAT CGC GAC CAG AAA AGG TGG ACA ACG      2839
Gln Glu Lys Val Asp Glu Ala Tyr Arg Asp Gln Lys Arg Trp Thr Thr
            870                 875                 880

ATG TCA ATC TTG AAT ACA GCG GGA TCG TAC AAG TTC AGC AGT GAC AGA      2887
Met Ser Ile Leu Asn Thr Ala Gly Ser Tyr Lys Phe Ser Ser Asp Arg
        885                 890                 895

ACA ATC CAT GAA TAT GCC AAA GAC ATT TGG AAC ATT GAA GCT GTG GAA      2935
Thr Ile His Glu Tyr Ala Lys Asp Ile Trp Asn Ile Glu Ala Val Glu
    900                 905                 910

ATA GCA TAA GAGGGGAAG TGAATGAAAA ATAACAAAGG CACAGTAAGT               2984
Ile Ala *
915

AGTTTCTCTT TTTATCATGT GATGAAGGTA TATAATGTAT GTGTAAGAGG ATGATGTTAT    3044

TACCACATAA TAAGAGATGA AGAGTCTCAT TTTGCTTCAA AAAAAAAAAA AAAAAAA       3101

(2) INFORMATION FOR SEQ ID NO:2:

(i) SEQUENCE CHARACTERISTICS:
        (A) LENGTH: 966 amino acids
        (B) TYPE: amino acid
```

(D) TOPOLOGY: linear (ii) MOLECULE TYPE: protein (xi) SEQUENCE DESCRIPTION: SEQ ID NO:2:

```
Met Ala Thr Ala Asn Gly Ala His Leu Phe Asn His Tyr Ser Ser Asn
-50                 -45                 -40                 -35

Ser Arg Phe Ile His Phe Thr Ser Arg Asn Thr Ser Ser Lys Leu Phe
                -30                 -25                 -20

Leu Thr Lys Thr Ser His Phe Arg Arg Pro Lys Arg Cys Phe His Val
            -15                 -10                  -5

Asn Asn Thr Leu Ser Glu Lys Ile His His Pro Ile Thr Glu Gln Gly
             1                   5                  10

Gly Glu Ser Asp Leu Ser Ser Phe Ala Pro Asp Ala Ala Ser Ile Thr
 15                  20                  25                  30

Ser Ser Ile Lys Tyr His Ala Glu Phe Thr Pro Val Phe Ser Pro Glu
                 35                  40                  45

Arg Phe Glu Leu Pro Lys Ala Phe Phe Ala Thr Ala Gln Ser Val Arg
                 50                  55                  60

Asp Ser Leu Leu Ile Asn Trp Asn Ala Thr Tyr Asp Ile Tyr Glu Lys
                 65                  70                  75

Leu Asn Met Lys Gln Ala Tyr Tyr Leu Ser Met Glu Phe Leu Gln Gly
 80                  85                  90

Arg Ala Leu Leu Asn Ala Ile Gly Asn Leu Glu Leu Thr Gly Ala Phe
 95                 100                 105                 110

Ala Glu Ala Leu Lys Asn Leu Gly His Asn Leu Glu Asn Val Ala Ser
                115                 120                 125

Gln Glu Pro Asp Ala Ala Leu Gly Asn Gly Leu Gly Arg Leu Ala
                130                 135                 140

Ser Cys Phe Leu Asp Ser Leu Ala Thr Leu Asn Tyr Pro Ala Trp Gly
                145                 150                 155

Tyr Gly Leu Arg Tyr Lys Tyr Gly Leu Phe Lys Gln Arg Ile Thr Lys
 160                 165                 170

Asp Gly Gln Glu Glu Val Ala Glu Asp Trp Leu Glu Ile Gly Ser Pro
175                 180                 185                 190

Trp Glu Val Val Arg Asn Asp Val Ser Tyr Pro Ile Lys Phe Tyr Gly
                195                 200                 205

Lys Val Ser Thr Gly Ser Asp Gly Lys Arg Tyr Trp Ile Gly Gly Glu
                210                 215                 220

Asp Ile Lys Ala Val Ala Tyr Asp Val Pro Ile Pro Gly Tyr Lys Thr
                225                 230                 235

Arg Thr Thr Ile Ser Leu Arg Leu Trp Ser Thr Gln Val Pro Ser Ala
240                 245                 250

Asp Phe Asp Leu Ser Ala Phe Asn Ala Gly Glu His Thr Lys Ala Cys
255                 260                 265                 270

Glu Ala Gln Ala Asn Ala Glu Lys Ile Cys Tyr Ile Leu Tyr Pro Gly
                275                 280                 285

Asp Glu Ser Glu Glu Gly Lys Ile Leu Arg Leu Lys Gln Gln Tyr Thr
                290                 295                 300

Leu Cys Ser Ala Ser Leu Gln Asp Ile Ile Ser Arg Phe Glu Arg Arg
                305                 310                 315

Ser Gly Asp Arg Ile Lys Trp Glu Glu Phe Pro Glu Lys Val Ala Val
                320                 325                 330

Gln Met Asn Asp Thr His Pro Thr Leu Cys Ile Pro Glu Leu Met Arg
335                 340                 345                 350
```

-continued

```
Ile Leu Ile Asp Leu Lys Gly Leu Asn Trp Asn Glu Ala Trp Asn Ile
            355                 360                 365

Thr Gln Arg Thr Val Ala Tyr Thr Asn His Thr Val Leu Pro Glu Ala
            370                 375                 380

Leu Glu Lys Trp Ser Tyr Glu Leu Met Gln Lys Leu Leu Pro Arg His
            385                 390                 395

Val Glu Ile Ile Glu Ala Ile Asp Glu Glu Leu Val His Glu Ile Val
            400                 405                 410

Leu Lys Tyr Gly Ser Met Asp Leu Asn Lys Leu Glu Lys Leu Thr
415                 420                 425                 430

Thr Met Arg Ile Leu Glu Asn Phe Asp Leu Pro Ser Ser Val Ala Glu
            435                 440                 445

Leu Phe Ile Lys Pro Glu Ile Ser Val Asp Asp Thr Glu Thr Val
            450                 455                 460

Glu Val His Asp Lys Val Glu Ala Ser Asp Lys Val Val Thr Asn Asp
            465                 470                 475

Glu Asp Asp Thr Gly Lys Lys Thr Ser Val Lys Ile Glu Ala Ala Ala
            480                 485                 490

Glu Lys Asp Ile Asp Lys Lys Thr Pro Val Ser Pro Glu Pro Ala Val
495                 500                 505                 510

Ile Pro Pro Lys Lys Val Arg Met Ala Asn Leu Cys Val Val Gly Gly
            515                 520                 525

His Ala Val Asn Gly Val Ala Glu Ile His Ser Glu Ile Val Lys Glu
            530                 535                 540

Glu Val Phe Asn Asp Phe Tyr Glu Leu Trp Pro Glu Lys Phe Gln Asn
            545                 550                 555

Lys Thr Asn Gly Val Thr Pro Arg Arg Trp Ile Arg Phe Cys Asn Pro
560                 565                 570

Pro Leu Ser Ala Ile Ile Thr Lys Trp Thr Gly Thr Glu Asp Trp Val
575                 580                 585                 590

Leu Lys Thr Glu Lys Leu Ala Glu Leu Gln Lys Phe Ala Asp Asn Glu
            595                 600                 605

Asp Leu Gln Asn Glu Trp Arg Glu Ala Lys Arg Ser Asn Lys Ile Lys
            610                 615                 620

Val Val Ser Phe Leu Lys Glu Lys Thr Gly Tyr Ser Val Pro Asp
            625                 630                 635

Ala Met Phe Asp Ile Gln Val Lys Arg Ile His Glu Tyr Lys Arg Gln
            640                 645                 650

Leu Leu Asn Ile Phe Gly Ile Val Tyr Arg Tyr Lys Lys Met Lys Glu
655                 660                 665                 670

Met Thr Ala Ala Glu Arg Lys Thr Asn Phe Val Pro Arg Val Cys Ile
            675                 680                 685

Phe Gly Gly Lys Ala Phe Ala Thr Tyr Val Gln Ala Lys Arg Ile Val
            690                 695                 700

Lys Phe Ile Thr Asp Val Gly Ala Thr Ile Asn His Asp Pro Glu Ile
            705                 710                 715

Gly Asp Leu Leu Lys Val Val Phe Val Pro Asp Tyr Asn Val Ser Val
            720                 725                 730

Ala Glu Leu Leu Ile Pro Ala Ser Asp Leu Ser Glu His Ile Ser Thr
735                 740                 745                 750

Ala Gly Met Glu Ala Ser Gly Thr Ser Asn Met Lys Phe Ala Met Asn
            755                 760                 765

Gly Cys Ile Gln Ile Gly Thr Leu Asp Gly Ala Asn Val Glu Ile Arg
```

-continued

```
                        770                 775                 780
Glu Glu Val Gly Glu Glu Asn Phe Phe Leu Phe Gly Ala Gln Ala His
                785                 790                 795
Glu Ile Ala Gly Leu Arg Lys Glu Arg Ala Asp Gly Lys Phe Val Pro
    800                 805                 810
Asp Glu Arg Phe Glu Glu Val Lys Glu Phe Val Arg Ser Gly Ala Phe
815                 820                 825                 830
Gly Ser Tyr Asn Tyr Asp Asp Leu Ile Gly Ser Leu Glu Gly Asn Glu
                835                 840                 845
Gly Phe Gly Arg Ala Asp Tyr Phe Leu Val Gly Lys Asp Phe Pro Ser
            850                 855                 860
Tyr Ile Glu Cys Gln Glu Lys Val Asp Glu Ala Tyr Arg Asp Gln Lys
                865                 870                 875
Arg Trp Thr Thr Met Ser Ile Leu Asn Thr Ala Gly Ser Tyr Lys Phe
            880                 885                 890
Ser Ser Asp Arg Thr Ile His Glu Tyr Ala Lys Asp Ile Trp Asn Ile
895                 900                 905                 910
Glu Ala Val Glu Ile Ala
                915
```

(2) INFORMATION FOR SEQ ID NO:3:

(i) SEQUENCE CHARACTERISTICS:
        (A) LENGTH: 2655 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Solanum tuberosum (ix) FEATURE:
        (A) NAME/KEY: CDS
        (B) LOCATION: 12..2528
        (D) OTHER INFORMATION: /product= "potato alpha-glucan
            H-type tuber phosphorylase"

(ix) FEATURE:
        (A) NAME/KEY: mat_peptide
        (B) LOCATION: 12..2525

(xi) SEQUENCE DESCRIPTION: SEQ ID NO:3:

```
GTTTATTTTC C ATG GAA GGT GGT GCA AAA TCG AAT GAT GTA TCA GCA GCA        50
             Met Glu Gly Gly Ala Lys Ser Asn Asp Val Ser Ala Ala
              1               5                  10

CCT ATT GCT CAA CCA CTT TCT GAA GAC CCT ACT GAC ATT GCA TCT AAT         98
Pro Ile Ala Gln Pro Leu Ser Glu Asp Pro Thr Asp Ile Ala Ser Asn
    15                  20                  25

ATC AAG TAT CAT GCT CAA TAT ACT CCT CAT TTT TCT CCT TTC AAG TTT        146
Ile Lys Tyr His Ala Gln Tyr Thr Pro His Phe Ser Pro Phe Lys Phe
30                  35                  40                  45

GAG CCA CTA CAA GCA TAC TAT GCT GCT ACT GCT GAC AGT GTT CGT GAT        194
Glu Pro Leu Gln Ala Tyr Tyr Ala Ala Thr Ala Asp Ser Val Arg Asp
                50                  55                  60

CGC TTG ATC AAA CAA TGG AAT GAC ACC TAT CTT CAT TAT GAC AAA GTT        242
Arg Leu Ile Lys Gln Trp Asn Asp Thr Tyr Leu His Tyr Asp Lys Val
            65                  70                  75

AAT CCA AAG CAA ACA TAC TAC TTA TCA ATG GAG TAT CTC CAG GGG CGA        290
```

-continued

```
        Asn Pro Lys Gln Thr Tyr Tyr Leu Ser Met Glu Tyr Leu Gln Gly Arg
                 80                  85                  90

GCT TTG ACA AAT GCA GTT GGA AAC TTA GAC ATC CAC AAT GCA TAT GCT         338
Ala Leu Thr Asn Ala Val Gly Asn Leu Asp Ile His Asn Ala Tyr Ala
         95                 100                 105

GAT GCT TTA AAC AAA CTG GGT CAG CAG CTT GAG GAG GTC GTT GAG CAG         386
Asp Ala Leu Asn Lys Leu Gly Gln Gln Leu Glu Glu Val Val Glu Gln
110                 115                 120                 125

GAA AAA GAT GCA GCA TTA GGA AAT GGT GGT TTA GGA AGG CTC GCT TCA         434
Glu Lys Asp Ala Ala Leu Gly Asn Gly Gly Leu Gly Arg Leu Ala Ser
                130                 135                 140

TGC TTT CTT GAT TCC ATG GCC ACA TTG AAC CTT CCA GCA TGG GGT TAT         482
Cys Phe Leu Asp Ser Met Ala Thr Leu Asn Leu Pro Ala Trp Gly Tyr
            145                 150                 155

GGC TTG AGG TAC AGA TAT GGA CTT TTT AAG CAG CTT ATC ACA AAG GCT         530
Gly Leu Arg Tyr Arg Tyr Gly Leu Phe Lys Gln Leu Ile Thr Lys Ala
        160                 165                 170

GGG CAA GAA GAA GTT CCT GAA GAT TGG TTG GAG AAA TTT AGT CCC TGG         578
Gly Gln Glu Glu Val Pro Glu Asp Trp Leu Glu Lys Phe Ser Pro Trp
    175                 180                 185

GAA ATT GTA AGG CAT GAT GTT GTC TTT CCT ATC AGG TTT TTT GGT CAT         626
Glu Ile Val Arg His Asp Val Val Phe Pro Ile Arg Phe Phe Gly His
190                 195                 200                 205

GTT GAA GTC CTC CCT TCT GGC TCG CGA AAA TGG GTT GGT GGA GAG GTC         674
Val Glu Val Leu Pro Ser Gly Ser Arg Lys Trp Val Gly Gly Glu Val
                210                 215                 220

CTA CAG GCT CTT GCA TAT GAT GTG CCA ATT CCA GGA TAC AGA ACT AAA         722
Leu Gln Ala Leu Ala Tyr Asp Val Pro Ile Pro Gly Tyr Arg Thr Lys
            225                 230                 235

AAC ACT AAT AGT CTT CGT CTC TGG GAA GCC AAA GCA AGC TCT GAG GAT         770
Asn Thr Asn Ser Leu Arg Leu Trp Glu Ala Lys Ala Ser Ser Glu Asp
        240                 245                 250

TTC AAC TTG TTT CTG TTT AAT GAT GGA CAG TAT GAT GCT GCT GCA CAG         818
Phe Asn Leu Phe Leu Phe Asn Asp Gly Gln Tyr Asp Ala Ala Ala Gln
    255                 260                 265

CTT CAT TCT AGG GCT CAG CAG ATT TGT GCT GTT CTC TAC CCT GGG GAT         866
Leu His Ser Arg Ala Gln Gln Ile Cys Ala Val Leu Tyr Pro Gly Asp
270                 275                 280                 285

GCT ACA GAG AAT GGA AAA CTC TTA CGG CTA AAG CAA CAA TTT TTT CTG         914
Ala Thr Glu Asn Gly Lys Leu Leu Arg Leu Lys Gln Gln Phe Phe Leu
                290                 295                 300

TGC AGT GCA TCG CTT CAG GAT ATT ATT GCC AGA TTC AAA GAG AGA GAA         962
Cys Ser Ala Ser Leu Gln Asp Ile Ile Ala Arg Phe Lys Glu Arg Glu
            305                 310                 315

GAT GGA AAG GGT TCT CAC CAG TGG TCT GAA TTC CCC AAG AAG GTT GCG        1010
Asp Gly Lys Gly Ser His Gln Trp Ser Glu Phe Pro Lys Lys Val Ala
        320                 325                 330

ATA CAA CTA AAT GAC ACA CAT CCA ACT CTT ACG ATT CCA GAG CTG ATG        1058
Ile Gln Leu Asn Asp Thr His Pro Thr Leu Thr Ile Pro Glu Leu Met
    335                 340                 345

CGG TTG CTA ATG GAT GAT GAA GGA CTT GGG TGG GAT GAA TCT TGG AAT        1106
Arg Leu Leu Met Asp Asp Glu Gly Leu Gly Trp Asp Glu Ser Trp Asn
350                 355                 360                 365

ATC ACT ACT AGG ACA ATT GCC TAT ACG AAT CAT ACA GTC CTA CCT GAA        1154
Ile Thr Thr Arg Thr Ile Ala Tyr Thr Asn His Thr Val Leu Pro Glu
                370                 375                 380

GCA CTT GAA AAA TGG TCT CAG GCA GTC ATG TGG AAG CTC CTT CCT AGA        1202
Ala Leu Glu Lys Trp Ser Gln Ala Val Met Trp Lys Leu Leu Pro Arg
            385                 390                 395

CAT ATG GAA ATC ATT GAA GAA ATT GAC AAA CGG TTT GTT GCT ACA ATA        1250
```

-continued

| | | |
|---|---|---|
| His Met Glu Ile Ile Glu Glu Ile Asp Lys Arg Phe Val Ala Thr Ile<br>400 405 410 | | |
| ATG TCA GAA AGA CCT GAT CTT GAG AAT AAG ATG CCT AGC ATG CGC ATT<br>Met Ser Glu Arg Pro Asp Leu Glu Asn Lys Met Pro Ser Met Arg Ile<br>415 420 425 | 1298 | |
| TTG GAT CAC AAC GCC ACA AAA CCT GTT GTG CAT ATG GCT AAC TTG TGT<br>Leu Asp His Asn Ala Thr Lys Pro Val Val His Met Ala Asn Leu Cys<br>430 435 440 445 | 1346 | |
| GTT GTC TCT TCA CAT ACG GTA AAT GGT GTT GCC CAG CTG CAT AGT GAC<br>Val Val Ser Ser His Thr Val Asn Gly Val Ala Gln Leu His Ser Asp<br>450 455 460 | 1394 | |
| ATC CTG AAG GCT GAG TTA TTT GCT GAT TAT GTC TCT GTA TGG CCC ACC<br>Ile Leu Lys Ala Glu Leu Phe Ala Asp Tyr Val Ser Val Trp Pro Thr<br>465 470 475 | 1442 | |
| AAG TTC CAG AAT AAG ACC AAT GGT ATA ACT CCT CGT AGG TGG ATC CGA<br>Lys Phe Gln Asn Lys Thr Asn Gly Ile Thr Pro Arg Arg Trp Ile Arg<br>480 485 490 | 1490 | |
| TTT TGT AGT CCT GAG CTG AGT CAT ATA ATT ACC AAG TGG TTA AAA ACA<br>Phe Cys Ser Pro Glu Leu Ser His Ile Ile Thr Lys Trp Leu Lys Thr<br>495 500 505 | 1538 | |
| GAT CAA TGG GTG ACG AAC CTC GAA CTG CTT GCT AAT CTT CGG GAG TTT<br>Asp Gln Trp Val Thr Asn Leu Glu Leu Leu Ala Asn Leu Arg Glu Phe<br>510 515 520 525 | 1586 | |
| GCT GAT AAT TCG GAG CTC CAT GCT GAA TGG GAA TCA GCC AAG ATG GCC<br>Ala Asp Asn Ser Glu Leu His Ala Glu Trp Glu Ser Ala Lys Met Ala<br>530 535 540 | 1634 | |
| AAC AAG CAG CGT TTG GCA CAG TAT ATA CTG CAT GTG ACA GGT GTG AGC<br>Asn Lys Gln Arg Leu Ala Gln Tyr Ile Leu His Val Thr Gly Val Ser<br>545 550 555 | 1682 | |
| ATC GAT CCA AAT TCC CTT TTT GAC ATA CAA GTC AAA CGT ATC CAT GAA<br>Ile Asp Pro Asn Ser Leu Phe Asp Ile Gln Val Lys Arg Ile His Glu<br>560 565 570 | 1730 | |
| TAC AAA AGG CAG CTT CTA AAT ATT CTG GGC GTC ATC TAT AGA TAC AAG<br>Tyr Lys Arg Gln Leu Leu Asn Ile Leu Gly Val Ile Tyr Arg Tyr Lys<br>575 580 585 | 1778 | |
| AAG CTT AAG GGA ATG AGC CCT GAA GAA AGG AAA AAT ACA ACT CCT CGC<br>Lys Leu Lys Gly Met Ser Pro Glu Glu Arg Lys Asn Thr Thr Pro Arg<br>590 595 600 605 | 1826 | |
| ACA GTC ATG ATT GGA GGA AAA GCA TTT GCA ACA TAC ACA AAT GCA AAA<br>Thr Val Met Ile Gly Gly Lys Ala Phe Ala Thr Tyr Thr Asn Ala Lys<br>610 615 620 | 1874 | |
| CGA ATT GTC AAG CTC GTG ACT GAT GTT GGC GAC GTT GTC AAT AGT GAC<br>Arg Ile Val Lys Leu Val Thr Asp Val Gly Asp Val Val Asn Ser Asp<br>625 630 635 | 1922 | |
| CCT GAC GTC AAT GAC TAT TTG AAG GTG GTT TTT GTT CCC AAC TAC AAT<br>Pro Asp Val Asn Asp Tyr Leu Lys Val Val Phe Val Pro Asn Tyr Asn<br>640 645 650 | 1970 | |
| GTA TCT GTG GCA GAG ATG CTT ATT CCG GGA AGT GAG CTA TCA CAA CAC<br>Val Ser Val Ala Glu Met Leu Ile Pro Gly Ser Glu Leu Ser Gln His<br>655 660 665 | 2018 | |
| ATC AGT ACT GCA GGC ATG GAA GCA AGT GGA ACA AGC AAC ATG AAA TTT<br>Ile Ser Thr Ala Gly Met Glu Ala Ser Gly Thr Ser Asn Met Lys Phe<br>670 675 680 685 | 2066 | |
| GCC CTT AAT GGA TGC CTT ATC ATT GGG ACA CTA GAT GGG GCC AAT GTG<br>Ala Leu Asn Gly Cys Leu Ile Ile Gly Thr Leu Asp Gly Ala Asn Val<br>690 695 700 | 2114 | |
| GAA ATT AGG GAG GAA ATT GGA GAA GAT AAC TTC TTT CTT TTT GGT GCA<br>Glu Ile Arg Glu Glu Ile Gly Glu Asp Asn Phe Phe Leu Phe Gly Ala<br>705 710 715 | 2162 | |
| ACA GCT GAT GAA GTT CCT CAA CTG CGC AAA GAT CGA GAG AAT GGA CTG | 2210 | |

```
Thr Ala Asp Glu Val Pro Gln Leu Arg Lys Asp Arg Glu Asn Gly Leu
            720                 725                 730

TTC AAA CCT GAT CCT CGG TTT GAA GAG GCA AAA CAA TTT ATT AGG TCT      2258
Phe Lys Pro Asp Pro Arg Phe Glu Glu Ala Lys Gln Phe Ile Arg Ser
        735                 740                 745

GGA GCA TTT GGG ACG TAT GAT TAT AAT CCC CTC CTT GAA TCA CTG GAA      2306
Gly Ala Phe Gly Thr Tyr Asp Tyr Asn Pro Leu Leu Glu Ser Leu Glu
750                 755                 760                 765

GGG AAC TCG GGA TAT GGT CGT GGA GAC TAT TTT CTT GTT GGT CAT GAT      2354
Gly Asn Ser Gly Tyr Gly Arg Gly Asp Tyr Phe Leu Val Gly His Asp
                770                 775                 780

TTT CCG AGC TAC ATG GAT GCT CAG GCA AGG GTT GAT GAA GCT TAC AAG      2402
Phe Pro Ser Tyr Met Asp Ala Gln Ala Arg Val Asp Glu Ala Tyr Lys
            785                 790                 795

GAC AGG AAA AGA TGG ATA AAG ATG TCT ATA CTG AGC ACT AGT GGG AGT      2450
Asp Arg Lys Arg Trp Ile Lys Met Ser Ile Leu Ser Thr Ser Gly Ser
        800                 805                 810

GGC AAA TTT AGT AGT GAC CGT ACA ATT TCT CAA TAT GCA AAA GAG ATC      2498
Gly Lys Phe Ser Ser Asp Arg Thr Ile Ser Gln Tyr Ala Lys Glu Ile
815                 820                 825

TGG AAC ATT GCC GAG TGT CGC GTG CCT TGA GCACACTTCT GAACCTGGTA        2548
Trp Asn Ile Ala Glu Cys Arg Val Pro *
830                 835

TCTAATAAGG ATCTAATGTT CATTGTTTAC TAGCATATGA ATAATGTAAG TTCAAGCACA    2608

ACATGCTTTC TTATTTCCTA CTGCTCTCAA GAAGCAGTTA TTTGTTG                  2655

(2) INFORMATION FOR SEQ ID NO:4:

(i) SEQUENCE CHARACTERISTICS:
        (A) LENGTH:  838 amino acids
        (B) TYPE: amino acid
        (D) TOPOLOGY: linear (ii) MOLECULE TYPE: protein (xi) SEQUENCE DESCRIPTION: SEQ ID NO:4:

Met Glu Gly Gly Ala Lys Ser Asn Asp Val Ser Ala Ala Pro Ile Ala
1                5                  10                  15

Gln Pro Leu Ser Glu Asp Pro Thr Asp Ile Ala Ser Asn Ile Lys Tyr
            20                  25                  30

His Ala Gln Tyr Thr Pro His Phe Ser Pro Phe Lys Phe Glu Pro Leu
        35                  40                  45

Gln Ala Tyr Tyr Ala Ala Thr Ala Asp Ser Val Arg Asp Arg Leu Ile
    50                  55                  60

Lys Gln Trp Asn Asp Thr Tyr Leu His Tyr Asp Lys Val Asn Pro Lys
65                  70                  75                  80

Gln Thr Tyr Tyr Leu Ser Met Glu Tyr Leu Gln Gly Arg Ala Leu Thr
                85                  90                  95

Asn Ala Val Gly Asn Leu Asp Ile His Asn Ala Tyr Ala Asp Ala Leu
            100                 105                 110

Asn Lys Leu Gly Gln Gln Leu Glu Glu Val Val Glu Gln Glu Lys Asp
        115                 120                 125

Ala Ala Leu Gly Asn Gly Gly Leu Gly Arg Leu Ala Ser Cys Phe Leu
    130                 135                 140

Asp Ser Met Ala Thr Leu Asn Leu Pro Ala Trp Gly Tyr Gly Leu Arg
145                 150                 155                 160

Tyr Arg Tyr Gly Leu Phe Lys Gln Leu Ile Thr Lys Ala Gly Gln Glu
                165                 170                 175
```

-continued

Glu Val Pro Glu Asp Trp Leu Glu Lys Phe Ser Pro Trp Glu Ile Val
            180                 185                 190

Arg His Asp Val Val Phe Pro Ile Arg Phe Phe Gly His Val Glu Val
            195                 200                 205

Leu Pro Ser Gly Ser Arg Lys Trp Val Gly Gly Glu Val Leu Gln Ala
            210                 215                 220

Leu Ala Tyr Asp Val Pro Ile Pro Gly Tyr Arg Thr Lys Asn Thr Asn
225                 230                 235                 240

Ser Leu Arg Leu Trp Glu Ala Lys Ala Ser Ser Glu Asp Phe Asn Leu
                245                 250                 255

Phe Leu Phe Asn Asp Gly Gln Tyr Asp Ala Ala Gln Leu His Ser
            260                 265                 270

Arg Ala Gln Gln Ile Cys Ala Val Leu Tyr Pro Gly Asp Ala Thr Glu
            275                 280                 285

Asn Gly Lys Leu Leu Arg Leu Lys Gln Gln Phe Phe Leu Cys Ser Ala
            290                 295                 300

Ser Leu Gln Asp Ile Ile Ala Arg Phe Lys Glu Arg Glu Asp Gly Lys
305                 310                 315                 320

Gly Ser His Gln Trp Ser Glu Phe Pro Lys Lys Val Ala Ile Gln Leu
            325                 330                 335

Asn Asp Thr His Pro Thr Leu Thr Ile Pro Glu Leu Met Arg Leu Leu
            340                 345                 350

Met Asp Asp Glu Gly Leu Gly Trp Asp Glu Ser Trp Asn Ile Thr Thr
            355                 360                 365

Arg Thr Ile Ala Tyr Thr Asn His Thr Val Leu Pro Glu Ala Leu Glu
            370                 375                 380

Lys Trp Ser Gln Ala Val Met Trp Lys Leu Leu Pro Arg His Met Glu
385                 390                 395                 400

Ile Ile Glu Glu Ile Asp Lys Arg Phe Val Ala Thr Ile Met Ser Glu
            405                 410                 415

Arg Pro Asp Leu Glu Asn Lys Met Pro Ser Met Arg Ile Leu Asp His
            420                 425                 430

Asn Ala Thr Lys Pro Val Val His Met Ala Asn Leu Cys Val Val Ser
            435                 440                 445

Ser His Thr Val Asn Gly Val Ala Gln Leu His Ser Asp Ile Leu Lys
            450                 455                 460

Ala Glu Leu Phe Ala Asp Tyr Val Ser Val Trp Pro Thr Lys Phe Gln
465                 470                 475                 480

Asn Lys Thr Asn Gly Ile Thr Pro Arg Arg Trp Ile Arg Phe Cys Ser
            485                 490                 495

Pro Glu Leu Ser His Ile Ile Thr Lys Trp Leu Lys Thr Asp Gln Trp
            500                 505                 510

Val Thr Asn Leu Glu Leu Leu Ala Asn Leu Arg Glu Phe Ala Asp Asn
            515                 520                 525

Ser Glu Leu His Ala Glu Trp Glu Ser Ala Lys Met Ala Asn Lys Gln
            530                 535                 540

Arg Leu Ala Gln Tyr Ile Leu His Val Thr Gly Val Ser Ile Asp Pro
545                 550                 555                 560

Asn Ser Leu Phe Asp Ile Gln Val Lys Arg Ile His Glu Tyr Lys Arg
            565                 570                 575

Gln Leu Leu Asn Ile Leu Gly Val Ile Tyr Arg Tyr Lys Lys Leu Lys
            580                 585                 590

Gly Met Ser Pro Glu Glu Arg Lys Asn Thr Thr Pro Arg Thr Val Met
            595                 600                 605

```
Ile Gly Gly Lys Ala Phe Ala Thr Tyr Thr Asn Ala Lys Arg Ile Val
    610                 615                 620
Lys Leu Val Thr Asp Val Gly Asp Val Val Asn Ser Asp Pro Asp Val
625                 630                 635                 640
Asn Asp Tyr Leu Lys Val Val Phe Val Pro Asn Tyr Asn Val Ser Val
                645                 650                 655
Ala Glu Met Leu Ile Pro Gly Ser Glu Leu Ser Gln His Ile Ser Thr
            660                 665                 670
Ala Gly Met Glu Ala Ser Gly Thr Ser Asn Met Lys Phe Ala Leu Asn
            675                 680                 685
Gly Cys Leu Ile Ile Gly Thr Leu Asp Gly Ala Asn Val Glu Ile Arg
    690                 695                 700
Glu Glu Ile Gly Glu Asp Asn Phe Phe Leu Phe Gly Ala Thr Ala Asp
705                 710                 715                 720
Glu Val Pro Gln Leu Arg Lys Asp Arg Glu Asn Gly Leu Phe Lys Pro
                725                 730                 735
Asp Pro Arg Phe Glu Glu Ala Lys Gln Phe Ile Arg Ser Gly Ala Phe
            740                 745                 750
Gly Thr Tyr Asp Tyr Asn Pro Leu Leu Glu Ser Leu Glu Gly Asn Ser
            755                 760                 765
Gly Tyr Gly Arg Gly Asp Tyr Phe Leu Val Gly His Asp Phe Pro Ser
770                 775                 780
Tyr Met Asp Ala Gln Ala Arg Val Asp Glu Ala Tyr Lys Asp Arg Lys
785                 790                 795                 800
Arg Trp Ile Lys Met Ser Ile Leu Ser Thr Ser Gly Ser Gly Lys Phe
                805                 810                 815
Ser Ser Asp Arg Thr Ile Ser Gln Tyr Ala Lys Glu Ile Trp Asn Ile
            820                 825                 830
Ala Glu Cys Arg Val Pro
            835
```

(2) INFORMATION FOR SEQ ID NO:5:

(i) SEQUENCE CHARACTERISTICS:
        (A) LENGTH: 3171 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Solanum tuberosum (ix) FEATURE:
        (A) NAME/KEY: CDS
        (B) LOCATION: 87..3011
        (D) OTHER INFORMATION: /product= "potato alpha-glucan
           L-type leaf phosphorylase"

(ix) FEATURE:
        (A) NAME/KEY: mat_peptide
        (B) LOCATION: 330..3008

(ix) FEATURE:
        (A) NAME/KEY: sig_peptide
        (B) LOCATION: 87..329

(xi) SEQUENCE DESCRIPTION: SEQ ID NO:5:

-continued

```
TTTTTTTTTT CAACATGCAC AACAATTATT TTGATTAAAT TTTGTATCTA AAAATTTAGC        60

ATTTTGAAAT TCAGTTCAGA GACATC ATG GCA ACT TTT GCT GTC TCT GGA TTG       113
                             Met Ala Thr Phe Ala Val Ser Gly Leu
                             -81 -80                 -75

AAC TCA ATT TCA AGT ATT TCT AGT TTT AAT AAC AAT TTC AGA AGC AAA        161
Asn Ser Ile Ser Ser Ile Ser Ser Phe Asn Asn Asn Phe Arg Ser Lys
    -70             -65                 -60

AAC TCA AAC ATT TTG TTG AGT AGA AGG AGG ATT TTA TTG TTC AGT TTT        209
Asn Ser Asn Ile Leu Leu Ser Arg Arg Arg Ile Leu Leu Phe Ser Phe
    -55             -50                 -45

AGA AGA AGA AGA AGA AGT TTC TCT GTT AGC AGT GTT GCT AGT GAT CAA        257
Arg Arg Arg Arg Arg Ser Phe Ser Val Ser Ser Val Ala Ser Asp Gln
-40             -35                 -30                 -25

AAG CAG AAG ACA AAG GAT TCT TCC TCT GAT GAA GGA TTT ACA TTA GAT        305
Lys Gln Lys Thr Lys Asp Ser Ser Ser Asp Glu Gly Phe Thr Leu Asp
            -20                 -15                 -10

GTT TTT CAG CCG GAC TCC ACG TCT GTT TTA TCA AGT ATA AAG TAT CAC        353
Val Phe Gln Pro Asp Ser Thr Ser Val Leu Ser Ser Ile Lys Tyr His
        -5                  1               5

GCT GAG TTC ACA CCA TCA TTT TCT CCT GAG AAG TTT GAA CTT CCC AAG        401
Ala Glu Phe Thr Pro Ser Phe Ser Pro Glu Lys Phe Glu Leu Pro Lys
10                  15                  20

GCA TAC TAT GCA ACT GCA GAG AGT GTT CGA GAT ACG CTC ATT ATA AAT        449
Ala Tyr Tyr Ala Thr Ala Glu Ser Val Arg Asp Thr Leu Ile Ile Asn
25                  30                  35                  40

TGG AAT GCC ACA TAC GAA TTC TAT GAA AAG ATG AAT GTA AAG CAG GCA        497
Trp Asn Ala Thr Tyr Glu Phe Tyr Glu Lys Met Asn Val Lys Gln Ala
                45                  50                  55

TAT TAC TTG TCT ATG GAA TTT CTT CAG GGA AGA GCT TTA CTC AAT GCT        545
Tyr Tyr Leu Ser Met Glu Phe Leu Gln Gly Arg Ala Leu Leu Asn Ala
                60                  65                  70

ATT GGT AAC TTG GGG CTA ACC GGA CCT TAT GCA GAT GCT TTA ACT AAG        593
Ile Gly Asn Leu Gly Leu Thr Gly Pro Tyr Ala Asp Ala Leu Thr Lys
            75                  80                  85

CTC GGA TAC AGT TTA GAG GAT GTA GCC AGG CAG GAA CCG GAT GCA GCT        641
Leu Gly Tyr Ser Leu Glu Asp Val Ala Arg Gln Glu Pro Asp Ala Ala
        90                  95                  100

TTA GGT AAT GGA GGT TTA GGA AGA CTT GCT TCT TGC TTT CTG GAC TCA        689
Leu Gly Asn Gly Gly Leu Gly Arg Leu Ala Ser Cys Phe Leu Asp Ser
105                 110                 115                 120

ATG GCG ACA CTA AAC TAC CCT GCA TGG GGC TAT GGA CTT AGA TAC CAA        737
Met Ala Thr Leu Asn Tyr Pro Ala Trp Gly Tyr Gly Leu Arg Tyr Gln
                125                 130                 135

TAT GGC CTT TTC AAA CAG CTT ATT ACA AAA GAT GGA CAG GAG GAA GTT        785
Tyr Gly Leu Phe Lys Gln Leu Ile Thr Lys Asp Gly Gln Glu Glu Val
            140                 145                 150

GCT GAA AAT TGG CTC GAG ATG GGA AAT CCA TGG GAA ATT GTG AGG AAT        833
Ala Glu Asn Trp Leu Glu Met Gly Asn Pro Trp Glu Ile Val Arg Asn
        155                 160                 165

GAT ATT TCG TAT CCC GTA AAA TTC TAT GGG AAG GTC ATT GAA GGA GCT        881
Asp Ile Ser Tyr Pro Val Lys Phe Tyr Gly Lys Val Ile Glu Gly Ala
    170                 175                 180

GAT GGG AGG AAG GAA TGG GCT GGC GGA GAA GAT ATA ACT GCT GTT GCC        929
Asp Gly Arg Lys Glu Trp Ala Gly Gly Glu Asp Ile Thr Ala Val Ala
185                 190                 195                 200

TAT GAT GTC CCA ATA CCA GGA TAT AAA ACA AAA ACA ACG ATT AAC CTT        977
Tyr Asp Val Pro Ile Pro Gly Tyr Lys Thr Lys Thr Thr Ile Asn Leu
                205                 210                 215

CGA TTG TGG ACA ACA AAG CTA GCT GCA GAA GCT TTT GAT TTA TAT GCT       1025
Arg Leu Trp Thr Thr Lys Leu Ala Ala Glu Ala Phe Asp Leu Tyr Ala
```

-continued

```
                    220                     225                     230
TTT AAC AAT GGA GAC CAT GCC AAA GCA TAT GAG GCC CAG AAA AAG GCT    1073
Phe Asn Asn Gly Asp His Ala Lys Ala Tyr Glu Ala Gln Lys Lys Ala
            235                     240                     245

GAA AAG ATT TGC TAT GTC TTA TAT CCA GGT GAC GAA TCG CTT GAA GGA    1121
Glu Lys Ile Cys Tyr Val Leu Tyr Pro Gly Asp Glu Ser Leu Glu Gly
250                     255                     260

AAG ACG CTT AGG TTA AAG CAG CAA TAC ACA CTA TGT TCT GCT TCT CTT    1169
Lys Thr Leu Arg Leu Lys Gln Gln Tyr Thr Leu Cys Ser Ala Ser Leu
265                     270                     275                 280

CAG GAC ATT ATT GCA CGG TTC GAG AAG AGA TCA GGG AAT GCA GTA AAC    1217
Gln Asp Ile Ile Ala Arg Phe Glu Lys Arg Ser Gly Asn Ala Val Asn
                285                     290                     295

TGG GAT CAG TTC CCC GAA AAG GTT GCA GTA CAG ATG AAT GAC ACT CAT    1265
Trp Asp Gln Phe Pro Glu Lys Val Ala Val Gln Met Asn Asp Thr His
            300                     305                     310

CCA ACA CTT TGT ATA CCA GAA CTT TTA AGG ATA TTG ATG GAT GTT AAA    1313
Pro Thr Leu Cys Ile Pro Glu Leu Leu Arg Ile Leu Met Asp Val Lys
            315                     320                     325

GGT TTG AGC TGG AAG CAG GCA TGG GAA ATT ACT CAA AGA ACG GTC GCA    1361
Gly Leu Ser Trp Lys Gln Ala Trp Glu Ile Thr Gln Arg Thr Val Ala
330                     335                     340

TAC ACT AAC CAC ACT GTT CTA CCT GAG GCT CTT GAG AAA TGG AGC TTC    1409
Tyr Thr Asn His Thr Val Leu Pro Glu Ala Leu Glu Lys Trp Ser Phe
345                     350                     355                 360

ACA CTT CTT GGT GAA CTG CTT CCT CGG CAC GTG GAG ATC ATA GCA ATG    1457
Thr Leu Leu Gly Glu Leu Leu Pro Arg His Val Glu Ile Ile Ala Met
                365                     370                     375

ATA GAT GAG GAG CTC TTG CAT ACT ATA CTT GCT GAA TAT GGT ACT GAA    1505
Ile Asp Glu Glu Leu Leu His Thr Ile Leu Ala Glu Tyr Gly Thr Glu
            380                     385                     390

GAT CTT GAC TTG TTG CAA GAA AAG CTA AAC CAA ATG AGG ATT CTG GAT    1553
Asp Leu Asp Leu Leu Gln Glu Lys Leu Asn Gln Met Arg Ile Leu Asp
            395                     400                     405

AAT GTT GAA ATA CCA AGT TCT GTT TTG GAG TTG CTT ATA AAA GCC GAA    1601
Asn Val Glu Ile Pro Ser Ser Val Leu Glu Leu Leu Ile Lys Ala Glu
        410                     415                     420

GAA AGT GCT GCT GAT GTC GAA AAG GCA GCA GAT GAA GAA CAA GAA GAA    1649
Glu Ser Ala Ala Asp Val Glu Lys Ala Ala Asp Glu Glu Gln Glu Glu
425                     430                     435                 440

GAA GGT AAG GAT GAC AGT AAA GAT GAG GAA ACT GAG GCT GTA AAG GCA    1697
Glu Gly Lys Asp Asp Ser Lys Asp Glu Glu Thr Glu Ala Val Lys Ala
                445                     450                     455

GAA ACT ACG AAC GAA GAG GAG GAA ACT GAG GTT AAG AAG GTT GAG GTG    1745
Glu Thr Thr Asn Glu Glu Glu Glu Thr Glu Val Lys Lys Val Glu Val
            460                     465                     470

GAG GAT AGT CAA GCA AAA ATA AAA CGT ATA TTC GGG CCA CAT CCA AAT    1793
Glu Asp Ser Gln Ala Lys Ile Lys Arg Ile Phe Gly Pro His Pro Asn
            475                     480                     485

AAA CCA CAG GTG GTT CAC ATG GCA AAT CTA TGT GTA GTT AGC GGG CAT    1841
Lys Pro Gln Val Val His Met Ala Asn Leu Cys Val Val Ser Gly His
        490                     495                     500

GCA GTT AAC GGT GTT GCT GAG ATT CAT AGT GAA ATA GTT AAG GAT GAA    1889
Ala Val Asn Gly Val Ala Glu Ile His Ser Glu Ile Val Lys Asp Glu
505                     510                     515                 520

GTT TTC AAT GAA TTT TAC AAG TTA TGG CCA GAG AAA TTC CAA AAC AAG    1937
Val Phe Asn Glu Phe Tyr Lys Leu Trp Pro Glu Lys Phe Gln Asn Lys
                525                     530                     535

ACA AAT GGT GTG ACA CCA AGA AGA TGG CTA AGT TTC TGT AAT CCA GAG    1985
Thr Asn Gly Val Thr Pro Arg Arg Trp Leu Ser Phe Cys Asn Pro Glu
```

-continued

```
              540                   545                   550
TTG AGT GAA ATT ATA ACC AAG TGG ACA GGA TCT GAT GAT TGG TTA GTA          2033
Leu Ser Glu Ile Ile Thr Lys Trp Thr Gly Ser Asp Asp Trp Leu Val
        555                   560                   565

AAC ACT GAA AAA TTG GCA GAG CTT CGA AAG TTT GCT GAT AAC GAA GAA          2081
Asn Thr Glu Lys Leu Ala Glu Leu Arg Lys Phe Ala Asp Asn Glu Glu
        570                   575                   580

CTC CAG TCT GAG TGG AGG AAG GCA AAA GGA AAT AAC AAA ATG AAG ATT          2129
Leu Gln Ser Glu Trp Arg Lys Ala Lys Gly Asn Asn Lys Met Lys Ile
585                   590                   595                   600

GTC TCT CTC ATT AAA GAA AAA ACA GGA TAC GTG GTC AGT CCC GAT GCA          2177
Val Ser Leu Ile Lys Glu Lys Thr Gly Tyr Val Val Ser Pro Asp Ala
                605                   610                   615

ATG TTT GAT GTT CAG ATC AAG CGC ATC CAT GAG TAT AAA AGG CAG CTA          2225
Met Phe Asp Val Gln Ile Lys Arg Ile His Glu Tyr Lys Arg Gln Leu
                620                   625                   630

TTA AAT ATA TTT GGA ATC GTT TAT CGC TAT AAG AAG ATG AAA GAA ATG          2273
Leu Asn Ile Phe Gly Ile Val Tyr Arg Tyr Lys Lys Met Lys Glu Met
                635                   640                   645

AGC CCT GAA GAA CGA AAA GAA AAG TTT GTC CCT CGA GTT TGC ATA TTT          2321
Ser Pro Glu Glu Arg Lys Glu Lys Phe Val Pro Arg Val Cys Ile Phe
650                   655                   660

GGA GGA AAA GCA TTT GCT ACA TAT GTT CAG GCC AAG AGA ATT GTA AAA          2369
Gly Gly Lys Ala Phe Ala Thr Tyr Val Gln Ala Lys Arg Ile Val Lys
665                   670                   675                   680

TTT ATC ACT GAT GTA GGG GAA ACA GTC AAC CAT GAT CCC GAG ATT GGT          2417
Phe Ile Thr Asp Val Gly Glu Thr Val Asn His Asp Pro Glu Ile Gly
                685                   690                   695

GAT CTT TTG AAG GTT GTA TTT GTT CCT GAT TAC AAT GTC AGT GTA GCA          2465
Asp Leu Leu Lys Val Val Phe Val Pro Asp Tyr Asn Val Ser Val Ala
                700                   705                   710

GAA GTG CTA ATT CCT GGT AGT GAG TTG TCC CAG CAT ATT AGT ACT GCT          2513
Glu Val Leu Ile Pro Gly Ser Glu Leu Ser Gln His Ile Ser Thr Ala
                715                   720                   725

GGT ATG GAG GCT AGT GGA ACC AGC AAC ATG AAA TTT TCA ATG AAT GGC          2561
Gly Met Glu Ala Ser Gly Thr Ser Asn Met Lys Phe Ser Met Asn Gly
        730                   735                   740

TGC CTC CTC ATC GGG ACA TTA GAT GGT GCC AAT GTT GAG ATA AGA GAG          2609
Cys Leu Leu Ile Gly Thr Leu Asp Gly Ala Asn Val Glu Ile Arg Glu
745                   750                   755                   760

GAA GTT GGA GAG GAC AAT TTC TTT CTT TTC GGA GCT CAG GCT CAT GAA          2657
Glu Val Gly Glu Asp Asn Phe Phe Leu Phe Gly Ala Gln Ala His Glu
                765                   770                   775

ATT GCT GGC CTA CGA AAG GAA AGA GCC GAG GGA AAG TTT GTC CCG GAC          2705
Ile Ala Gly Leu Arg Lys Glu Arg Ala Glu Gly Lys Phe Val Pro Asp
        780                   785                   790

CCA AGA TTT GAA GAA GTA AAG GCG TTC ATT AGG ACA GGC GTC TTT GGC          2753
Pro Arg Phe Glu Glu Val Lys Ala Phe Ile Arg Thr Gly Val Phe Gly
        795                   800                   805

ACC TAC AAC TAT GAA GAA CTC ATG GGA TCC TTG GAA GGA AAC GAA GGC          2801
Thr Tyr Asn Tyr Glu Glu Leu Met Gly Ser Leu Glu Gly Asn Glu Gly
        810                   815                   820

TAT GGT CGT GCT GAC TAT TTT CTT GTA GGA AAG GAT TTC CCC GAT TAT          2849
Tyr Gly Arg Ala Asp Tyr Phe Leu Val Gly Lys Asp Phe Pro Asp Tyr
825                   830                   835                   840

ATA GAG TGC CAA GAT AAA GTT GAT GAA GCA TAT CGA GAC CAG AAG AAA          2897
Ile Glu Cys Gln Asp Lys Val Asp Glu Ala Tyr Arg Asp Gln Lys Lys
                845                   850                   855

TGG ACC AAA ATG TCG ATC TTA AAC ACA GCT GGA TCG TTC AAA TTT AGC          2945
Trp Thr Lys Met Ser Ile Leu Asn Thr Ala Gly Ser Phe Lys Phe Ser
```

```
                 860              865              870
AGT GAT CGA ACA ATT CAT CAA TAT GCA AGA GAT ATA TGG AGA ATT GAA      2993
Ser Asp Arg Thr Ile His Gln Tyr Ala Arg Asp Ile Trp Arg Ile Glu
        875                  880              885

CCT GTT GAA TTA CCT TAA AAGTTAGCCA GTTAAAGGAT GAAAGCCAAT             3041
Pro Val Glu Leu Pro  *
890

TTTTTCCCCC TGAGGTTCTC CCATACTGTT TATTAGTACA TATATTGTCA ATTGTTGCTA    3101

CTGAAATGAT AGAAGTTTTG AATATTTACT GTCAATAAAA TACAGTTGAT TCCATTTGAA    3161

AAAAAAAAAA                                                           3171

(2) INFORMATION FOR SEQ ID NO:6:

(i) SEQUENCE CHARACTERISTICS:
        (A) LENGTH:  974 amino acids
        (B) TYPE: amino acid
        (D) TOPOLOGY: linear (ii) MOLECULE TYPE: protein (xi) SEQUENCE DESCRIPTION: SEQ ID NO:6:

Met Ala Thr Phe Ala Val Ser Gly Leu Asn Ser Ile Ser Ser Ile Ser
-81 -80             -75                 -70

Ser Phe Asn Asn Asn Phe Arg Ser Lys Asn Ser Asn Ile Leu Leu Ser
-65                 -60                 -55                 -50

Arg Arg Arg Ile Leu Leu Phe Ser Phe Arg Arg Arg Arg Ser Phe
            -45                 -40                 -35

Ser Val Ser Ser Val Ala Ser Asp Gln Lys Gln Lys Thr Lys Asp Ser
            -30                 -25                 -20

Ser Ser Asp Glu Gly Phe Thr Leu Asp Val Phe Gln Pro Asp Ser Thr
        -15                 -10                 -5

Ser Val Leu Ser Ser Ile Lys Tyr His Ala Glu Phe Thr Pro Ser Phe
  1              5                  10                  15

Ser Pro Glu Lys Phe Glu Leu Pro Lys Ala Tyr Tyr Ala Thr Ala Glu
                20                  25                  30

Ser Val Arg Asp Thr Leu Ile Ile Asn Trp Asn Ala Thr Tyr Glu Phe
                35                  40                  45

Tyr Glu Lys Met Asn Val Lys Gln Ala Tyr Tyr Leu Ser Met Glu Phe
                50                  55                  60

Leu Gln Gly Arg Ala Leu Leu Asn Ala Ile Gly Asn Leu Gly Leu Thr
            65                  70                  75

Gly Pro Tyr Ala Asp Ala Leu Thr Lys Leu Gly Tyr Ser Leu Glu Asp
80                  85                  90                  95

Val Ala Arg Gln Glu Pro Asp Ala Ala Leu Gly Asn Gly Leu Gly
                100                 105                 110

Arg Leu Ala Ser Cys Phe Leu Asp Ser Met Ala Thr Leu Asn Tyr Pro
                115                 120                 125

Ala Trp Gly Tyr Gly Leu Arg Tyr Gln Tyr Gly Leu Phe Lys Gln Leu
            130                 135                 140

Ile Thr Lys Asp Gly Gln Glu Glu Val Ala Glu Asn Trp Leu Glu Met
            145                 150                 155

Gly Asn Pro Trp Glu Ile Val Arg Asn Asp Ile Ser Tyr Pro Val Lys
160                 165                 170                 175

Phe Tyr Gly Lys Val Ile Glu Gly Ala Asp Gly Arg Lys Glu Trp Ala
                180                 185                 190

Gly Gly Glu Asp Ile Thr Ala Val Ala Tyr Asp Val Pro Ile Pro Gly
```

```
                     195                 200                 205
Tyr Lys Thr Lys Thr Thr Ile Asn Leu Arg Leu Trp Thr Lys Leu
            210                 215                 220

Ala Ala Glu Ala Phe Asp Leu Tyr Ala Phe Asn Asn Gly Asp His Ala
225                 230                 235

Lys Ala Tyr Glu Ala Gln Lys Lys Ala Glu Lys Ile Cys Tyr Val Leu
240                 245                 250                 255

Tyr Pro Gly Asp Glu Ser Leu Glu Gly Lys Thr Leu Arg Leu Lys Gln
                260                 265                 270

Gln Tyr Thr Leu Cys Ser Ala Ser Leu Gln Asp Ile Ile Ala Arg Phe
            275                 280                 285

Glu Lys Arg Ser Gly Asn Ala Val Asn Trp Asp Gln Phe Pro Glu Lys
        290                 295                 300

Val Ala Val Gln Met Asn Asp Thr His Pro Thr Leu Cys Ile Pro Glu
305                 310                 315

Leu Leu Arg Ile Leu Met Asp Val Lys Gly Leu Ser Trp Lys Gln Ala
320                 325                 330                 335

Trp Glu Ile Thr Gln Arg Thr Val Ala Tyr Thr Asn His Thr Val Leu
                340                 345                 350

Pro Glu Ala Leu Glu Lys Trp Ser Phe Thr Leu Leu Gly Glu Leu Leu
            355                 360                 365

Pro Arg His Val Glu Ile Ile Ala Met Ile Asp Glu Glu Leu Leu His
        370                 375                 380

Thr Ile Leu Ala Glu Tyr Gly Thr Glu Asp Leu Asp Leu Leu Gln Glu
    385                 390                 395

Lys Leu Asn Gln Met Arg Ile Leu Asp Asn Val Glu Ile Pro Ser Ser
400                 405                 410                 415

Val Leu Glu Leu Leu Ile Lys Ala Glu Glu Ser Ala Ala Asp Val Glu
                420                 425                 430

Lys Ala Ala Asp Glu Glu Gln Glu Glu Gly Lys Asp Asp Ser Lys
            435                 440                 445

Asp Glu Glu Thr Glu Ala Val Lys Ala Glu Thr Thr Asn Glu Glu Glu
        450                 455                 460

Glu Thr Glu Val Lys Lys Val Glu Val Glu Asp Ser Gln Ala Lys Ile
    465                 470                 475

Lys Arg Ile Phe Gly Pro His Pro Asn Lys Pro Gln Val Val His Met
480                 485                 490                 495

Ala Asn Leu Cys Val Val Ser Gly His Ala Val Asn Gly Val Ala Glu
                500                 505                 510

Ile His Ser Glu Ile Val Lys Asp Glu Val Phe Asn Glu Phe Tyr Lys
            515                 520                 525

Leu Trp Pro Glu Lys Phe Gln Asn Lys Thr Asn Gly Val Thr Pro Arg
        530                 535                 540

Arg Trp Leu Ser Phe Cys Asn Pro Glu Leu Ser Glu Ile Ile Thr Lys
    545                 550                 555

Trp Thr Gly Ser Asp Asp Trp Leu Val Asn Thr Glu Lys Leu Ala Glu
560                 565                 570                 575

Leu Arg Lys Phe Ala Asp Asn Glu Glu Leu Gln Ser Glu Trp Arg Lys
                580                 585                 590

Ala Lys Gly Asn Asn Lys Met Lys Ile Val Ser Leu Ile Lys Glu Lys
            595                 600                 605

Thr Gly Tyr Val Val Ser Pro Asp Ala Met Phe Asp Val Gln Ile Lys
        610                 615                 620
```

```
Arg Ile His Glu Tyr Lys Arg Gln Leu Leu Asn Ile Phe Gly Ile Val
    625                 630                 635

Tyr Arg Tyr Lys Lys Met Lys Glu Met Ser Pro Glu Arg Lys Glu
640                 645                 650                 655

Lys Phe Val Pro Arg Val Cys Ile Phe Gly Gly Lys Ala Phe Ala Thr
                660                 665                 670

Tyr Val Gln Ala Lys Arg Ile Val Lys Phe Ile Thr Asp Val Gly Glu
                675                 680                 685

Thr Val Asn His Asp Pro Glu Ile Gly Asp Leu Leu Lys Val Val Phe
                690                 695                 700

Val Pro Asp Tyr Asn Val Ser Val Ala Glu Val Leu Ile Pro Gly Ser
    705                 710                 715

Glu Leu Ser Gln His Ile Ser Thr Ala Gly Met Glu Ala Ser Gly Thr
720                 725                 730                 735

Ser Asn Met Lys Phe Ser Met Asn Gly Cys Leu Leu Ile Gly Thr Leu
                740                 745                 750

Asp Gly Ala Asn Val Glu Ile Arg Glu Val Gly Glu Asp Asn Phe
                755                 760                 765

Phe Leu Phe Gly Ala Gln Ala His Glu Ile Ala Gly Leu Arg Lys Glu
    770                 775                 780

Arg Ala Glu Gly Lys Phe Val Pro Asp Pro Arg Phe Glu Glu Val Lys
785                 790                 795

Ala Phe Ile Arg Thr Gly Val Phe Gly Thr Tyr Asn Tyr Glu Glu Leu
800                 805                 810                 815

Met Gly Ser Leu Glu Gly Asn Glu Gly Tyr Gly Arg Ala Asp Tyr Phe
                820                 825                 830

Leu Val Gly Lys Asp Phe Pro Asp Tyr Ile Glu Cys Gln Asp Lys Val
                835                 840                 845

Asp Glu Ala Tyr Arg Asp Gln Lys Lys Trp Thr Lys Met Ser Ile Leu
    850                 855                 860

Asn Thr Ala Gly Ser Phe Lys Phe Ser Ser Asp Arg Thr Ile His Gln
865                 870                 875

Tyr Ala Arg Asp Ile Trp Arg Ile Glu Pro Val Glu Leu Pro
880                 885                 890
```

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: internal (vi) ORIGINAL SOURCE:
        (A) ORGANISM: Solanum tuberosum (ix) FEATURE:
        (A) NAME/KEY: misc_feature
        (B) LOCATION: 1..27
        (D) OTHER INFORMATION: /function= "primer"
           /label= SPL1

(xi) SEQUENCE DESCRIPTION: SEQ ID NO:7:

ATTCGAAAAG CTCGAGATTT GCATAGA                          27

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: internal (vi) ORIGINAL SOURCE:
        (A) ORGANISM: Solanum tuberosum (ix) FEATURE:
        (A) NAME/KEY: misc_feature
        (B) LOCATION: 1..27
        (D) OTHER INFORMATION: /function= "primer"
            /label= SPL2

(xi) SEQUENCE DESCRIPTION: SEQ ID NO:8:

GTTTATTTTC CATCGATGGA AGGTGGT            27

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: internal (vi) ORIGINAL SOURCE:
        (A) ORGANISM: Solanum tuberosum (ix) FEATURE:
        (A) NAME/KEY: misc_feature
        (B) LOCATION: 1..23
        (D) OTHER INFORMATION: /function= "primer"
            /label= SPH1

(xi) SEQUENCE DESCRIPTION: SEQ ID NO:9:

GTGTGCTCTC GAGCATTGAA AGC                23

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: internal (vi) ORIGINAL SOURCE:
        (A) ORGANISM: Solanum tuberosum

```
(ix) FEATURE:
    (A) NAME/KEY: misc_feature
    (B) LOCATION: 1..25
    (D) OTHER INFORMATION: /function= "primer"
        /label= SPH2

(xi) SEQUENCE DESCRIPTION: SEQ ID NO:10:

ATAATATCCT GAATCGATGC ACTGC                                                 25
```

POTATOES HAVING IMPROVED QUALITY CHARACTERISTICS AND METHODS FOR THEIR PRODUCTION

This application claims the benefit of U.S. Provisional Patent Application No. 60/036,946, filed Feb. 10, 1997, which is incorporated in its entirety by reference herein.

FIELD OF THE INVENTION

The invention relates to the inhibition of the accumulation of sugars in potatoes by reducing the level of α glucan L-type tuber phosphorylase or α glucan H-type tuber phosphorylase enzyme activity in the potato plant.

BACKGROUND OF THE INVENTION

Plant stresses caused by a wide variety of factors including disease, environment, and storage of potato tubers (Solanum tuberosum) represent major determinants of tuber quality. Dormancy periods between harvesting and sprouting are critical to maintaining quality potatoes. Processing potatoes are usually stored between 7 and 12° C. Cold storage at 2 to 6° C., versus storage at 7 to 12° C., provides the greatest longevity by reducing respiration, moisture loss, microbial infection, heating costs, and the need for chemical sprout inhibitors (Burton, 1989). However, low temperatures lead to cold-induced sweetening, and the resulting high sugar levels contribute to an unacceptable brown or black color in the fried product (Coffin et al., 1987, Weaver et al., 1978). The sugars that accumulate are predominantly glucose, fructose, and sucrose. It is primarily the glucose and fructose (reducing sugars) that react with free amino groups when heated during the various cooking processes such as frying via the Maillard reaction, resulting in the formation of brown pigments (Burton, 1989, Shallenberger et al., 1959). Sucrose produces a black colouration when fried due to caramelization and charring. The ideal reducing sugar content is generally accepted to be 0.1% of tuber fresh weight with 0.33% as the upper limit and higher levels of reducing sugars are sufficient to cause the formation of brown and black pigments that results in an unacceptable fried product (Davies and Viola, 1992). Although the accumulation of reducing sugars can be slowed in higher temperature (7 to 12° C.) storage, this increases microbial infection and the need to use sprout inhibitors. Given the negative environmental and health risks associated with chemical use, development of pathogens resistant to pesticides, and the fact that use of current sprout inhibitors may soon be prohibited, a need exists for potato varieties that can withstand stress and long-term cold storage without the use of chemicals, without the accumulation of reducing sugars, and with greater retention of starch.

Carbohydrate metabolism is a complex process in plant cells. Manipulation of a number of different enzymatic processes may potentially affect the accumulation of reducing sugars during cold storage. For example, inhibition of starch breakdown would reduce the buildup of free sugar. Other methods may also serve to enhance the cold storage properties of potatoes through reduction of sugar content, including the resynthesis of starch using reducing sugars, removal of sugars through glycolysis and respiration, or conversion of sugars into other forms that would not participate in the Maillard reaction. However, many of the enzymatic processes are reversible, and the role of most of the enzymes involved in carbohydrate metabolism is poorly understood. The challenge remains to identify an enzyme that will deliver the desired result, achieve function at low temperatures, and still retain the product qualities desired by producers, processors, and consumers.

It has been suggested that phosphofructokinase (PFK) has an important role in the cold-induced sweetening process (Kruger and Hammond, 1988, ap Rees et al., 1988, Dixon et al., 1981, Claassen et al., 1991). ap Reese et al. (1988) suggested that cold treatment had a disproportionate effect on different pathways in carbohydrate metabolism in that glycolysis was more severely reduced due to the cold-sensitivity of PFK. The reduction in PFK activity would then lead to an increased availability of hexose-phosphates for sucrose production. It was disclosed in European Patent 0438904 (Burrell et al., Jul. 31, 1991) that increasing PFK activity reduces sugar accumulation during storage by removing hexoses through glycolysis and further metabolism. A PFK enzyme from E. coli was expressed in potato tubers and the report claimed to increase PFK activity and to reduce sucrose content in tubers assayed at harvest. However it has been shown that pyrophosphate:fructose 6-phosphate phosphotransferase (PFP) remains active at low temperatures (Claassen et al., 1991). PFP activity can supply fructose 6-phosphate for glycolysis just as PFK can, since the two enzymes catalyse the same reaction. Therefore, the efficacy of this strategy for improving cold storage quality of potato tubers remains in doubt. Furthermore, removal of sugars through glycolysis and further metabolism would not be a preferred method of enhancing storage properties of potato tubers because of the resultant loss of valuable dry matter through respiration.

It has also been suggested that ADPglucose pyrophosphorylase (ADPGPP) has an important role in the cold-induced sweetening process. It was disclosed in International Application WO 94/28149 (Barry, et al., filed May 18, 1994) that increasing ADPGPP activity reduces sugar accumulation during storage by re-synthesising starch using reducing sugars. An ADPGPP enzyme from E. coli was expressed in potato tubers under the control of a cold-induced promoter and the report claimed to increase ADPGPP activity and lower reducing sugar content in tubers assayed at harvest and after cold temperature storage. However, this strategy does not eliminate starch catabolism but instead increases the rate of starch resynthesis. Thus, catabolism of sugars through glycolysis and respiration occurs and re-incorporation into starch is limited. Up regulation of ADPGPP would not be a preferred method of enhancing storage properties of potato tubers because of the resultant loss of valuable dry matter through respiration. Again, a method involving the reduction of catabolism of starch would be preferable as dry matter would be retained.

The degradation of starch is believed to involve several enzymes including α-amylase (endoamylase), β-amylase (exoamylase), amyloglucosidase, and α-glucan phosphorylase (starch phosphorylase). By slowing starch catabolism, accumulation of reducing sugars should be prevented and the removal of sugars through glycolysis and further metabolism would be minimized.

Three different isozymes of α glucan phosphorylase have been described. The tuber L-type α1,4 glucan phosphorylase (EC 2.4.1.1) isozyme (GLTP) (Nakano and Fukui, 1986) has a low affinity for highly branched glucans, such as glycogen, and is localized in amyoplasts. The monomer consists of 916 amino acids and sequence comparisons with phosphorylases from rabbit muscle and Escherichia coli revealed a high level of homology, 51% and 40% amino acids, respectively. The nucleotide sequence of the GLTP gene and the amino acid sequence of the GLTP enzyme are shown in SEQ ID NO: 1 and SEQ ID NO: 2, respectively. The H-type tuber α-glucan phosphorylase isozyme H (GHTP) (Mori et al., 1991) has a high affinity for glycogen and is localized in the cytoplasm. The gene encodes for 838 amino acids and shows 63% sequence homology with the tuber L-type phosphorylase but lacks the 78-residue insertion and 50-residue amino-terminal extension found in the L-type polypeptide. The nucleotide sequence of the GHTP gene and the amino acid sequence of the GHTP enzyme are shown in SEQ ID NO: 3 and SEQ ID NO: 4, respectively. A third isozyme has been reported (Sonnewald et al., 1995) that consists of 974 amino acids and is highly homologous to the tuber L-type phosphorylase with 81% identity over most of the polypeptide. However, the regions containing the transit peptide and insertion sequence are highly diverse. This isozyme is referred to as the leaf L-type phosphorylase since the mRNA accumulates equally in leaf and tuber, whereas the mRNA of the tuber L-type phosphorylase accumulates strongly in potato tubers and only weakly in leaf tissues. The tuber L-type phosphorylase is mainly present in the tubers and the leaf L-type phosphorylase is more abundant in the leaves (Sonnewald et al., 1995). The nucleotide sequence of the leaf L-type phosphorylase gene and the amino acid sequence of the leaf L-type phosphorylase enzyme are shown in SEQ ID NO: 5 and SEQ ID NO: 6, respectively.

The role of the various starch degrading enzymes is not clear, however, and considerable debate has occurred over conflicting results. For example, reduced expression of the leaf L-type phosphorylase (Sonnewald et al., 1995) had no significant influence on starch accumulation. Sonnewald et al. (1995) reported that constitutive expression of an antisense RNA specific for the leaf L-type gene resulted in a strong reduction of α glucan phosphorylase L-type activity in leaf tissue, but had no effect in potato tuber tissue. Since the antisense repression of the α glucan phosphorylase activity had no significant influence on starch accumulation in leaves of transgenic potato plants, the authors concluded that starch breakdown was not catalysed by phosphorylases. Considering the high level of sequence homology between identified α glucan phosphorylase isozymes, a similar negative response would be expected with the H-type (GHTP) and L-type tuber (GLTP) isozymes.

In view of the foregoing, there remains a need for potato plants which produce tubers exhibiting reduced conversion of starches to sugars during propagation and during storage at ambient and reduced temperatures, particularly at temperatures below 7° C.

SUMMARY OF THE INVENTION

The inventors have found that surprisingly, reduction of the level of α glucan L-type tuber phosphorylase (GLTP) or α glucan H-type tuber phosphorylase (GHTP) enzyme activity within the potato tuber results in a substantial reduction in the accumulation of sugars in the tuber during propagation and storage, relative to wildtype potatoes, particularly at storage temperatures below 10° C., and specifically at 4° C. It is remarkable that, given the complexity of carbohydrate metabolism in the tuber, reduction in the activity of a single enzyme is effective in reducing sugar accumulation in the tuber. The inventors' discovery is even mere surprising in light of the previously discussed work of Sonnewald et al. (1995) wherein it was reported that reduced expression of the leaf L-type phosphorylase had no significant influence on starch accumulation in leaves of potato plants.

The present invention provides tremendous commercial advantages. Tubers in which cold-induced sweetening is inhibited or reduced may be stored at cooler temperatures without producing high levels of reducing sugars in the tuber which cause unacceptable darkening of fried potato products. Cold storage of tubers storage results in longer storage life, prolonged dormancy by limiting respiration and delaying sprouting, and lower incidence of disease.

Reduction in GLTP or GHTP activity in potato plants and tubers can be accomplished by any of a number of known methods, including, without limitation, antisense inhibition of GLTP or GHTP mRNA, co-suppression, site-directed mutagenesis of wildtype GLTP or GHTP genes, chemical or protein inhibition, or plant breeding programs.

Thus, in broad terms, the invention provides modified potato plants having a reduced level of α glucan L-type tuber phosphorylase (GLTP) or α glucan H-type tuber phosphorylase (GHTP) activity in tubers produced by the plants, relative to that of tubers produced by an unmodified potato plant. In a preferred embodiment, the invention provides a potato plant transformed with an expression cassette having a plant promoter sequence operably linked to a DNA sequence which, when transcribed in the plant, inhibits expression of an endogenous GLTP gene or GHTP gene. As will be discussed in detail hereinafter, the aforementioned DNA sequence may be inserted in the expression cassette in either a sense or antisense orientation. Potato plants of the present invention could have reduced activity levels of either one of GLTP or GHTP independently, or could have reduced activity levels of both GLTP and GHTP.

As discussed above, the inventors have found that reduction of activity levels of GLTP or GHTP enzymes in potato plants results in potato tubers in which sugar accumulation, particularly over long storage periods at temperatures below 10° C., is reduced. Therefore, the invention further extends to methods for reducing sugar production in tubers produced by a potato plant comprising reducing the level of activity of GLTP or GHTP in the potato plant. In a preferred embodiment, such methods involve introducing into the potato plant an expression cassette having a plant promoter sequence operably linked to a DNA sequence which, when transcribed in the plant, inhibits expression of an endogenous GLTP gene or GHTP gene. As above, the DNA sequence may be inserted in the expression cassette in either a sense or antisense orientation.

As described in detail in the examples herein, improvements in cold-storage characteristics have been observed in the potato variety Desiree transformed by the methods of the present invention. A direct measure of improved cold-storage characteristics is a reduction in the level of GLTP or GHTP enzyme activity detected in potatoes after harvest and cold-storage. Transformed potato varieties have been developed wherein the total α glucan phosphorylase activity measured as imol NADPH produced $mg^{-1}$ $protein^{-1}$ $h^{-1}$ in tubers of plants stored at 4° C. for 189 days is as much as 70% lower than the total α glucan phosphorylase activity in tubers of untransformed plants stored under the same conditions., Another relatively direct measure of improved cold-storage characteristics is a reduction in sweetening of potatoes observed after a period of cold-storage. Transformed potato varieties have been developed wherein the sum of the concentrations of glucose and fructose in tubers stored at 4° C. for 91 days is 39% lower than the sum of the concentrations of glucose and fructose in tubers of an untransformed plant stored under the same conditions.

Yet another measure of improved cold-storage characteristics, demonstrating a practical advantage of the present invention, is a reduction in darkening of a potato chip during processing (cooking). As discussed hereinbefore, the accumulation of sugars in potatoes during cold-storage contributes to unacceptable darkening of the fried product. Reduced darkening upon frying can be quantified as a measure of the reflectance, or chip score, of the fried potato chip. Techniques for measuring chip scores are discussed herein. Transformed potato varieties of the present invention have been developed wherein the chip score for tubers of plants stored at 4° C. for 124 days was as much as 89% higher than the chip scores for tubers of untransformed plants stored under the same conditions.

By reducing GLTP and/or GHTP activity in tubers of potato plants, thereby inhibiting sugar accumulation during cold-temperature storage, the present invention allows for storage of potatoes at cooler temperatures than would be possible with wildtype potatoes of the same cultivar. As discussed above, storage of potatoes at cooler temperatures than those traditionally used could result in increased storage life, increased dormancy through reduced respiration and sprouting, and reduced incidence of disease. It will be apparent to those skilled in the art that such additional benefits also constitute improved cold-storage characteristics and may be measured and quantified by known techniques.

BRIEF DESCRIPTION OF THE DRAWINGS

In drawings illustrating embodiments of the invention:

FIG. 5 is a comparison of the amino acid sequences of the three isoforms of phosphorylase found in potato for the region targeted by the antisense GLTP construct used in the Examples herein. Highlighted amino acids are identical. The leaf L-type α glucan phosphorylase amino acid sequence is on top (amino acids 21–238 of SEQ ID NO: 6), the tuber L-type α glucan phosphorylase amino acid sequence is in the middle (amino acids 49–266 of SEQ ID NO: 2), and tuber H-type α glucan phosphorylase amino acid sequence is on the bottom (amino acids 46–264 of SEQ ID NO: 4);

FIG. 6A and 6B are a comparison of the nucleotide sequences of the three isoforms of phosphorylase found in potato for the region targeted by the antisense GLTP construct used in the Examples herein. Highlighted nucleotides are identical. The leaf L-type α glucan phosphorylase nucleotide sequence is on top (nucleotides 389–1045 of SEQ ID NO: 5), the tuber L-type α glucan phosphorylase nucleotide sequence is in the middle (nucleotides 338–993 of SEQ ID NO: 1), and tuber H-type α glucan phosphorylase nucleotide sequence is on the bottom (nucleotides 147–805 of SEQ ID NO: 3);

Figure 8:
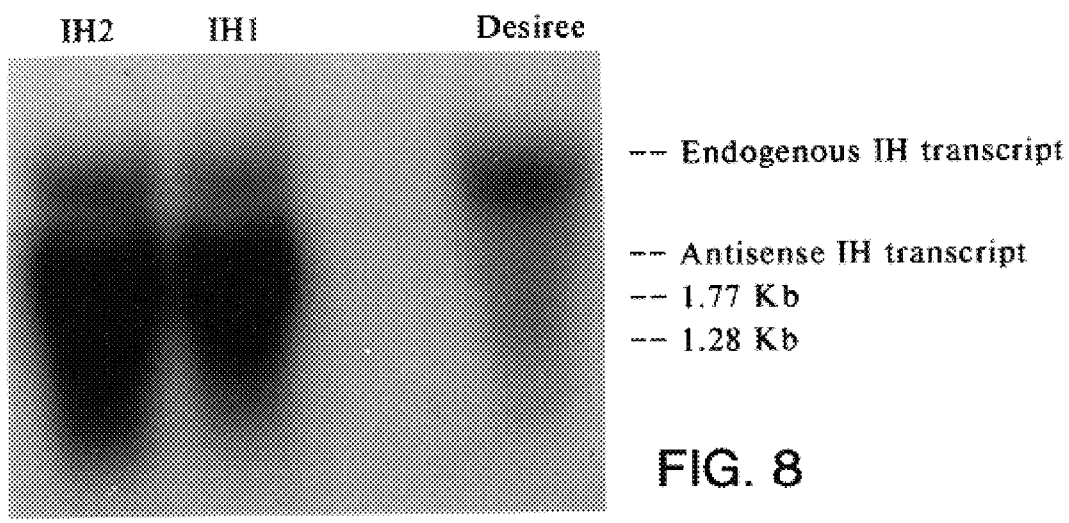
Figure 9:
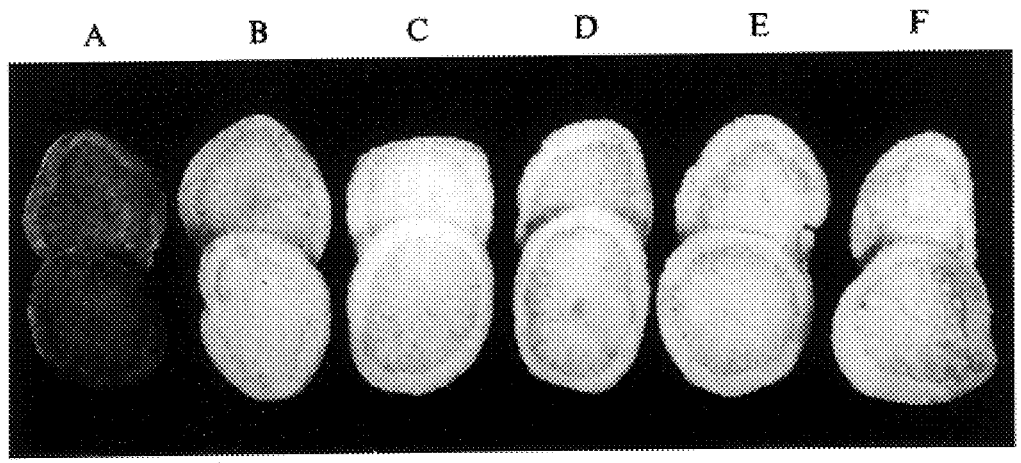
Figure 10:
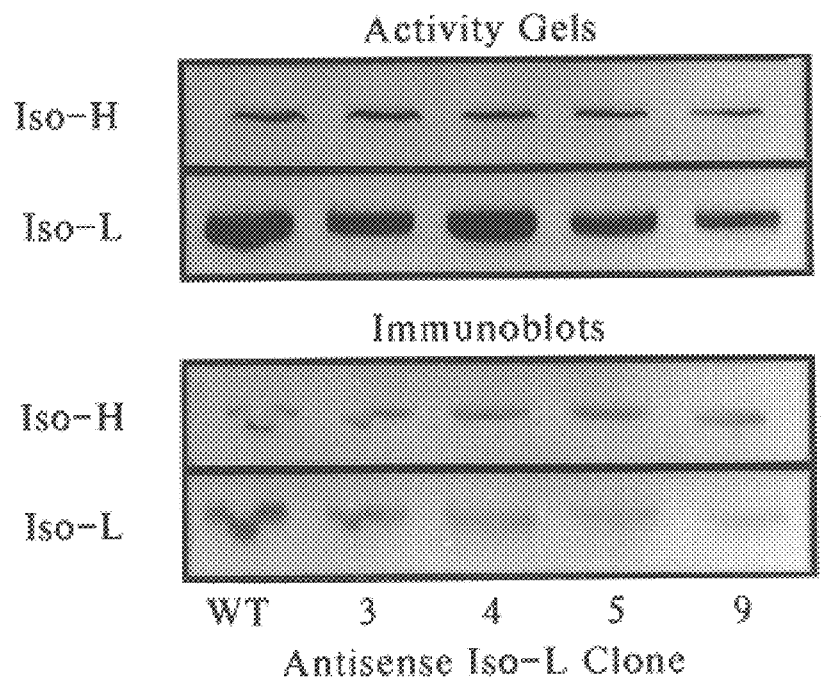
Figure 11:
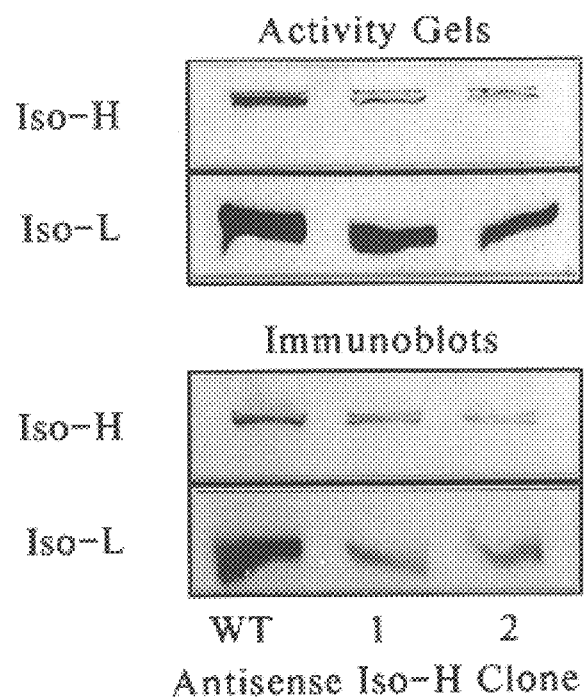

The blot was probed with a radiolabelled probe specific for the tuber L-type α glucan phosphorylase;

FIG. 8 is a northern blot of total RNA isolated from potato tubers of wild type and lines 1 and 2 transformed with the H-type α-glucan phosphorylase. The blot was probed with a radio labelled probe specific for the H-type α glucan phosphorylase;

FIG. 9 shows the fried product obtained from (A) wild type and tuber L-type α glucan phosphorylase transformants (B) ATL1 (C) ATL3 (D) ATL4 (E) ATL5 (F) ATL9 field grown tubers following 86 days storage at 4° C. ("ATL"= antisense tuber L-type transformant);

FIG. 10 shows the activity gel and western blot of L-type and H-type isozymes of α 1,4 glucan phosphorylase extracted from wild type tubers and tubers transformed with the antisense construct for the L-type isoform; and FIG. 11 shows the activity gel and western blot of L-type and H-type isozymes of α 1,4 glucan phosphorylase extracted from wild type tubers and transformed with the antisense construct for the H-type isoform.

DESCRIPTION OF THE PREFERRED EMBODIMENT

Potato plants having a reduced level of α glucan L-type tuber phosphorylase (GLTP) or α glucan H-type tuber phosphorylase (GHTP) activity in tubers produced by the plants relative to that of tubers produced by unmodified potato plants are provided. In the exemplified case, reduction in α glucan phosphorylase activity is accomplished by transforming a potato plant with an expression cassette having a plant promoter sequence operably linked to a DNA sequence which, when transcribed in the plant, inhibits expression of an endogenous GLTP gene or GHTP gene. Although, in the exemplified case, the DNA sequence is inserted in the expression cassette in the antisense orientation, a reduction in α glucan phosphorylase activity can be achieved with the DNA sequence inserted in the expression cassette in either a sense or antisense orientation.

1 Homology Dependent Silencing

The control of gene expression using sense or antisense gene fragments is standard laboratory practice and is well documented in the literature. Antisense and sense suppression are both gene sequence homology-dependent phenomena that may be described as "homology-dependent silencing" phenomena.

A review of scientific research articles published during 1996 reveals several hundred reports of homology-dependent silencing in transgenic plants. The mechanisms underlying homology-dependent silencing are not fully understood, but the characteristics of the phenomena have been studied in many plant genes and this body of work has been extensively reviewed (Meyer and Saedler 1996, Matzke and Matzke 1995, Jorgensen 1995, Weintraub 1990, Van der Krol et al. 1988) Homology-dependent silencing appears to be a general phenomenon that may be used to control the activity of many endogenous genes. Examples of genes exhibiting reduced expression after the introduction of homologous sequences include dihydroflavanol reductase (Van der Krol 1990), polygalacturonidase (Smith et al 1990), phytoene synthase (Fray and Grierson 1993), pectinesterase (Seymour et al. 1993), phenylalanine ammonia-lyase (De Carvalho et al. 1992), β-1,3-glucanase (Hart et al. 1992), chitinase (Dorlhac et al. 1994) nitrate reductase (Napoli et al. 1990), and chalcolne synthase (14). Transformation of Russet Burbank potato plants with either sense- or antisense-constructs of the potato leafroll virus coat protein gene has been reported to coinfer resistance to potato leafroll virus infection (Kawchuk et al. 1991). The transfer of a homologous sense or antisense sequence usually generates transformants with reduced endogenous gene expression. As discussed in detail in the examples herein, transformed potato plants exhibiting phenotypes indicating reduced GLTP or GHTP expression can be readily identified. In the antisense suppression technique, a gene construct or expression cassette is assembled which, when inserted into a plant cell, results in expression of an RNA which is of complementary sequence to the mRNA produced by the target gene. It is theorized that the complementary RNA sequences form a duplex thereby inhibiting translation to protein. The theory underlying both sense and antisense inhibition has been discussed in the literature, including in *Antisense Research and Applications* (CRC Press, 1993) pp. 125–148. The complementary sequence may be equivalent in length to the whole sequence of the target gene, but a fragment is usually sufficient and is more convenient to work with. For instance, Cannon et al. (1990) reveals that an antisense sequence as short as 41 base pairs is sufficient to achieve gene inhibition. U.S. Pat. No. 5,585,545 (Bennett et al., Dec. 17, 1996) describes gene inhibition by an antisense sequence of only 20 base pairs. There are many examples in the patent literature of patents including descriptions and claims to methods for suppressing gene expression through the introduction of antisense sequences to an organism, including, for example, U.S. Pat. No. 5,545,815 (Fischer et al., Aug. 13, 1996) and U.S. Pat. No. 5,387,757 (Bridges et al., Feb. 7, 1995).

Sense-sequence homology-dependent silencing is conducted in a similar manner to antisense suppression, except that the nucleotide sequence is inserted in the expression cassette in the normal sense orientation. A number of patents, including U.S. Pat. Nos. 5,034,323, 5,231,020 and 5,283,184, disclose the introduction of sense sequences leading to suppression of gene expression.

Both forms of homology-dependent silencing, sense- and antisense-suppression, are useful for accomplishing the down-regulation of GLTP or GHTP of the present invention. It is recognized in the art that both techniques are equally useful strategies for gene suppression. For instance, both U.S. Pat. No. 5,585,545 (Bennett et al., Dec. 17, 1996) and U.S. Pat. No. 5,451,514 (Boudet et al., Sep. 15, 1995) claim methods for inhibiting gene expression or recombinant DNA sequences useful in methods for suppressing gene expression drawn to both sense- and antisense-suppression techniques.

2 Alternate Techniques for Reducing GHTP and/or GLTP Activity in Tubers

Although homology-dependent silencing is a preferred technique for the down-regulation of GLTP or GHTP in potato plants of the present invention, there are several commonly used alternative strategies available to reduce the activity of a specific gene product which will be understood by those skilled in the art to bear application in the present invention. Insertion of a related gene or promoter into a plant can induce rapid turnover of homologous endogenous transcripts, a process referred to as co-suppression and believed to have many similarities to the mechanism responsible for antisense RNA inhibition (Jorgensen, 1995; Brusslan and Tobin, 1995). Various regulatory sequences of DNA can be altered (promoters, polyadenylation signals, post-transcriptional processing sites) or used to alter the expression levels (enhancers and silencers) of a specific MRNA. Another strategy to reduce expression of a gene and its encoded protein is the use of ribozymes designed to specifically cleave the target mRNA rendering it incapable of producing a fully functional protein (Hasseloff and Gerlach, 1988). Identification of naturally occurring alleles or the development of genetically engineered alleles of an enzyme that have been identified to be important in determining a particular trait can alter activity levels and be exploited by classical breeding programs (Oritz and Huaman, 1994). Site-directed mutagenesis is often used to modify the activity of an identified gene product. The structural coding sequence for a phosphorylase enzyme can be mutagenized in *E. coli* or another suitable host and screened for reduced starch phosphorolysis. Alternatively, naturally occurring alleles of the phosphorylase with reduced affinity and/or specific activity may be identified. Additionally, the activity of a particular enzyme can be altered using various inhibitors. These procedures are routinely used and can be found in text books such as Sambrook et al. (1989).

3 Variants of GLTP and GHTP Enzymes and Sequences Used for Homology Dependent Silencing As discussed in the background of the invention, and in greater detail by Nakano et al. (1986), Mori et al. (1991), and Sonnewald et al. (1990), there are three known α glucan phosphorylase isozymes that occur in potato plants. The present invention relates to down-regulation of the GLTP and/or GHTP isozymes. While it is believed that the GLTP and GHTP genes of all known commercial potato varieties are substantially identical, it is expected that the principles and techniques of the present invention would be effective in potato plants having variant full length polynucleotide sequences or subsequences which encode polypeptides having the starch catabolizing enzymatic activity of the described GLTP and GHTP enzymes. The terms "GLTP" and "GHTP", as used herein and in the claims, are intended to cover the variants described above. The foregoing variants may include GLTP and GHTP nucleotide sequence variants that differ from those exemplified but still encode the same polypeptide due to codon degeneracy, as well as variants which encode proteins capable of recognition by antibodies raised against the GLTP and GHTP amino acid sequences set forth in SEQ ID NO's. 2 and 4.

Similarly, those skilled in the art will recognize that homology dependent silencing of GLTP and/or GHTP in potato plants may be accomplished with sense or antisense sequences other than those exemplified. First, the region of the GLTP or GHTP cDNA sequence from which the antisense sequence is derived is not essential. Second, as described hereinabove, the length of the antisense sequence used may vary considerably. Further, the sense or antisense sequence need not be identical to that of the target GLTP or GHTP gene to be suppressed. As described in the Examples herein, the inventors have observed that transformation of potato plants with antisense DNA sequences derived from the GHTP gene not only substantially suppresses GHTP gene activity, but causes some degree of suppression of GLTP gene activity. The GHTP and GLTP genes antisense sequences have 56.8% sequence identity. The sequence identity between the GLTP antisense sequence and the corresponding leaf type α glucan phosphorylase squence described by Sonnewald et al. (1990) is 71.3%. In the inventors' research to date, the same phenomenon of cross-downregulation has not been observed when potato plants are transformed with antisense DNA sequences derived from the GLTP gene. Nevertheless, these results clearly indicate that absolute sequence identity between the target endogenous α glucan phosphorylase gene and the recombinant DNA is not essential given that GLTP activity was suppressed by an antisense sequence having about 57% sequence identity with the target GLTP sequence.

Thus, it will be understood by those skilled in the art that sense or antisense sequences other than those exemplified herein and other than those having absolute sequence identity with the target endogenous GLTP or GHTP gene will be effective to cause suppression of the endogenous GLTP or GHTP gene when introduced into potato plant cells. Useful sense or antisense sequences may differ from the exemplified antisense sequences or from other sequences derived from the endogenous GHTP or GLTP gene sequences by way of conservative amino acid substitutions or differences in the percentage of matched nucleotides or amino acids over portions of the sequences which are aligned for comparison purposes.

U.S. Pat. No. 5,585,545 (Bennett et al., Dec. 17, 1996) provides a helpful discussion regarding techniques for comparing sequence identity for polynucleotides and polypeptides, conservative amino acid substitutions, and hybridization conditions indicative of degrees of sequence identity. Relevant parts of that discussion are summarized herein.

Percentage of sequence identity for polynucleotides and polypeptides may be determined by comparing two optimally aligned sequences over a comparison window, wherein the portion of the polynucleotide or polypeptide sequence in the comparison window may include additions or deletions (i.e., gaps) as compared to the reference sequence (which does not comprise additions or deletions) for optimal alignment of the two sequences. The percentage is calculated by: (a) determining the number of positions at which the identical nucleic acid base or amino acid residue occurs in both sequences to yield the number of matched positions; (b) dividing the number of matched positions by the total number of positions in the window of comparison; and, (c) multiplying the result by 100 to yield the percentage of sequence identity. Optimal alignment of sequences for comparison may be conducted by computerized implementations of known algorithms (e.g., GAP, BESTFIT, FASTA, and TFASTA in the Wisconsin Genetics Software Package, Genetics Computer Group (GCG), 575 Science Dr., Madison, Wis., or BlastN and BlastX available from the National Center for Biotechnology Information), or by inspection.

Polypeptides which are substantially similar share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine.

Another indication that nucleotide sequences are substantially identical is if two molecules specifically hybridize to each other under stringent conditions. Stringent conditions are sequence dependent and will be different in different circumstances. Generally, stringent conditions are selected to be about 10° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. The $T_m$ of a hybrid, which is a function of both the length and the base composition of the probe, can be calculated as described in Sambrook et al. (1989). Typically, stringent conditions for a Southern blot protocol involve washing at 65° C. with 0.2×SSC. For preferred oligonucleotide probes, washing conditions are typically about at 42° C. in 6×SSC.

4 General Methods

Various methods are available to introduce and express foreign DNA sequences in plant cells. In brief, the steps involved in preparing antisense α glucan phosphorylase cDNAs and introducing them into a plant cell include: (1) isolating mRNA from potato plants and preparing cDNA from the mRNA; (2) screening the cDNA for the desired sequences; (3) linking a promoter to the desired cDNAs in the opposite orientation for expression of the phosphorylase genes; (4) transforming suitable host plant cells; and (5) selecting and regenerating cells which transcribe the inverted sequences.

In the exemplified case, DNA derived from potato GLTP and GHTP genes is used to create expression cassettes having a plant promoter sequence operably linked to an antisense DNA sequence which, when transcribed in the plant, inhibits expression of an endogenous GLTP gene or GHTP gene. *Agrobacterium tumefaciens* is used as a vehicle for transmission of the DNA to stem explants of potato plant shoots. A plant regenerated from the transformed explants transcribes the antisense DNA which inhibits activity of the enzyme.

The recombinant DNA technology described herein involves standard laboratory techniques that are well known in the art and are described in standard references such as Sambrook et al. (1989). Generally, enzymatic reactions involving DNA ligase, DNA polymerase, restriction endonucleases and the like are performed according to the manufacturer's specifications.

5 Preparation of GHTP and GLTP cDNA cDNA is prepared from isolated potato tuber mRNA by reverse transcription. A primer is annealed to the mRNA, providing a free 3' end that can be used for extension by the enzyme reverse transcriptase. The enzyme engages in the usual 5'-3' elongation, as directed by complementary base pairing with the mRNA template to form a hybrid molecule, consisting of a template RNA strand base-paired with the complementary cDNA strand. After degradation of the original mRNA, a DNA polymerase is used to synthesize the complementary DNA strand to convert the single-stranded cDNA into a duplex DNA.

After DNA amplification, the double stranded cDNA is inserted into a vector for propagation in *E. coli*. Typically, identification of clones harbouring the desired cDNA's would be performed by either nucleic acid hybridization or irmunological detection of the encoded protein, if an expression vector is used. In the exemplified case, the matter is simplified in that the DNA sequences of the GLTP and GHTP genes are known, as are the sequences of suitable primers (Brisson et al., 1990; Fukui et al., 1991). The primers used hybridize within the GLTP and GHTP genes. Thus, it is expected that the amplified cDNA's prepared represent portions of the GLTP and GHTP genes without further analysis. *E. coli* transformed with pUC19 plasmids carrying the phosphorylase DNA insert were detected by color selection. Appropriate *E. coli* strains transformed with plasmids which do not carry inserts grow as blue colonies. Strains transformed with pBluescript plasmids carrying inserts grow as white colonies. Plasmids isolated from transformed *E. coli* were sequenced to confirm the sequence of the phosphorylase inserts.

6 Vector Construction

The cDNAs prepared can be inserted in the antisense or sense orientation into expression cassette in expression vectors for transformation of potato plants to inhibit the expression of the GLTP and/or GHTP genes in potato tubers.

As in the exemplified case, which involves antisense suppression, the desired recombinant vector will comprise an expression cassette designed for initiating transcription of the antisense cDNAs in plants. Additional sequences are included to allow the vector to be cloned in a bacterial or phage host.

The vector will preferably contain a prokaryote origin of replication having a broad host range. A selectable marker should also be included to allow selection of bacterial cells bearing the desired construct. Suitable prokaryotic selectable markers include resistance to antibiotics such as ampicillin.

Other DNA sequences encoding additional functions may also be present in the vector, as is known in the art. For instance, in the case of Agrobacterium transformations, T-DNA sequences will also be included for subsequent transfer to plant chromosomes.

For expression in plants, the recombinant expression cassette will contain in addition to the desired sequence, a plant promoter region, a transcription initiation site (if the sequence to be transcribed lacks one), and a transcription termination sequence. Unique restriction enzyme sites at the 5' and 3' ends of the cassette are typically included to allow for easy insertion into a pre-existing vector. Sequences controlling eukaryotic gene expression are well known in the art.

Transcription of DNA into mRNA is regulated by a region of DNA referred to as the promoter. The promoter region contains sequence of bases that signals RNA polymerase to associate with the DNA, and to initiate the transcription of mRNA using one of the DNA strands as a template to make a corresponding complimentary strand of RNA. Promoter sequence elements include the TATA box consensus sequence (TATAAT), which is usually 20 to 30 base pairs (bp) upstream (by convention −30 to −20 bp relative to the transcription start site) of the transcription start site. In most instances the TATA box is required for accurate transcription initiation. The TATA box is the only upstream promoter element that has a relatively fixed location with respect to the start point.

The CAAT box consensus sequence is centered at −75, but can function at distances that vary considerably from the start point and in either orientation.

Another common promoter element is the GC box at −90 which contains the consensus sequence GGGCGG. It may occur in multiple copies and in either orientation.

Other sequences conferring tissue specificity, response to environmental signals, or maximum efficiency of transcription may also be found in the promoter region. Such sequences are often found within 400 bp of transcription initiation size, but may extend as far as 2000 bp or more. In heterologous promoter/structural gene combinations, the promoter is preferably positioned about the same distance from the heterologous transcription start site as it is from the transcription start site in its natural setting. However, some variation in this distance can be accommodated without loss of promoter function.

The particular promoter used in the expression cassette is not critical to the invention. Any of a number of promoters which direct transcription in plant cells is suitable. The promoter can be either constitutive or inducible.

A number of promoters which are active in plant cells have been described in the literature. These include the nopaline synthase (NOS) and octopine synthase (OCS) promoters (which are carried on tumour-inducing plasmids of *Agrobacterium tumefaciens*), the caulimovirus promoters such as the cauliflower mosaic virus (CaMV) 19S and 35S and the figwort mosaic virus 35S-promoters, the light-inducible promoter from the small subunit of ribulose-1,5-bis-phosphate carboxylase (ssRUBISCO, a very abundant plant polypeptide), and the chlorophyll a/b binding protein gene promoter, etc. All of these promoters have been used to create various types of DNA constructs which have been expressed in plants; see, e.g., PCT WO8402913.

The CaMV 35S promoter used in the Examples herein, has been shown to be highly active and constitutively expressed in most tissues (Bevan et al., 1986). A number of other genes with tuber-specific or enhanced expression are known, including the potato tuber ADPGPP genes, large and small subunits (Muller et al., 1990). Other promoters which are contemplated to be useful in this invention include those that show enhanced or specific expression in potato tubers, that are promoters normally associated with the expression of starch biosynthetic or modification enzyme genes, or that show different patterns of expression, for example, or are expressed at different times during tuber development. Examples of these promoters include those for the genes for the granule-bound and other starch synthases, the branching enzymes (Blennow et al., 1991; WO 9214827; WO 9211375), disproportionating enzyme (Takaha et al., 1993) debranching enzymes, amylases, starch phosphorylases (Nakano et al., 1989; Mori et al., 1991), pectin esterases (Ebbelaar et al., 1993), the 40 kD glycoprotein; ubiquitin, aspartic proteinase inhibitor (Stukerlj et al., 1990), the carboxypeptidase inhibitor, tuber polyphenol oxidases (Shahar et al., 1992; GenBank Accession Numbers M95196 and M95197), putative trypsin inhibitor and other tuber cDNAs (Stiekema et al., 1988), and for amylases and sporamins (Yoshida et al., 1992; Ohta et al., 1991).

In addition to a promoter sequence, the expression cassette should also contain a transcription termination region downstream of the structural gene to provide for efficient termination. The termination region may be obtained from the same gene as the promoter sequence or may be obtained from different genes. In the exemplified case the nopaline synthase NOS 3' terminator sequence (Bevan et al. 1983) was used.

Polyadenylation sequences are also commonly added to the vector construct if the mRNA encoded by the structural gene is to be efficiently translated (Alber and Kawasaki, 1982). Polyadenylation is believed to have an effect on stabilizing mRNAs. Polyadenylation sequences include, but are not limited to the Agrobacterium octopine synthase signal (Gielen et al., 1984) or the nopaline synthase signal (Depicker et al., 1982).

The vector will also typically contain a selectable marker gene by which transformed plant cells can be identified in culture. Typically, the marker gene encodes antibiotic resistance. These markers include resistance to G418, hygromycin, bleomycin, kanamycin, and gentamycin. In the exemplified case, the marker gene confers resistance to kanamycin. After transforming the plant cells, those cells containing the vector will be identified by their ability to grow in a medium containing the particular antibiotic.

7 Transformation of Plant Cells

Although in the exemplified case potato plant shoot stem explants were transformed via inoculation with *Agrobacterium tumefaciens* carrying the antisense sequence linked to a binary vector, direct transformation techniques which are known in the art can also be used to transfer the recombinant DNA. The vector can be microinjected directly into plant cells. Alternatively, nucleic acids may be introduced to the plant cell by high velocity ballistic penetration by small particles having the nucleic acid of interest embedded within the matrix of the particles or on the surface. Fusion of protoplasts with lipid-surfaced bodies such as minicells, cells or lysosomes carrying the DNA of interest can be used. The DNA may also be introduced into plant cells by electroporation, wherein plant protoplasts are electroporated in the presence of plasmids carrying the expression cassette.

In contrast to direct transformation methods, the exemplified case uses vectored transformation using *Agrobacterium tumefaciens*. *Agrobacterium tumefaciens* is a Gram-negative soil bacteria which causes a neoplastic disease known as crown gall in dicotyledonous plants. Induction of tumours is caused by tumour-inducing plasmids known as Ti plasmids. Ti plasmids direct the synthesis of opines in the infected plant. The opines are used as a source of carbon and/or nitrogen by the Agrobacteria.

The bacterium does not enter the plant cell, but transfers only part of the Ti plasmid, a portion called T-DNA, which is stably integrated into the plant genome, where it expresses the functions needed to synthesize opines and to transform the plant cell. Vir (virulence) genes on the Ti plasmid, outside of the T-DNA region, are necessary for the transfer of the T-DNA. The vir region, however, is not transferred. In fact, the vir region, although required for T-DNA transfer, need not be physically linked to the T-DNA and may be provided on a separate plasmid.

The tumour-inducing portions of the T-DNA can be interrupted or deleted without loss of the transfer and integration functions, such that normal and healthy transformed plant cells may be produced which have lost all properties of tumour cells, but still harbour and express certain parts of T-DNA, particularly the T-DNA border regions. Therefore, modifieds Ti plasmids, in which the disease causing genes have been deleted, may be used as vectors for the transfer of the sense and antisense gene constructs of the present invention into potato plants (see generally Winnacker, 1987).

Transformation of plants cells with Agrobacterium and regeneration of whole plants typically involves either co-cultivation of Agrobacterium with cultured isolated protoplasts or transformation of intact cells or tissues with Agrobacterium. In the exemplified case, stem explants from potato shoot cultures are transformed with Agrobacterium.

Alternatively, cauliflower mosaic virus (CaMV) may be used as a vector for introducing sense or antisense DNA into plants of the Solanaceae family. For instance, U.S. Pat. No. 4,407,956 (Howell, Oct. 4, 1983) teaches the use of cauliflower mosaic virus DNA as a plant vehicle.

8 Selection and Regeneration of Transformed Plant Cells

After transformation, transformed plant cells or plants carrying the antisense or sense DNA must be identified. A selectable marker, such as antibiotic resistance, is typically used. In the exemplified case, transformed plant cells were selected by growing the cells on growth medium containing kanamycin. Other selectable markers will be apparent to those skilled in the art. For instance, the presence of opines can be used to identify transformants if the plants are transformed with Agrobacterium.

Expression of the foreign DNA can be confirmed by detection of RNA encoded by the inserted DNA using well known methods such as Northern blot hybridization. The inserted DNA sequence can itself be identified by Southern blot hybridization or the polymerase chain reaction, as well (See, generally, Sambrook et al. (1989)).

Generally, after it is determined that the transformed plant cells carry the recombinant DNA, whole plants are regenerated. In the exemplified case, stem and leaf explants of potato shoot cultures were inoculated with a culture of *Agrobacterium tumefaciens* carrying the desired antisense DNA and a kanamycin marker gene. Transformants were selected on a kanamycin-containing growth medium. After transfer to a suitable medium for shoot induction, shoots were transferred to a medium suitable for rooting. Plants were then transferred to soil and hardened off. The plants regenerated in culture were transplanted and grown to maturity under greenhouse conditions.

9 Analysis of GHTP and GLTP Activity Levels in Transformed Tubers

Figure 1:
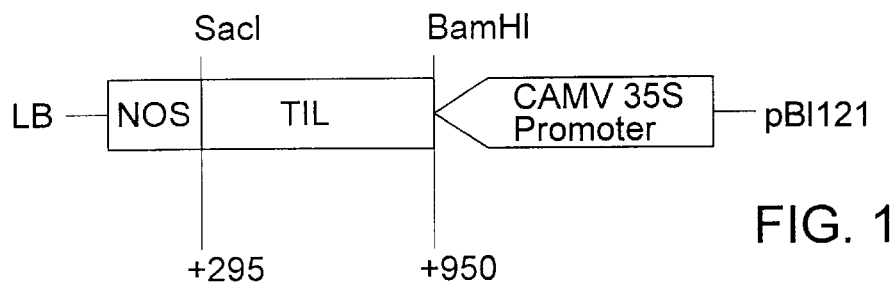
FIG. 1 is a schematic diagram of the tuber L-type α glucan phosphorylase antisense sequence inserted into the pBI121 transformation vector.
Figure 2:
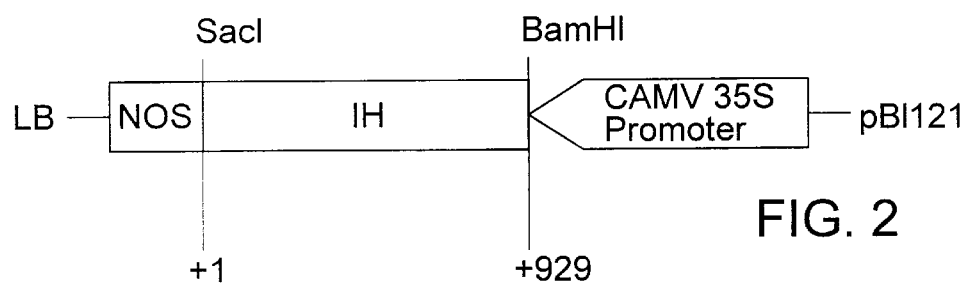
FIG. 2 is a schematic diagram of the tuber H-type α glucan phosphorylase antisense sequence inserted into the pBI121 transformation vector.
Figure 3:
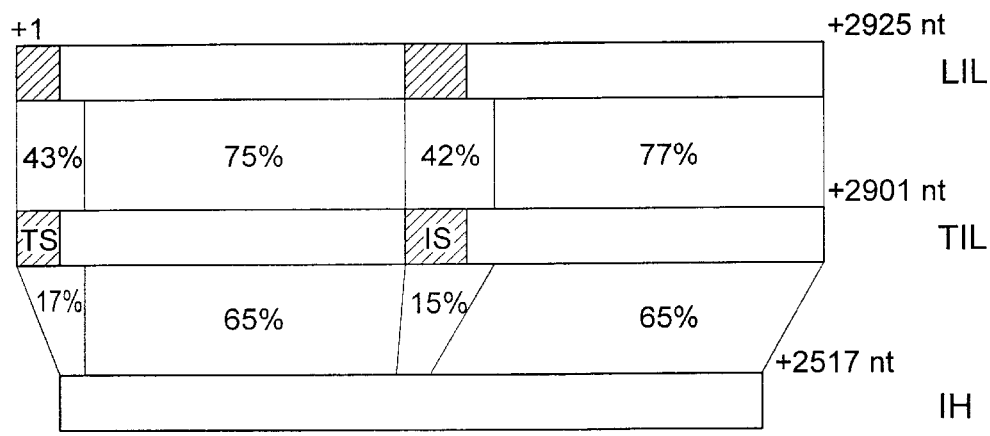
FIG. 3 shows the basic structure of the three isolated isoforms of glucan phosphorylase. The transit peptide (TS) and insertion sequence (IS) are characteristic of the L-type phosphorylases and are not found in the H-type phosphorylase. The percentages indicate the nucleic acid sequence homologies between the isoforms.
Figure 4:
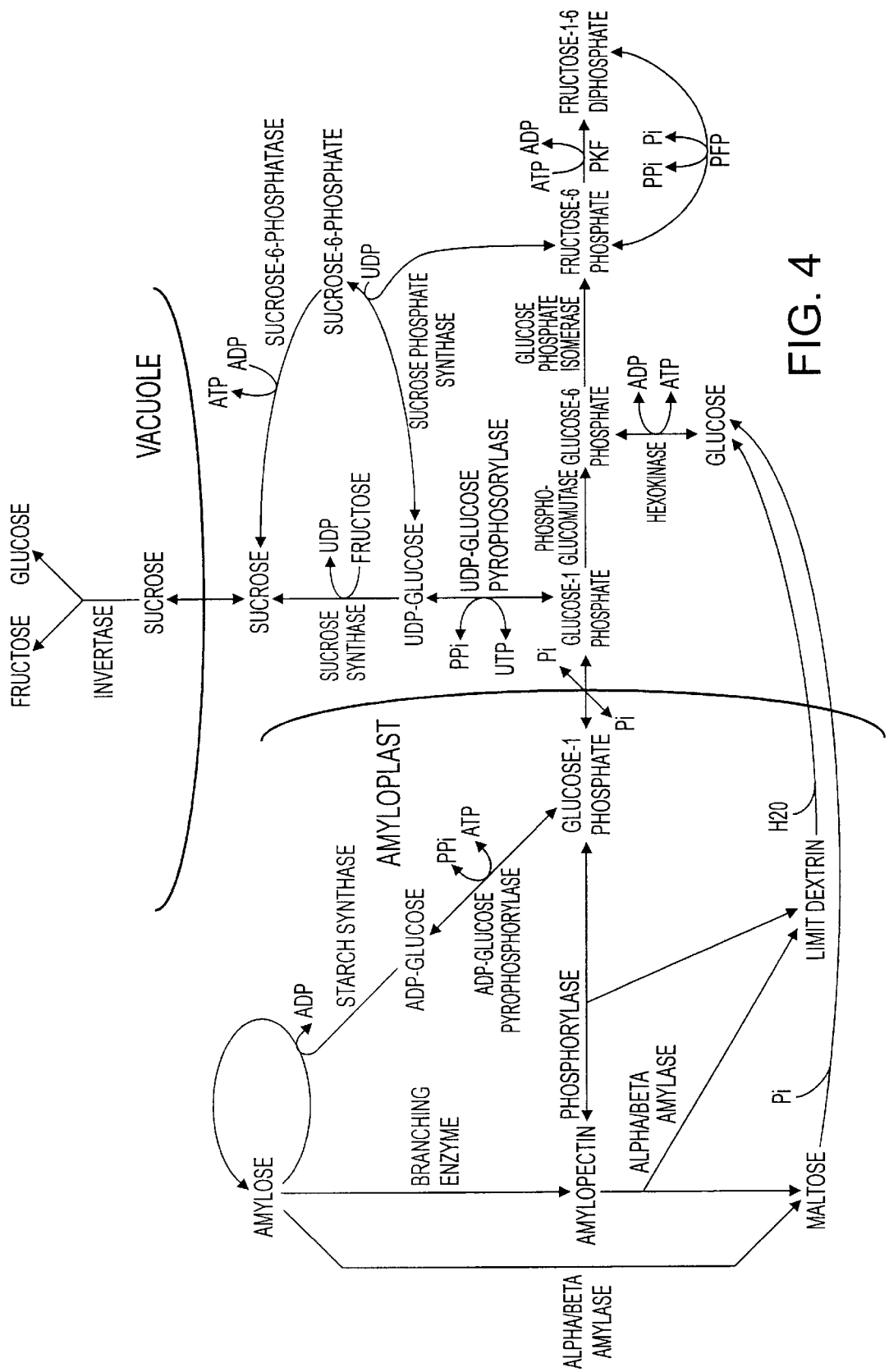
FIG. 4 is a schematic diagram of carbohydrate interconversions in potatoes (Sowokinos 1990)
Figure 7:
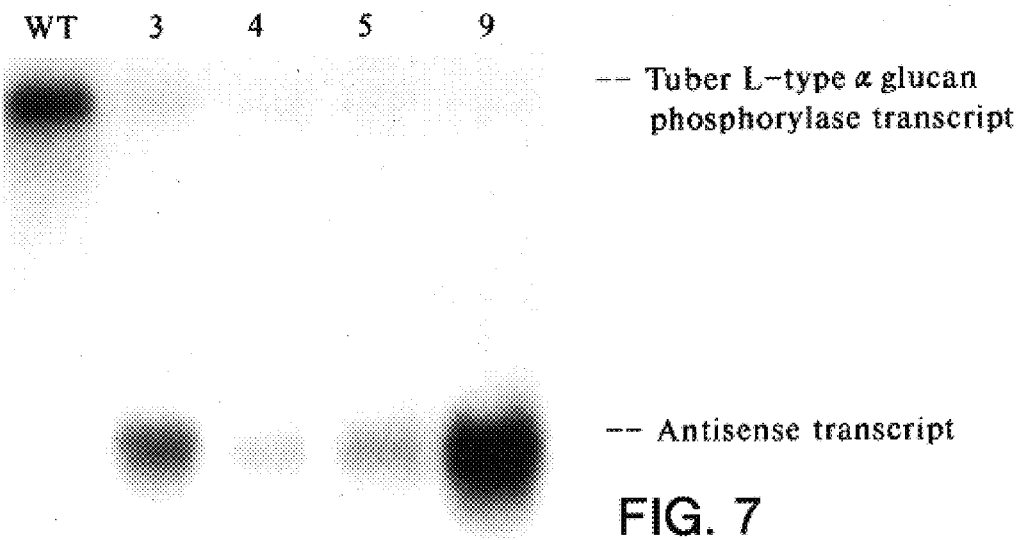
FIG. 7 is a northern blot of polyadenylated RNA isolated from potato tubers of wild type and lines 3,4,5, and 9 transformed with the tuber L-type α glucan phosphorylase.

Following regeneration of potato plants transformed with antisense DNA sequences derived from the GHTP and GLTP genes, the biochemistry of transformed tuber tissue was analyzed several ways. The in vitro activity of α glucan phosphorylase in the phosphorolytic direction was assayed according to the methods of Steup (1990) (Table 1). The activity of the enzyme in the synthetic direction and the amount of enzyme protein were compared after electrophoretic separation of the enzyme isoforms on a glycogen-containing, polyacrylamide gel (FIG. 7). Starch synthesis by the tuber L-type and H-type isoforms was determined by iodine staining of the gel after incubation with glucose-1-phosphate and a starch primer (Steup, 1990). Western analysis was performed by blotting the protein from an identical unincubated native gel to nitrocellulose and probing with polyclonal antibodies specific for tuber type L and type H glucan phosphorylase isoforms. Levels of reducing sugars (glucose and fructose) in tuber tissues were quantified by HPLC (Tables 2, 3 and 4). The extent of Maillard reaction, which is proportional to the concentration of reducing sugars in tubers was examined by determining chip scores after frying (Table 5 and FIG. 9).

10 Definitions

As used herein and in the claims, the term:

"about three months", "about four months" and "about six months" refer, respectively, to periods of time of three months plus or minus two weeks, four months plus or minus two weeks, and six months plus or minus two weeks;

"antisense orientation" refers to the orientation of nucleic acid sequence from a structural gene that is inserted in an expression cassette in an inverted manner with respect to its naturally occurring orientation. When the sequence is double stranded, the strand that is the template strand in the naturally occurring orientation becomes the coding strand, and vice versa;

"chip score" of a tuber means the reflectance measurement recorded by an Agtron model E-15-FP Direct Reading Abridged Spectrophotometer (Agtron Inc. 1095 Spice Island Drive #100, Sparks Nevada 89431) of a center cut potato chip fried at 205° F. in soybean oil for approximately 3 minutes until bubbling stops;

"cold storage" or "storage at reduced temperature" or variants thereof, shall mean holding at temperatures less than 10° C., that may be achieved by refrigeration or ambient temperatures;

"endogenous", as it is used with reference to α glucan phosphorylase genes of a potato plant, shall mean a naturally occurring gene that was present in the genome of the potato plant prior to the introduction of an expression cassette carrying a DNA sequence derived from an α glucan phosphorylase gene;

"expression" refers to the transcription and translation of a structural gene so that a protein is synthesized;

"heterologous sequence" or "heterologous expression cassette" is one that originates from a foreign species, or, if from the same species, is substantially modified from its original form;

"improved cold-storage characteristics" includes, without limitation, improvements in chip score and reduction in sugar accumulation in tubers measured at harvest or after a period of storage below 10° C., and further includes improvements, advantages and benefits which may result from the storage of potatoes at cooler temperatures than those traditionally used, such as, without limitation, increased storage life of potatoes, increased dormancy through reduced respiration and sprouting of potatoes, and reduced incidence of disease. Unless further qualified by a specific measure or test, an improvement in a cold-storage characteristic refers to a difference in the described characteristic relative to that in a control, wildtype or unmodified potato plant;

"modified" or variants thereof, when used to describe potato plants or tubers, is used to distinguish a potato plant or tuber that has been altered from its naturally occurring state through: the introduction of a nucleotide sequence from the same or a different species, whether in a sense or antisense orientation, whether by recombinant DNA technology or by traditional cross-breeding methods including the introduction of modified structural or regulatory sequences; modification of a native nucleotide sequence by site-directed mutagenesis or otherwise; or the treatment of the potato plant with chemical or protein inhibitors. An "unmodified" potato plant or tuber means a control, wildtype or naturally occurring potato plant or tuber that has not been modified as described above;

"nucleic acid sequence" or "nucleic acid segment" refer to a single or double-stranded polymer of deoxyribonucleotide or ribonucleotide bases read from the 5' to the 3' end. It includes both self-replicating plasmids, infectious polymers of DNA or RNA and non-functional DNA or RNA;

"operably linked" refers to functional linkage between a promoter and a second sequence, wherein the promoter sequence initiates transcription of RNA corresponding to the second sequence;

"plant" includes whole plants, plant organs (e.g. leaves, stems, roots, etc.) seeds and plant cells;

"promoter" refers to a region of DNA upstream from the structural gene and involved in recognition and binding RNA polymerase and other proteins that initiate transcription. A "plant promoter" is a promoter capable of initiating transcription in plant cells;

"reduced activity" or variants thereof, when used in reference to the level of GLTP or GHTP enzyme activity in a potato tuber includes reduction of GLTP or GHTP enzyme activity resulting from reduced expression of the GLTP or GHTP gene product, reduced substrate affinity of the GLTP or GHTP enzyme, and reduced catalytic activity of the GLTP or GHTP enzyme;

"reduced" or variants thereof, may be used herein with reference to, without limitation, activity levels of GLTP or GHTP enzyme in potato tubers, accumulation of sugars in potato tubers and darkening of potato chips upon frying. Unless further qualified by a specific measure or test, reduced levels or reduced activity refers to a demonstrable statistically significant difference in the described characteristic relative to that in a control, wildtype or unmodified potato plant;

"stress" or variants thereof, when used in relation to stresses experienced by potato plants and tubers, includes the effects of environment, fertility, moisture, temperature, handling, disease, atmosphere and aging that impact upon plant or tuber quality and which may be experienced by potato plants through all stages of their life cycle and by tubers at all stages of the growth and development cycle and during subsequent harvesting, transport, storage and processing;

"stress resistance" or variants thereof, shall mean reduced effects of temperature, aging, disease, atmosphere, physical handling, moisture, chemical residues, environment, pests and other stresses;

"suitable host" refers to a microorganism or cell that is compatible with a recombinant plasmid, DNA sequence or recombinant expression cassette and will permit the plasmid to replicate, to be incorporated into its genome, or to be expressed; and "uninterrupted" refers to a DNA sequence (e.g. cDNA) containing an open reading frame that lacks intervening, untranslated sequences.

EXAMPLE 1

This example describes the reduction of GHTP and/or GLTP activity in tubers of potato plants by transforming potato plants with expression cassettes containing DNA sequences derived from the GLTP and GHTP gene sequences linked to the promoter in the antisense orientation.

A Isolation of Potato Tuber mRNA

Potato total RNA was purified at 4° C. using autoclaved reagents from 1 g of tuber tissue ground to a fine powder under liquid nitrogen with a mortar and pestle. The powder was transferred to a 30 ml corex tube and 3 volumes were added of 100 mM Tris-Cl, pH 8.0, 100 mM NaCl, and 10 mM EDTA (10× TNE) containing 0.2% (w/v) SDS and 0.5% (v/v) 2-mercaptoethanol. An equal volume of phenol-chloroform (1:1) was added and the sample gently vortexed before centrifugation at 4° C. in a SS34 rotor at 8,000 rpm for 5 min. The organic phase was reextracted with 0.5 volume of 10× TNE containing 0.2% (w/v)SDS and 0.5% (v/v) 2-mercaptoethanol and the combined aqueous phases were extracted with chloroform. Nucleic acids were precipitated from the aqueous phase with sodium acetate and absolute ethanol, pelleted by centrifugation, and resuspended in 3 ml of 1× TNE. An equal volume of 5 M LiCl was added and the sample stored at −20° C. for at 4 h before centrifuging at 8,000 rpm in a SS34 rotor at 4° C. for 10 min. The RNA pellet was washed with 70% ethanol, dried, and resuspended in DEPC-treated water.

Poly (A$^+$) RNA was isolated using oligo (dT) cellulose (Boehringer Mannheim) column chromatography. Poly (A$^+$) RNA was isolated from total RNA resuspended in RNAse free water. Columns were prepared using an autoclaved Bio-Rad Poly-Prep 10 ml column to which was added 50 mg of oligo (dT) cellulose suspended in 1 ml of loading buffer B which contains 20 mM Tris-Cl, pH 7.4, 0.1 M NaCl, 1 mM EDTA, and 0.1% (w/v) SDS. The column was washed with 3 volumes of 0.1 M NaOH with 5 mM EDTA and then DEPC-treated water until the pH of effluent was less than 8, as determined with pH paper. The column was then washed with 5 volumes of loading buffer A containing 40 mM Tris-Cl, pH 7.4, 1 M NaCl, 1 mM EDTA, and 0.1% (w/v) SDS.

RNA samples were heated to 65° C. for 5 min at which time 400 μl of loading buffer A, prewarmed to 65° C., was added. The sample was mixed and allowed to cool at room temperature for 2 min before application to the column. Eluate was collected, heated to 65° C. for 5 min, cooled to room temperature for 2 min, and reapplied to the column. This was followed by a 5 volume washing with loading buffer A followed by a 4 volume wash with loading buffer B. Poly (A+) RNA was eluted with 3 volumes of 10 mM Tris-Cl, pH 7.4, 1 mM EDTA, and 0.05% (w/v) SDS. Fractions were collected and those containing RNA were identified in an ethidium bromide plate assay, a petri dish with 1 % agarose made with TAE containing EtBr. RNA was precipitated, resuspended in 10 μl, and a 1 μl aliquot quantitated with a spectrophotometer.

B Isolation of GLTP and GHTP DNA Sequences

The nucleotide sequences utilized in the development of the antisense construct were randomly selected from the 5' sequence of GLTP (SEQ ID NO: 1) and GHTP (SEQ ID NO: 3). DNA sequences used to develop the antisense constructs were obtained using reverse transcription-polymerase chain reaction. GLTP (SPL1 and SPL2)- and GHTP (SPH1 and SPH2)-specific primers were designed according to the published sequences (Brisson et al. 1990, Fukui et al. 1991) with minor modifications to facilitate restriction with enzymes:

SPL1 Primer: 5'ATTCGAAAAGCT$\underline{C}$GAGATTTGCAT AGA3' (SEQ ID NO: 7) (additional CG creates Xho I site);
SPL2 Primer: 5'GTGTGCTCTC$\underline{G}$AGCATTGAAAGC3' (SEQ ID NO: 8) (changed C to G to create Xho I site);
SPH1 Primer: 5'GTTTATTTTCCAT$\underline{CGAT}$GGAAGGTG GTG3' (SEQ ID NO: 9) (added CGAT to create Cla I site);
SPH2 Primer: 5'ATAATATCCTGAA$\underline{T}$CGATGCACTGC3' (SEQ ID NO: 10) (changed G to T to create Cla I site).

Reverse transcription was performed in a volume of 15 μl containing 1×PCR buffer (10 mM Tris-Cl pH 8.2, 50 mM KCl, 0.001% gelatin, 1.5 mM MgCl$_2$), 670 μM of each dNTP, 6 μg of total potato tuber cv. Russet Burbank RNA, 1 mM each primer (SPH1 and SPL2, or SPH1 and SPH2) and 200 U of Maloney murine leukemia virus reverse transcriptase (BRL). The reaction was set at 37° C. for 30 minutes, then heat-killed at 94° C. for 5 minutes and snap cooled on ice. To the reverse transcription reaction was added 2.5 U Taq DNA polymerase (BRL) in 35 μl of 1×PCR buffer. DNA amplification was done in a Perkin Elmer 480 programmed for 30 cycles with a 1 min 94° C. denaturation step, a 1 min 56° C. (SPL1 and SPL2) or 58° C. (SPH1 and SPH2) annealing step, and a 2 min 72° C. extension step. PCR was completed with a final 10 min extension at 72° C.

C Construction of SP Vectors for Phosphorylase Inhibition

To express the antisense constructs in plant cells, it was necessary to fuse the genes to the proper plant regulatory regions. This was accomplished by cloning the antisense DNA into a plasmid vector that contained the needed sequences.

Amplified DNA was blunt ended and cloned into a pUC 19 vector at the SmaI site. The recombinant plasmid was transformed into sub-cloning efficiency E. coli DH5α cells (BRL). The transformed cells were plated on LB (15 g/l Bactotyptone, 5 g/l yeast extract, 10 g/l NaCl, pH 7.3, and solidified with 1.5% agar) plates that contained ampicillin at 100 ug/ml Selection of bacteria containing plasmids with inserted plant phosphorylase sequence was accomplished using color selection. The polylinker and T3 and T7 RNA polymerase promoter sequences are present in the N-terminal portion of the lacZ gene fragment. pUC19 plasmids without inserts in the polylinker grow as blue colonies in appropriate bacterial strains such as DH5α. Color selection was made by spreading 100 μl of 2% X-gal (prepared in dimethyl formamide) on LB plates containing 50 μg/ml ampicillin 30 minutes prior to plating the transformants. Colonies containing plasmids without inserts will be blue after incubation for 12 to 18 hours at 37° C. and colonies with plasmids containing inserts will remain white. An isolated plasmid was sequenced to confirm the sequence of the phosphorylase inserts. Sequences were determined using the ABI Prism Dye Terminator Cycle Sequencing Core Kit (Applied Biosystems, Foster City, Calif.), M13 universal and reverse primers, and an ABI automated DNA sequencer. The engineered plasmid was purified by the rapid alkaline extraction procedure from a 5 ml overnight culture (Birnboim and Doly, 1979). Orientation of the SPL and SPH fragments in pUC19 was determined by restriction enzyme digestion. The recombinant pUC19 vectors and the binary vector pBI121 (Clonetech) were restricted, run on a agarose gel and the fragments purified by gel separation as described by Thuring et al (1975).

Ligation fused the antisense sequence to the binary vector pBI121. The ligation contained pBI121 vector that had been digested with BamHI and SacI, along with the SPL or SPH phosphorylase DNA product, that had been cut from the pUC19 subclone with BamHI and SacI. Ligated DNA was transformed into SCE E. coli DH5α cells, and the transformed cells were plated on LB plates containing ampicillin. The nucleotide sequences of the antisense DNA SPL and SPH are nucleotides 338 to 993 of SEQ ID NO: 1 and nucleotides 147 to 799 of SEQ ID NO: 3, respectively. Selection of pBI121 with phosphorlyase inserts was done with CAMV and NOS specific primers.

Samples 1 and 2 representing the tuber L-type and tuber H-type phosphorylase DNA fragments were picked from a plate after overnight growth. These samples were inoculated into 5 ml of LB media and grown overnight at 37° C. Plasmids were isolated by the rapid alkaline extraction procedure, and the DNA was electroporated into Agrobacterium tumefaciens.

Constructs were engineered into the pBI121 vector that contains the CAMV 35S promoter (Kay et al. 1987) and the NOS 3' terminator (Bevan et al. 1983) sequence. The pBI121 plasmid is made up of the following well characterized segments of DNA. A 0.93 kb fragment isolated from transposon Tn7 which encodes bacterial spectinomycin/ streptomycin (Spc/Str) resistance and is a determinant for selection in E. coli and Agrobacterium tumefaciens (Fling et al., 1985). This is joined to a chimeric kanamycin resistance gene engineered for plant expression to allow selection of the transformed tissue. The chimeric gene consists of the 0.35 kb cauliflower mosaic virus 35S promoter (P-35S) (Odell et al., 1985), the 0.83 kb neomycin phosphotransferase type II gene (NPTII), and the 026 kb 3' non-translated region of the nopaline synthase gene (NOS 3') (Fraley et al., 1983). The next segment is a 0.75 kb origin of replication from the RK2 plasmid (ori-V) (Stalker et al., 1981). It is joined to a 3.1 kb SalI to PvuI segment of pBR322 which provides the origin of replication for maintenance in E. coli (ori-322) and the bom site for the conjugational transfer: in the Agrobacterium tumefaciens cells. Next is a 0.36 kb PvuI fragment from the pTiT37 plasmid which contains the nopaline-type T-DNA right border region (Fraley et al., 1985). The antisense sequence was engineered for expression in the tuber by placing the gene under the control of a constitutive tissue non-specific promoter.

D Plant Transformation/Regeneration

The SPL and SPH vectors were transformed into the Desiree potato cultivar according to de Block (1988). To transform "Desiree" potatoes, sterile shoot cultures of "Desiree" were maintained in test tubes containing 8 ml of S 1 (Murashige and Skoog (MS) medium supplemented with 2% sucrose and 0.5 g/l MES pH 5.7, solidified with 6 g/l Phytagar). When plantlets reached approximately 5 cm in length, leaf pieces were excised with a single cut along the base and inoculated with a 1:10 dilution of an overnight culture of Agrobacterium tumefaciens. The stem explants were co-cultured for 2 days at 20° C. on S1 medium (De Block 1988). Following co-culture, the explants were transferred to S4 medium (MS medium without sucrose, supplemented with 0.5 g/l MES pH 5.7, 200 mg/l glutamine, 0.5 g/l PVP, 20 g/l mannitol, 20 g/l glucose, 40 mg/l adenine, 1 mg/l trans zeatin, 0.1 mg/l NAA, 1 g/l carbenicillin, 50 mg/l kanamycin, solidified with 6 g/l phytagar) for 1 week and then 2 weeks to induce callus formation.

After 3 weeks, the explants were transferred to S6 medium (S4 without NAA and with half the concentration (500 mg/1) of carbenicillin). After another two weeks, the explants were transferred to S8 medium (S6 with only 250 mg/l carbenicillin and 0.01 mg/l gibberellic acid, GA3) to promote shoot formation. Shoots began to develop approximately 2 weeks after transfer to S8 shoot induction medium. These shoots were excised and transferred to vials of S1 medium for rooting. After about 6 weeks of multiplication on the rooting medium, the plants were transferred to soil and are gradually hardened off.

Desiree plants regenerated in culture were transplanted in 1 gallon pots and were grown to maturity under greenhouse conditions. Tubers were harvested and allowed to suberize at room temperature for two days. All tubers greater than 2 cm in length were collected and stored at 4° C. under high humidity.

E Field Trials

Untransformed controls, plants expressing the SPL construct, and plants expressing the SPH construct were propagated in field trials in a single replicate randomized design. All plants were grown side by side in the same field and exposed to similar pesticide, fertilizer, and irrigation regimes. Tubers were harvested and stored at 10° C. for 2 weeks before randomly selecting a fraction of the tubers from each line to be placed in storage at 4° C.

F Sugar Analysis

Tubers were stored at 4° C. and were not allowed to recondition at room temperature prior to sugar analysis. An intact longitudinal slice (1 cm thick, width variable and equal to the outside dimensions of the tuber) was cut from the central portion of each tuber, thus representing all of the tuber's tissues. At each harvest, the central slices from four tubers per clone (3 replicates) were collectively diced into 1-cm cubes and 15 g was randomly selected from the pooled tissue for analysis. Glucan phosphorylase (see below) and sugars were extracted with 15 mL of Tris buffer (50 mM, pH 7.0) containing 2 mM sodium bisulfite, 2 mM EDTA. 0.5 mM PMSF and 10% (w/w) glycerol with a polytron homogenizer at 4° C. The extracts were centrifuged at 4° C. (30,000 g, 30 min) and reducing sugars (glucose and fructose) were measured on a 10-fold dilution of the supernatant using a Spectra Physics high performance liquid chromatograph interfaced to a refractive index detector. The separation was performed at 80° C. on a 30×0.78 cm Aminex HPX 87C column (Biorad) using 0.6 ml/min water as the mobile phase. Calibration of the instrument was via authentic standards of d-glucose and d-fructose.

G Analysis of α-Glucan Phosphorylase Activity

Tubers stored at 4° C. were not allowed to warm prior to extraction and analysis of a glucan phosphorylase activity and isozymes. The in vitro activity of glucan phosphorylase in the phosphorolytic direction was assayed as described by Steup (1990). Briefly, samples of extracts obtained for sugar analysis (see above) were added to a reaction medium which coupled starch phosphorolysis to the reduction of NADP through the sequential actions of phosphoglucomutase and glucose-6-phosphate dehydrogenase. The rate of reduction of NADP during the reaction is stoichiometric with the rate of production of glucose-1-phosphate from the starch substrate. Reduction of NADP was followed at 340 nm in a Varian Cary double-beam spectrophotometer. Protein levels in extracts were determined according to Bradford (1976).

Glucan phosphorylase activity gels were run essentially according to Steup (1990). Proteins were separated on native polyacrylamide gels (8.5 %) containing 1.5 % glycogen. Following electrophoresis at 80 V for 15 h (4° C.), the gels were incubated (1–2 h) at 37° C. in 0.1 M citrate-NaOH buffer (pH 6.0) containing 20 mM glucose-1-P and 0.05% (w/v) hydrolyzed potato starch. Gels were then rinsed and stained with an iodine solution. For Western blot analysis, proteins were electrophoresed on glycogen-containing polyacrylamide gels as described above. The proteins were electroblotted to nitrocellulose and blots were probed with polyclonal antibodies raised against GHTP and GLTP. Immunoblots were developed with alkaline phosphatase conjugated anti-rabbit secondary antibodies (Sigma).

H Chip Color Determination

Five transgenic potato lines expressing the GLTP antisense sequence, two transgenic lines expressing the GHTP antisense sequence, non-transgenic Desiree control lines, and two control lines transformed with the pBI121 vector T-DNA, were grown under field conditions in Alberta, Canada. Tubers were harvested and stored at 10° C. and 4° C. Chip color was determined for all potato lines by taking center cuts from representative samples from each line and frying at 205° F. in soybean oil for approximately 3 minutes until bubbling stops.

Results

All tubers were harvested from plants of the same cultivar (Desiree), the same age, and grown side by side under identical growth conditions. Northern analysis of tubers showed a considerable reduction of endogenous GLTP transcript in transgenic plants expressing the homologous antisense transcript (FIG. 7). Glucan phosphorylase assays showed that activities ($\mu$mol NADPH mg$^{-1}$ protein h$^{-1}$) were reduced (Table 1) at harvest and for at least six months following harvest in transgenic plants expressing the GLTP antisense DNA. The results tabulated in Table 1 show that α glucan phosphorylase activity in tubers stored at 4° C. for 189 days was reduced from approximately 16% to 70% in various transformed potato varieties relative to the wildtype control strain. Activity gels and western blot analysis showed specific reduced expression of homologous enzymes and lower reduction of expression for heterologous enzymes (FIGS. 10 and 11). This specificity for homologous products may result from differences between the phosphorylases (FIGS. 6A and 6B).

Analysis of tubers at harvest (0 days) shows that those expressing the antisense GLTP transcript have up to 5-fold less reducing sugars than control tubers (Table 2). Furthermore, after 91 days storage at 4° C., transformed tubers contained 28–39% lower reducing sugar concentrations than the wildtype control strain. Concentrations of glucose and fructose were reduced significantly in tubers expressing the antisense GLTP transcript (Tables 3 and 4). These results suggest that reduced GLTP activity slows the catabolism of starch into reducing, sugars in tubers, while in the control tubers the sugars continue to accumulate. The correlation between total phosphorylase activity and the concentration of reducing sugars is not direct, suggesting that certain isozymes of phosphorylase may play a more important role in the catabolism of starch, that specific levels of reduced expression of particular phosphorylase isozymes may be more optimum than others, and/or that there may be unidentified interactions involved in the lower reducing sugar levels.

Transgenic potato plants expressing the antisense GLTP or GHTP transcript have been grown under field conditions and their tubers stored at 4° C. Chip color, which correlated with sugar content, was determined prior to cold storage and after 86 and 124 days of cold storage. The chip color of tubers from all transgenic plants expressing the antisense GLTP transcript was significantly improved (lighter) relative to that of control tubers (darker) stored under identical conditions (Table 5 and FIG. 9). Chip scores of tubers from "Desiree" potato plants expressing the GLTP transcript were improved by at least 4.3 points and 8.9 points as determined with an Agtron model E-15-FP Direct Reading Abridged Spectrophotometer (Agtron Inc. 1095 Spice Island Drive #100, Sparks Nevada 89431) following storage at 10° C. and 4° C., respectively, for 86 days. Chip scores of GLTP transformants measured after 124 days of storage at 4° C. were improved by 44% to 89% relative to wildtype (Table 5).

The Desiree cultivar is not a commercially desirable potato for chipping due to its high natural sugar content and propensity to sweeten rapidly in cold storage. Nevertheless, significant improvements in fried chip color were noted with the transformed "Desiree" potatoes. It is expected that superior color lightening would be achieved if the methods of the invention were applied to commercial processing potato varieties.

Analysis of tubers stored at 10° C. and 4° C. shows that those expressing the antisense GHTP transcript sometimes provided chips that fried lighter than control tubers, indicating a lower buildup of reducing sugars (Table 5). Results showing heterologous and homologous reduction in phosphorylase activity (FIGS. 10 and 11) indicate that the improvement may be a result of reducing one or both tuber phosphorylases. However, these results suggest that the L-type phosphorylase plays a more important role in the catabolism of starch into reducing sugars.

Further, the results show that the difference in reducing sugar levels (Table 2) and chip scores (Table 5) between tubers wildtype plants and those expressing tuber phosphorylase antisense RNA, are sustained during long-term storage. As shown in Table 5, the chip scores are approximately the same at 86 days and 124 days. No further increases in reducing sugar concentrations were evident after 49 and 91 days storage at 4° C. (Table 2). This equilibrium in sugar concentration was probably associated with the kinetics of the tuber phosphorylases. The capability of maintaining lower sugar levels has the potential of extending the period of storage by at least several months. Presently, processing potatoes are usually stored for a maximum of three to six months at 10° C. to 12° C. before the sugar accumulation reaches levels that reduce quality. Fresh product must be imported until the present season potatoes become available. Extending the storage period of potatoes by many months may reduce import costs.

Table 6 provides a summary of the percentage improvement in various improved tuber cold-storage characteristics of tubers of potato plants transformed with antisense DNA derived from the GLTP gene sequence (ATL3–ATL9), and from the GHTP gene sequence (ATH1 and ATH2) relative to untransformed control plants. It is apparent from the results summarized in Table 6 that substantial improvements in tuber cold-storage characteristics may be consistently obtained through the methods of the present invention. Particularly noteworthy are the percentage chip score improvements over wildtype observed after storage at 4° C. for approximately four months (124 days). Relative chip score improvements of up to 89% relative to wildtype were observed. Improved chip scores reflect the commercial utility of the invention. That is, by reducing cold-induced sweetening, tubers can be stored at cooler. temperatures, without causing unacceptable darkening of fried potato products.

The reduction in sugar accumulation of transformed potato lines relative to wildtype, both at harvest and after 91 day storage, also demonstrates significant advantages of the invention. Reduced sugar accumulation relates to the observed chip score improvements, and also reflects improved specific gravity of tubers, another important commercial measure of tuber quality.

Even at harvest, substantial improvements in chip score and reduced sugar accumulation were noted for transformed lines relative to wildtype. Thus, the benefits of the invention are not limited to improvements that arise only after extended periods of cold storage, but that are present at the time of harvest. In this sense, the invention is not limited only to improvements in cold-storage characteristics but encompasses improvements in tuber quality characteristics such as chip score or sugar accumulation which are present at the time of harvest, resulting in earlier maturity.

Turning to specific improvements summarized in Table 6, it can be seen that GLTP-type transformants (ATL3–ATL9) exhibited up to a 66%, 70% and 69% reduction in α glucan phosphorylase activity relative to wildtype, at harvest, and after storage for 91 and 189 days, respectively. Most also exhibited improvements in excess of 10% and 30% relative to wildtype at harvest and after storage for 91 and 189 days. After storage for 91 and 189 days, the GHTP-type transformants (ATH1 and ATH2) exhibited, respectively, up to 28% and 39% relative improvement over wildtype and generally showed at least 10% improvement.

The GLTP-type transformants exhibited up to 80% and 39% reduction of sugar accumulation relative to wildtype at harvest and at 91 days, respectively. At harvest, all GLTP-type transformants exhibited at least 10% and at least 30% relative improvement. At 91 days, all GLTP-type transformants exhibited at least 10% and most exhibited at least 30% relative improvement.

The GLTP-type transformants exhibited up to 46%, 89% and 89% chip score improvement relative to wildtype at harvest, and after storage for 86 days and 124 days, respectively. Almost all exhibited at least 10% and 30% relative improvement at harvest, and after storage for 86 and 124 days. At least one of the GHTP-type transformants exhibited at least 5% and at least 10% improvement relative to wildtype at harvest, and after storage for 86 and 124 days. After 124 days storage, at least one of the GHTP-type transformants exhibited up to 25% relative improvement in chip score.

The results clearly demonstrate that substantial improvements in tuber cold-storage characteristics may be readily obtained through the methods of the invention. Results will vary due to, among other things, the location within the plant genome where the recombinant antisense or sense DNA is inserted, and the number of insertion events that occur. It is important to note that despite the variability in the results amongst the various transformed lines, there was little variation in the results amongst the samples within a single transformed potato line (see footnotes to Tables 1 to 5). Results are presented in Table 6 for all potato plant lines which were successfully transformed with the GHTP or GLTP antisense DNA. Therefore, all transformants show at least some improvement in one or more cold-storage characteristics such as increased chip score (lighter color on cooking) and reduced sugar accumulation, and most show very substantial improvements. Given the large proportion of positive transformants observed in the examples herein, it is expected that, using the cold-storage characteristic testing, procedures described in the examples, potato plants transformed through the methods of the invention can be readily screened to identify transformed lines exhibiting significantly improved cold-storage characteristics. By applying the techniques disclosed herein to commercially important potato varieties, it will be possible to readily create and select transformants having significantly improved cold-storage characteristics. Those transformants showing the greatest relative improvements over wildtype controls can be used in the development of new commnercial potato varieties.

TABLE 1

Effects of an antisense transcript on glucan phosphorylase activity measured in enzyme extracts from field grown "Desiree" tubers.

| | Glucan Phosphorylase Activity Storage Period at 4C (days) | | | | |
|---|---|---|---|---|---|
| Clone | 0 | 49 | 91 | 140 | 189 |
| | $\mu$mol NADPH mg$^{-1}$ protein b$^{-1}$ | | | | |
| Wt[a] | 10.50 | 11.83 | 9.94 | 11.90 | 13.04 |
| ATL3 | 4.90 | 4.86 | 4.49 | 4.73 | 4.88 |
| ATL4 | 11.45 | 7.17 | 8.09 | 11.32 | 10.99 |
| ATL5 | 3.58 | 3.56 | 2.97 | 4.59 | 4.79 |
| ATL9 | 3.59 | 3.88 | 3.84 | 4.72 | 3.98 |
| LSD$_{0.05}$[b] | 1.97 | 2.94 | 1.59 | 2.34 | 2.58 |
| LSD$_{0.01}$ | 2.87 | 4.28 | 2.31 | 3.41 | 3.75 |
| Clone[c] | | 0.01[d] | | | |
| WT vs. ATL's | | 0.01 | | | |
| Days | | NS | | | |
| Clone x Days | | 0.05 | | | |
| Wt | | 11.49 | 8.90 | 12.66 | 13.66 |
| ATH-1 | | 10.40 | 9.69 | 10.79 | 10.10 |
| ATH-2 | | 6.46 | 6.40 | 6.56 | 8.38 |
| LSD$_{0.05}$[b] | | 2.02 | 0.41 | 3.00 | NS |
| LSD$_{0.01}$ | | 4.78 | 0.95 | NS | NS |
| Clone[c] | | 0.01 | | | |
| WT vs. ATH's | | 0.01 | | | |
| Days | | 0.05 | | | |
| Clone x Days | | NS | | | |

[a]WT, wild type untransformed tubers.
[b]LSD, least significant difference at 0.05 or 0.01 level for each storage period.
[c]Sources of variation in factorial analysis.
[d]Significance levels for indicated sources of variation.

TABLE 2

Effects of an antisense GLTP transcript on low temperature induced sweetening of field grown "Desiree" tubers.

| | Reducing Sugars (glucose + fructose) Storage Period at 4C (days) | | |
|---|---|---|---|
| Clone | 0 | 49 | 91 |
| | mg g$^{-1}$ fresh weight | | |
| Wt[a] | 5.63 | 31.8 | 28.0 |
| ATL3 | 1.88 | 17.3 | 17.3 |
| ATL4 | 1.11 | 14.3 | 20.1 |
| ATL5 | 1.51 | 18.3 | 17.0 |
| ATL9 | 1.36 | 17.3 | 18.5 |
| WT vs. ATL's[b] | 0.01 | 0.01 | 0.05 |
| Clone[c] | | 0.01[d] | |
| Days | | 0.01 | |
| Clone x Days | | NS | |

[a]WT, wild type untransformed tubers.
[b]Orthogonal comparisons for ANOVA's at each storage period,
[c]sources of variation in factorial analysis.
[d]Significance levels for indicated sources of variation.

TABLE 3

Effects of antisense GLTP transcript on low temperature induced fructose accumulation of field grown "Desiree" tubers.

| | Fructose Storage Period at 4C (days) | | |
|---|---|---|---|
| Clone | 0 | 49 | 91 |
| | mg g$^{-1}$ fresh weight | | |
| Wt[a] | 3.53 | 15.10 | 12.20 |
| ATL3 | 1.21 | 8.40 | 8.79 |
| ATL4 | 0.79 | 7.22 | 8.56 |
| ATL5 | 0.61 | 10.00 | 8.09 |
| ATL9 | 0.54 | 8.38 | 8.72 |
| WT vs. ATL's[b] | 0.01 | 0.01 | NS |
| Clone[c] | | 0.01[d] | |
| Days | | 0.01 | |
| Clone x Days | | NS | |

[a]WT, wild type untransformed tubers.
[b]Orthogonal comparisons for ANOVA's at each storage period,
[c]Sources of variation in factorial analysis.
[d]Significance levels for indicated sources of variation.

TABLE 4

Effects of antisense GLTP transcript on low temperature induced glucose accumulation of field grown "Desiree" tubers.

| | Glucose Storage Period at 4C (days) | | |
|---|---|---|---|
| Clone | 0 | 49 | 91 |
| | mg g$^{-1}$ fresh weight | | |
| Wt[a] | 2.10 | 16.60 | 15.90 |
| ATL3 | 0.68 | 8.94 | 8.49 |
| ATL4 | 0.32 | 7.07 | 11.06 |
| ATL5 | 1.05 | 8.33 | 8.91 |
| ATL9 | 0.83 | 8.87 | 9.78 |
| WT vs. ATL's[b] | 0.01 | 0.01 | 0.05 |
| Clone[c] | | 0.01[d] | |

TABLE 4-continued

Effects of antisense GLTP transcript on low temperature induced glucose accumulation of field grown "Desiree" tubers.

| | Glucose Storage Period at 4C (days) | | |
|---|---|---|---|
| Clone | 0 | 49 | 91 |
| Days | | | 0.01 |
| Clone × Days | | | NS |

[a]WT, wild type untransformed tubers.
[b]Orthogonal comparisons for ANOVA's at each storage period,
[c]sources of variation in factorial analysis.
[d]Significance levels for indicated sources of variation.

TABLE 5

Average chip color of field grown "Desiree" tubers. The chip color rating was assigned using an Agtron meter similar to that used by industry to measure color of fried potatoes. In this index, the higher the number the lighter the chip product but color does not represent a linear relationship to the index.

| | Storage Temperature, Period, and Agtron Reading[a] | | | |
|---|---|---|---|---|
| | Harvest | 86 days 10C | 86 days 4C | 124 days 4C |
| Wt[b] | 26 | 25.3 | 15.4 | 17.1 |
| ATL3[c] | 25 | 37.4 | 26.7 | 30.8 |
| ATL4 | 35 | 43.7 | 29.1 | 32.3 |
| ATL5 | 36 | 29.6 | 24.7 | 24.6 |
| ATL9 | 38 | 38.7 | 24.3 | 26.6 |
| ATH1[d] | 26 | 49.7 | 17.5 | 21.4 |
| ATH2 | 29 | 31.2 | 15.6 | 15.9 |
| GMP1[e] | 31 | | 15.7 | 15.7 |
| GMP2 | 35 | | 16.7 | 16.6 |

[a]Agtron Inc. 1095 Spice Island Drive #100, Sparks Nevada 89431. Agtron model E-15-FP (Direct Reading Abridged Spectrophotometer). Measures ratio of reflectance in two spectral modes, near infrared and green. Results represent the measurement of 6 to 8 chips from 3 randomly selected tubers approximately 3 to 4 cm in diameter.
[b]WT, negative control, wild type untransformed tubers.
[c]ATL, tubers transformed with the tuber L-type glucan phosphorylase.
[d]ATH, tuber transformed with the tuber H-type glucan phosphorylase.
[e]GMP, negative control, tubers transformed with pBI121 T-DNA.

TABLE 6

Summary of Results

| Sample | % Reduction of a α glucan phosphorylase activity relative to wildtype | | | % Reduction of Sugar Accumulation relative to wildtype | | % Chip Score Improvement relative to wildtype | | |
|---|---|---|---|---|---|---|---|---|
| | at harvest | 91 days | 189 days | at harvest | 91 days | at harvest | 86 days | 124 days |
| ATL3 | 53 | 55 | 63 | 67 | 38 | −4 | 73 | 80 |
| ATL4 | −9 | 19 | 16 | 80 | 28 | 35 | 89 | 89 |
| ATL5 | 66 | 70 | 63 | 73 | 39 | 38 | 60 | 44 |
| ATL9 | 66 | 61 | 69 | 76 | 34 | 46 | 58 | 56 |
| ATH1 | n/a | −9 | 26 | n/a | n/a | 0 | 14 | 25 |
| ATH2 | n/a | 28 | 39 | n/a | n/a | 12 | 1 | −7 |

REFERENCES

Alber and Kawasaki (1982) Mol. And Appl. Genet. 1:419–434.
ap Rees et al. (1988) Symp. Soc. Exp. Biol. 42:377–393.
Bevan et al. (1983) Nature (London) 304:184–187.
Bevan et al. (1986) Nucleic Acids Res. 14 (11):4625–4638.
Birmboim et al. (1979) Nucleic Acids Res. 7:1513–1523.
Blennow et al. (1991) Phytochemistry 30:437–444.
Bradford, M. M. 1976. A rapid and sensitive method for quantification of microgram quantities of protein utilizing the principle of protein dye binding. Anal. Biochem. 72: 243–254.
Brisson et al. (1989) The Plant Cell 1:559–566.
Brusslan and Tobin (1995) Plant Molecular Biology 27:809–813.
Burton, W. G. (1989) The Potato. Longman Scientific and Technical,
Cannon et al. (1990) Plant Molecular Biology 15:39–47
Claassen etal. (1991) Plant Physiol. 95:1243–1249.
Coffin et al. (1987) J. Food Sci. 52:639–645.
Davies and Viola (1992) Postharvest News and Information 3:97–100.
De Block, M. (1988) Theoretical and Applied Genetics 76:767–774.
De Carvalho et al. (1992) EMBO J. 11:2595–2602.
Depicker et al. (1982) Mol. And Appl. Genet. 1:561–573.
Dixon et al. (1981) Phytochemistry 20:969–972.
Dorlhac et al. 1994 Mol. Gen. Genetic. 243:613–621.
Ebbelaar et al. (1993) Int. Symp. on Gen. Manip. of Plant Metabolism and Growth, 29–31 March, Norwich UK Abstract #9.
Ecker and Davis (1986) Proc. Natl. Acad. Sci. 83: 5373–5376.
Fling et al. (1985) Nucleic Acids Research 13 no. 19, 7095–7106.
Fraley, et al. (1983) Proc Natl Acad Sci USA 80, 4803–4807.
Fraley et al. (1985) Bio/Technology 3, 629–635.
Fray and Grierson 1993 Plant Mol. Biol. 22:589–602.
Gielen et al. (1984) EMBO J. 3:835–846.
Hasseloff, J. And W. L. Gerlach (1988) Nature 334:585–591.
Hart et al. (1992) Mol. Gen. Genetic. 235:179–188.
Jorgensen, R. A. (1995) Science 268: 686–691.
Kawchuk et al. (1990) Molecular Plant-Microbe Interactions 3:301–307.
Kawchuk et al. (1991) Mol. Plant Microbe-Inter. 4:247–253.
Kay et al. (1987) Science 236:1299–1302.
Kruger, N. J. and Hammond, J. B. W. (1988) Plant Physiol. 86:645–648.
Laemmli, U. K. (1970) Nature (London) 227:680–685.
Lin et al. (1988) Plant Physiol. 86:1131–1135.
Loiselle et al. (1990) American Potato Journal 67:633–646.
Lynch et al. (1992) Can,. J. Plant Sci. 72: 535–543.
Matzke and Matzke (1995) Plant Physiol. 107:679.
Meyer and Saedler (1996) Annu. Rev. Plant Physiol. 47:23–48.
Mori et al. (1991) J. Biol. Chem. 266:18446–18453.
Muller, et al. (1990) Mol. Gen. Genet. 224:136–146.
Nakano et al. (1989) J. Biochem. 106:691–695.
Nakano, K. and Fukui, T. (1986) J. Biol. Chem. 266:8230–8256.
Napoli et al. (1990) Plant Cell 2:279–289.
Odell, et al. (1985) Nature 313, 810–812.
Ohta et al. (1991) Mol. Gen. Genet. 225:369–378.
Ortiz, R. and Huaman, Z. (1994) In:Potato Genetics. Bradshaw, J. E. and Mackay G. R. (eds.)
Sambrook et al. (1989) Molecular Cloning, A Laboratory Manual. 2nd Ed. Cold Spring Harbor Laboratory Press, N.Y.
Seymour et al. 1993 Plant Mol. Biol. 23:1–9.
Shahar et al. (1992) Plant Cell 4:135–147.
Shallenberger et al. (1959) Agric. and Food Chem. 7:274–277.
Smith et al. (1988) Nature 334:724–726.

Smith et al. (1990) Mol. Gen. Genet. 244:447–481.
Sonnewald et al. (1995) Plant Molecular Biology 27:567–576.
Sowokinos, J. (1990) In: The molecular and Cellular Biology of the Potato. M. A. Mayo and W. D. Parks (eds.).
Stalker et al. (1981) Mol Gen Genet 181, 8–12.
Steup, M. (1990) Starch Degrading Enzymes in "Methods in Plant Biochemistry" Vol 3. P. M. Dey and J. B. Harborne, eds. Academic Press, London
Stiekema et al. (1988) Plant Mol. Biol. 11:255–269.
Stukerlj et al. (1990) Nucl. Acids Res. 18:46050.
Takaha et al., (1993) J. Biol. Chem. 26 8:1391–1396.
Thuring et al. (1975) Analytical Biochemistry 66:213–220.
Van der Krol et al (1988) Gene 72:45–50.
Van der Krol (1990) Plant Cell 2:291–299.
Weaver et al. (1978) Am. Pot. J. 55:83–93.
Weintraub (1990) Scientific American 1:34–40.
Winnacker, Ernst L. (1987) From Genes to Clones. VCH Verlagsgesellschaft mbH, Federal Replublic of Germany
Yoshida et al. (1992) Geneg 10:255–259.

All publications mentioned in this specification are indicative of the level of skill in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it will be obvious that certain changes and modifications may be practised within the scope of the appended claims.

We claim:

1. A potato plant having improved cold-storage characteristics, comprising a potato plant transformed with an expression cassette having a plant promoter sequence operably linked to a DNA sequence comprising at least 20 nucleotides of a gene encoding an α glucan phosphorylase selected from the group consisting of α glucan L-type tuber phosphorylase (GLTP) and α glucan H-type phosphorylase (GHTP).

2. The potato plant of claim 1, wherein the encoded α glucan phosphorylase is GLTP.

3. The potato plant of claim 1, wherein the encoded α glucan phosphorylase is GHTP.

4. The potato plant of claim 1, wherein the DNA sequence comprises nucleotides 338 to 993 of SEQ ID NO: 1.

5. The potato plant of claim 1, wherein the DNA sequence comprises nucleotides 147 to 799 of SEQ ID NO: 3.

6. The potato plant of any one of claims 1, 2, 3, 4 or 5, wherein the DNA sequence is linked to the promoter sequence in an antisense orientation.

7. The potato plant of claim 2, wherein the sum of the concentration of glucose and fructose in tubers of the plant measured at harvest is at least 10% lower than the sum of the concentration of glucose and fructose in tubers of an untransformed plant measured at harvest.

8. The potato plant of claim 2, wherein the sum of the concentration of glucose and fructose in tubers of the plant measured at harvest is at least 30% lower than the sum of the concentration of glucose and fructose in tubers of an untransformed plant measured at harvest.

9. The potato plant of claim 2, wherein the sum of the concentration of glucose and fructose in tubers of the plant measured at harvest is at least 80% lower than the sum of the concentration of glucose and fructose in tubers of an untransformed plant measured at harvest.

10. The potato plant of claim 2, wherein the sum of the concentration of glucose and fructose in tubers of the plant stored at 4° C. for about three months is at least 10% lower than the sum of the concentration of glucose and fructose in tubers of an untransformed plant stored under the same conditions.

11. The potato plant of claim 2, wherein the sum of the concentration of glucose and fructose in tubers of the plant stored at 4° C. for about three months is at least 30% lower than the sum of the concentration of glucose and fructose in tubers of an untransformed plant stored under the same conditions.

12. The potato plant of claim 2, wherein the sum of the concentration of glucose and fructose in tubers of the plant stored at 4° C. for about three months is at least 39% lower than the sum of the concentration of glucose and fructose in tubers of an untransformed plant stored under the same conditions.

13. The potato plant of claim 2, wherein the total α glucan phosphorylase activity measured as $\mu$mol NADPH produced $mg^{-1}$ proteins$^{-1}$ h$^{-1}$ in tubers of the plant measured at harvest is at least 10% lower than the total α glucan phosphorylase activity in tubers of an untransformed plant measured at harvest.

14. The potato plant of claim 2, wherein the total α glucan phosphorylase activity measured as $\mu$mol NADPH produced $mg^{-1}$ protein$^{-1}$ h$^{-1}$ in tubers of the plant measured at harvest is at least 30% lower than the total α glucan phosphorylase activity in tubers of an untransformed plant measured at harvest.

15. The potato plant of claim 2, wherein the total α glucan phosphorylase activity measured as $\mu$mol NADPH produced $mg^{-1}$ protein$^{-1}$ h$^{-1}$ in tubers of the plant measured at harvest is at least 66% lower than the total α glucan phosphorylase activity in tubers of an untransformed plant measured at harvest.

16. The potato plant of claim 2, wherein the total α glucan phosphorylase activity measured as $\mu$mol NADPH produced $mg^{-1}$ protein$^{-1}$ h$^{-1}$ in tubers of the plant stored at 4° C. for about three months is at least 10% lower than the total α glucan phosphorylase activity in tubers of an untransformed plant stored under the same conditions.

17. The potato plant of claim 2, wherein the total α glucan phosphorylase activity measured as $\mu$mol NADPH produced $mg^{-1}$ proteins h$^{-1}$ in tubers of the plant stored at 4° C. for about three months is at least 30% lower than the total α glucan phosphorylase activity in tubers of an untransformed plant stored under the same conditions.

18. The potato plant of claim 2, wherein the total α glucan phosphorylase activity measured as $\mu$mol NADPH produced $mg^{-1}$ protein$^{-1}$ h$^{-1}$ in tubers of the plant stored at 4° C. for about three months is at least 70% lower than the total α glucan phosphorylase activity in tubers of an untransformed plant stored under the same conditions.

19. The potato plant of claim 3, wherein the total α glucan phosphorylase activity measured as $\mu$mol NADPH produced $mg^{-1}$ protein$^{-1}$ h$^{-1}$ in tubers of the plant stored at 4° C. for about three months is at least 10% lower than the total α glucan phosphorylase activity in tubers of an untransformed plant stored under the same conditions.

20. The potato plant of claim 3, wherein the total α glucan phosphorylase activity measured as $\mu$mol NADPH produced $mg^{-1}$ protein$^{-1}$ h$^{-1}$ in tubers of the plant stored at 4° C. Fop about three months is at least 28% lower than the total α glucan phosphorylase activity in tubers of an untransformed plant stored under the same conditions.

21. The potato plant of claim 2, wherein the total α glucan phosphorylase activity measured as $\mu$mol NADPH produced $mg^{-1}$ protein$^{-1}$ h$^{-1}$ in tubers of the plant stored at 4° C. for about six months is at least 10% lower than the total α glucan phosphorylase activity in tubers of an untransformed plant stored under the same conditions.

22. The potato plant of claim 2, wherein the total α glucan phosphorylase activity measured as $\mu$mol NADPH produced $mg^-$protein$^{-1}$ h$^{-1}$ in tubers of the plant stored at 4° C. for about six months is at least 30% lower than the total α glucan phosphorylase activity in tubers of an untransformed plant stored under the same conditions.

23. The potato plant of claim 2, wherein the total α glucan phosphorylase activity measured as μmol NADPH produced mg$^{-1}$ protein$^{-1}$ h$^{-1}$ in tubers of the plant stored at 4° C. for about six months is at least 69% lower than the total α glucan phosphorylase activity in tubers of an untransformed plant stored under the same conditions.

24. The potato plant of claim 3, wherein the total α glucan phosphorylase activity measured as μmol NADPH produced mg$^{-1}$ protein$^{-1}$ h$^{-1}$ in tubers of the plant stored at 4° C. for about six months is at least 10% lower than the total α glucan phosphorylase activity in tubers of an untransformed plant stored under the same conditions.

25. The potato plant of claim 3, wherein the total α glucan phosphorylase activity measured as μmol NADPH produced mg$^{-1}$ proteins$^{-1}$ h$^{-1}$ in tubers of the plant stored at 4° C. for about six months is at least 39% lower than the total α glucan phosphorylase activity in tubers of an untransformed plant stored under the same conditions.

26. The potato plant of claim 2, wherein a chip score for tubers of the plant measured at harvest is at least 5% higher than the chip scores for tubers of an untransformed plant measured at harvest.

27. The potato plant of claim 2, wherein a chip score for tubers of the plant measured at harvest is at least 30% higher than the chip scores for tubers of an untransformed plant measured at harvest.

28. The potato plant of claim 2, wherein a chip score for tubers of the plant measured at harvest is at least 46% higher than the chip scores for tubers of an untransformed plant measured at harvest.

29. The potato plant of claim 3, wherein a chip score for tubers of the plant measured at harvest is at least 5% higher than the chip scores for tubers of an untransformed plant measured at harvest.

30. The potato plant of claim 3, wherein a chip score for tubers of the plant measured at harvest is at least 10% higher than the chip scores for tubers of an untransformed plant measured at harvest.

31. The potato plant of claim 2, wherein a chip score for tubers of the plant stored at 4° C. for about three months is at least 5% higher than the chip scores for tubers of an untransformed plant stored under the same conditions.

32. The potato plant of claim 2, wherein a chip score for tubers of the plant stored at 4° C. for about three months is at least 30% higher than the chip scores for tubers of an untransformed plant stored under the same conditions.

33. The potato plant of claim 2, wherein a chip score for tubers of the plant stored at 4° C. for about three months is at least 89% higher than the chip scores for tubers of an untransformed plant stored under the same conditions.

34. The potato plant of claim 3, wherein a chip score for tubers of the plant stored at 4° C. for about three months is at least 5% higher than the chip scores for tubers of an untransformed plant stored under the same conditions.

35. The potato plant of claim 3, wherein a chip score for tubers of the plant stored at 4° C. for about three months is at least 10% higher than the chip scores for tubers of an untransformed plant stored under the same conditions.

36. The potato plant of claim 2, wherein a chip score for tubers of the plant stored at 4° C. for about four months is at least 5% higher than the chip scores for tubers of an untransformed plant stored under the same conditions.

37. The potato plant of claim 2, wherein a chip score for tubers of the plant stored at 4° C. for about four months is at least 30% higher than the chip scores for tubers of an untransformed plant stored under the same conditions.

38. The potato plant of claim 2, wherein a chip score for tubers of the plant stored at 4° C. for about four months is at least 89% higher than the chip scores for tubers of an untransformed plant stored under the same conditions.

39. The potato plant of claim 3, wherein a chip score for tubers of the plant stored at 4° C. for about four months is at least 5% higher than the chip scores for tubers of an untransformed plant stored under the same conditions.

40. The potato plant of claim 3, wherein a chip score for tubers of the plant stored at 4° C. for about four months is at least 25% higher than the chip scores for tubers of an untransformed plant stored under the same conditions.

41. A method for improving the cold-storage characteristics of a potato tuber, comprising:
   introducing into a potato plant an expression cassette having a plant promoter sequence operably linked to a DNA sequence comprising at least 20 nucleotides of a gene encoding an α glucan phosphorylase selected from the group consisting of GLTP and GHTP.

42. The method of claim 41, wherein the encoded α glucan phosphorylase is GLTP.

43. The method of claim 41, wherein the encoded α glucan phosphorylase is GHTP.

44. The method of claim 41, wherein the DNA sequence comprises nucleotides 338 to 993 of SEQ ID. NO: 1.

45. The method of claim 41, wherein the DNA sequence comprises nucleotides 147 to 799 of SEQ ID. NO: 3.

46. The method of any one of claims 41, 42, 43, 44 or 45 wherein the DNA sequence is linked to the promoter sequence in an antisense orientation.

47. The potato plant of claim 1, wherein the encoded α glucan phosphorylase comprises an amino acid sequence depicted in SEQ ID NO:2.

48. The potato plant of claim 1, wherein the DNA sequence comprises at least 20 nucleotides of the gene encoding α glucan phosphorylase as depicted in SEQ ID NO:1.

49. The potato plant of claim 1, wherein the encoded α glucan phosphorylase comprises an amino acid sequence depicted in SEQ ID NO:4.

50. The potato plant of claim 1, wherein the DNA sequence comprises at least 20 nucleotides of the gene encoding an α glucan phosphorylase as depicted in SEQ ID NO:3.

51. The method of claim 41, wherein the encoded α glucan phosphorylase comprises an animo acid sequence depicted in SEQ ID NO:2.

52. The method of claim 41, wherein the DNA sequence comprises at least 20 nucleotides of the gene encoding an α glucan phosphotylase as depicted in SEQ ID NO:1.

53. The method of claim 41, wherein the encoded α glucan phosphorylase comprises an amino acid sequence depicted in SEQ ID NO:4.

54. The method of claim 41, wherein the DNA sequence comprises at least 20 nucleotides of the gene encoding an α glucan phosphorylase as depicted in SEQ ID NO:3.

* * * * *

UNITED STATES PATENT AND TRADEMARK OFFICE
CERTIFICATE OF CORRECTION

PATENT NO.   : 5,998,701
DATED        : December 7, 1999
INVENTOR(S)  : Kawchuk et al.

It is certified that error appears in the above-identified patent and that said Letters Patent is hereby corrected as shown below:

On the Title Page, under "Other Publications", (Page 2, column 2) under "Fling, May E., et al.", please delete "13:7095-4807" and replace with --13:7095-7106--.

Column 4,
Line 52, please delete "imol" and replace with --$\mu$mol--.
Line 52, please delete "protein$^{-1}$" and replace with --protein--.
Line 56, please delete the comma after the period.

Column 5,
Line 55, please delete "isofornns" and replace with --isoforms--.

Column 7,
Line 1, please delete "coinfer" and replace with --confer--.
Line 65, please delete "MRNA" and replace with --mRNA--.

Column 10,
Line 52, please delete "irmunological" and replace with --immunological--.

Column 11,
Line 19, please italicize "Agrobacterium".

Column 12,
Line 50, please italicize "Agrobacterium".

UNITED STATES PATENT AND TRADEMARK OFFICE
CERTIFICATE OF CORRECTION

PATENT NO. : 5,998,701
DATED : December 7, 1999
INVENTOR(S) : Kawchuk et al.

It is certified that error appears in the above-identified patent and that said Letters Patent is hereby corrected as shown below:

Column 13,
Lines 9-10, please delete "electroporatcd" and replace with --electroporated--.
Line 24, please italicize "Vir".
Line 26, please italicize "vir".
Line 27, please italicize "vir".
Line 36, please delete "modifieds" and replace with --modified--.
Line 49, please italicize "Solanaceae".

Column 14,
Line 18, please italicize "in vitro".

Column 17,
Line 32, please delete "5'GTTTATTTTCCAT<u>CGAT</u>GGAAGGTG" and replace with --5'GTTTATTTTCCAT<u>CGAT</u>GGAAGGTG--.
Line 64, please insert a period after "100ug/ml".

Column 18,
Line 1, please italicize "lacZ".
Line 20, please delete "(Clonetech)" and replace with --(Clontech)--.
Line 43, please delete "CAMV" and replace with --CaMV--.
Line 61, please delete the colon (":") after "transfer".

Column 20,
Line 3, please delete "a glucan" and replace with --α glucan--.
Line 4, please italicize "in vitro".
Line 18, please delete "polyacrylarnide" and replace with --polyacrylarmide--.

Column 21,
Line 3, please delete "reducing," and replace with --reducing--.

Column 22,
Line 14, please delete "cooler." and replace with --cooler--.

UNITED STATES PATENT AND TRADEMARK OFFICE
CERTIFICATE OF CORRECTION

PATENT NO. : 5,998,701
DATED : December 7, 1999
INVENTOR(S) : Kawchuk et al.

It is certified that error appears in the above-identified patent and that said Letters Patent is hereby corrected as shown below:

Column 23,
Line 15, please delete the comma (",") after "testing".
Line 40, please delete "$b^{-1}$" and replace with --$h^{-1}$--.
Line 53, please delete "Wt" and replace with --WT--.

Column 25,
Line 41, please delete "L-type glucan" and replace with --L-type $\alpha$ glucan--.
Line 42, please delete "H-type glucan" and replace with --H-type $\alpha$ glucan--.

In the Claims:

Column 66,
Line 13, please delete " proteins$^{-1}$" and replace with --protein--.
Line 19, please delete "protein$^{-1}$" and replace with --protein--.
Line 25, please delete "protein$^{-1}$" and replace with --protein--.
Line 31, please delete "protein$^{-1}$" and replace with --protein--.
Line 37, please delete "proteins" and replace with --protein$^{-1}$--.
Line 43, please delete "protein$^{-1}$" and replace with --protein--.
Line 49, please delete "protein$^{-1}$" and replace with --protein--.
Line 55, please delete "protein$^{-1}$" and replace with --protein--.
Line 55, please delete "Fop" and replace with --for--.
Line 61, please delete "protein$^{-1}$" and replace with --protein--.
Line 67, please delete "mg protein$^{-1}$" and replace with --$mg^{-1}$ protein--.

UNITED STATES PATENT AND TRADEMARK OFFICE
CERTIFICATE OF CORRECTION

PATENT NO. : 5,998,701
DATED : December 7, 1999
INVENTOR(S) : Kawchuk et al.

It is certified that error appears in the above-identified patent and that said Letters Patent is hereby corrected as shown below:

Column 67,
Line 6, please delete "protein$^{-1}$" and replace with --protein--.
Line 12, please delete "protein$^{-1}$" and replace with --protein--.
Line 18, please delete "protein$^{-1}$" and replace with --protein--.
Line 18, please delete "proteins$^{-1}$" and replace with --protein$^{-1}$--.

Column 68,
Line 55, please delete "phosphotylase" and replace with --phosphorylase--.

Signed and Sealed this

Tenth Day of July, 2001

*Attest:*

*Attesting Officer*

NICHOLAS P. GODICI
*Acting Director of the United States Patent and Trademark Office*